(12) United States Patent
Monaci et al.

(10) Patent No.: US 7,611,868 B2
(45) Date of Patent: Nov. 3, 2009

(54) RECOMBINANT MODIFIED ADENOVIRUS FIBER PROTEIN

(75) Inventors: Paolo Monaci, Rome (IT); Laura Fontana, Pomezia (IT)

(73) Assignee: Instituto di Ricerche di Biologia Molecolare P. Angeletti S.p.A., Rome (IT)

( * ) Notice: Subject to any disclaimer, the term of this patent is extended or adjusted under 35 U.S.C. 154(b) by 475 days.

(21) Appl. No.: 10/556,877

(22) PCT Filed: May 10, 2004

(86) PCT No.: PCT/EP2004/004999

§ 371 (c)(1),
(2), (4) Date: Nov. 4, 2005

(87) PCT Pub. No.: WO2004/101799

PCT Pub. Date: Nov. 25, 2004

(65) Prior Publication Data

US 2006/0281073 A1 Dec. 14, 2006

Related U.S. Application Data

(60) Provisional application No. 60/470,562, filed on May 14, 2003.

(51) Int. Cl.
- C07K 14/75 (2006.01)
- C07K 14/005 (2006.01)
- C12N 15/861 (2006.01)
- A61K 38/00 (2006.01)
- A61K 48/00 (2006.01)

(52) U.S. Cl. .................. 435/69.7; 435/320.1; 435/325; 435/69.1; 530/350; 536/23.4; 536/23.72

(58) Field of Classification Search .................. None
See application file for complete search history.

(56) References Cited

U.S. PATENT DOCUMENTS

| 6,569,677 | B1 | 5/2003 | Legrand et al. | |
|---|---|---|---|---|
| 2002/0081280 | A1* | 6/2002 | Curiel et al. | 424/93.2 |
| 2002/0151027 | A1* | 10/2002 | Wickham et al. | 435/219 |

FOREIGN PATENT DOCUMENTS

| WO | WO 94/10323 | 5/1994 |
|---|---|---|
| WO | WO 94/17832 | 8/1994 |
| WO | WO 95/05201 | 2/1995 |
| WO | WO 95/26412 | 10/1995 |
| WO | WO 96/26281 | 8/1996 |
| WO | WO 97/20051 | 6/1997 |
| WO | WO 98/07865 | 2/1998 |
| WO | WO 98/22609 | 5/1998 |
| WO | WO 98/50053 | 11/1998 |
| WO | WO 99/39734 | 8/1999 |
| WO | WO 99/41359 | 8/1999 |
| WO | WO 99/47180 | 9/1999 |
| WO | WO 00/12738 | 3/2000 |
| WO | WO 00/15823 | 3/2000 |
| WO | WO 01/92299 | 12/2001 |
| WO | WO 03/050238 | 6/2003 |
| WO | WO 2004/099422 | 11/2004 |

OTHER PUBLICATIONS

Fontana, L. et al. "General Strategy for Broadening Adenovirus Tropism", Journal of Virology, vol. 77, pp. 11094-11104, 2003.

Michael, S. et al. "Addition of a short peptide ligand to the adenovirus fiber protein", Gene Therapy, vol. 2, pp. 660-668, 1995.

Gall, J. et al. "Adenovirus Type 5 and 7 Capsid Chimera: Fiber Replacement Alters Receptor Tropism without Affecting Primary Immune Neutralization Epitopes", Journal of Virology, vol. 70, pp. 2116-2123, 1996.

Krasnykh, V. et al. "Generation of Recombinant Adenovirus Vectors with Modified Fibers for Altering Viral Tropism", Journal of Virology, vol. 70, pp. 6839-6846, 1996.

Wickham, T. et al. "Adenovirus targeted to heparan-containing receptors increases its gene delivery efficiency to multiple cell types", Nature Biotechnology, vol. 14, pp. 1570-1578, 1996.

Stevenson, S. et al. "Selective Targeting of Human Cells by a Chimeric Adenovirus Vector Containing a Modified Fiber Protein", Journal of Virology, vol. 71, pp. 4782-4790, 1997.

Wickham, T. et al. "Increased In Vitro and In Vivo Gene Transfer by Adenovirus Vectors Containing Chimeric Fiber Proteins", Journal of Virology, vol. 71, pp. 8221-8229, 1997.

Krasnykh, V. et al. "Characterization of an Adenovirus Vector Containing a Heterologous Peptide Epitope in the HI Loop of the Fiber Knob", Journal of Virology, vol. 72, pp. 1844-1852, 1998.

(Continued)

Primary Examiner—Lisa J Hobbs
(74) Attorney, Agent, or Firm—Sheldon O. Heber; Laura M. Ginkel

(57) ABSTRACT

Recombinant adenoviruses comprising modified fiber proteins which expand the tropism of the adenovirus in comparison to wild-type virus are disclosed. The modified fiber proteins described herein contain a peptide ligand for a cell surface binding site other than CAR comprising a 14 amino acid core sequence containing both fixed and variable amino acid residues. The invention includes isolated nucleic acid molecules encoding the modified adenovirus fiber proteins disclosed, as well as recombinant vectors and host cells containing said nucleic acid molecules. Methods of identifying peptide ligands that bind to cell binding sites other than CAR are included comprising screening a phage-display library of peptide ligands expressed within an adenovirus fiber knob context on CAR-negative cells. Recombinant adenoviruses of the present invention will increase the ability of an adenovirus to transduce important cell and tissue targets as part of a gene therapy/gene vaccination regime that have been shown to be refractory to adenoviral infection.

12 Claims, 24 Drawing Sheets

OTHER PUBLICATIONS

Dmitriev, I. et al. "An Adenovirus Vector with Genetically Modified Fibers Demonstrates Expanded Tropism via Utilization of a Coxsackievirus and Adenovirus Receptor-Independent Cell Entry Mechanism", Journal of Virology, vol. 72, pp. 9706-9713, 1998.

Bouri, K. et al. "Polylysine Modification of Adenoviral Fiber Protein Enhances Muscle Cell Transduction", Human Gene Therapy, vol. 10, pp. 1633-1640, 1999.

Roelvink, P. et al. "Identification of a Conserved Receptor-Binding Site on the Fiber Proteins of Car-Recognizing Adenoviridae", Science, vol. 286, pp. 1568-1571, 1999.

Einfeld, D. et al. "Construction of a Pseudoreceptor That Mediates Transduction by Adenoviruses Expressing a Ligand in Fiber or Penton Base", Journal of Virology, vol. 73, pp. 9130-9136, 1999.

Reynolds, P. et al. "Insertion of an RGD motif into the HI loop of adenovirus fiber protein alters the distribution of transgene expression of the systemically administered vector", Gene Therapy, vol. 6, pp. 1336-1339, 1999.

Krasnykh, V. et al. "Genetic Targeting of Adenoviral Vectors", Molecular Therapy, vol. 1, pp. 391-405, 2000.

Nicklin, S. et al. "Selective Targeting of Gene Transfer to Vascular Endothelial Cells by Use of Peptides Isolated by Phage Display", Circulation, vol. 102, pp. 231-237, 2000.

Silman, N. et al. "Biophysical targeting of adenovirus vectors for gene therapy", Current Opinion in Molecular Therapeutics, vol. 2, pp. 525-532, 2000.

Xia, H. et al. "Recombinant Human Adenovirus: Targeting to the Human Transferrin Receptor Improves Gene Transfer to Brain Microcapillary Endothelium", Journal of Virology, vol. 74, pp. 11359-11366, 2000.

Asada-Mikami, R. et al. "Efficient Gene Transduction by RGD-fiber Modified Recombinant Adenovirus into Dendritic Cells", Jpn. J. Cancer Res., vol. 92, pp. 321-327, 2001.

Havenga, M. et al. "Improved Adenovirus Vectors for Infection of Cardiovascular Tissues", Journal of Virology, vol. 75, pp. 3335-3342, 2001.

Pereboev, A. et al. "Phage Display of Adenovirus Type 5 Fiber Knob as a Tool for Specific Ligand Selection and Validation", Journal of Virology, vol. 75, pp. 7107-7113, 2001.

Urbanelli, L. et al. "Targeted Gene Transduction of Mammalian Cells Expressing the HER2/neu Receptor by Filamentous Phage", J. Mol. Biol., vol. 313, pp. 965-976, 2001.

Okada, N. et al. "Efficient Gene Delivery into Dendritic Cells by Fiber-Mutant Adenovirus Vectors", Biochemical and Biophysical Research Communications, vol. 282, pp. 173-179, 2001.

Mizuguchi, H. et al. "A simplified system for constructing recombinant adenoviral vectors containing heterlogous peptides in the HI loop of their fiber knob", Gene Therapy, vol. 8, pp. 730-735, 2001.

Nicklin, S. et al. "Ablating Adenovirus Type 5 Fiber-CAR Binding and HI Loop Insertion of the SIGYPLP Peptide Generate and Endothelial Cell-Selective Adenovirus", Molecular Therapy, vol. 4, pp. 534-542, 2001.

Belousova, N. et al. "Modulation of Adenovirus Vector Tropism via Incorporation of Polypeptide Ligands into the Fiber Protein", Journal of Virology, vol. 76, pp. 8621-8631, 2002.

Xia, D. et al. "Crystal structure of the receptor-binding domain of adenovirus type 5 fiber protein at 1.7 A resolution", Current Biology, Ltd., vol. 2, pp. 1259-1270, 1994.

Xia, D. et al. "Structure of the Receptor Binding Domain of Adenovirus Type 5 Fiber Protein" *The Molecular Repertoire of Adenoviruses I; Virion Structure and Infection*, Eds. W. Doerfler and P. Bohm, Berlin, Germany, Springer, pp. 38-46, 1995.

Glaser, S. et al. "Antibody Engineering by Codon-Based Mutagenesis in a Filamentous Phage Vector System", The Journal of Immunology, vol. 149, pp. 3903-3913, 1992.

Bett, A. et al. "Packaging Capacity and Stability of Human Adenovirus Type 5 Vectors", Journal of Virology, vol. 67, pp. 5911-5921, 1993.

Stevenson, S. et al. "Human Adenovirus Serotypes 3 and 5 Bind to Two Different Cellular Receptors via the Fiber Head Domain", Journal of Virology, vol. 69, pp. 2850-2857, 1995.

\* cited by examiner

```
  1 MKRARPSEDT FNPVYPYDTE TGPPTVPFLT PPFVSPNGFQ ESPPGVLSLR LSEPLVTSNG
 61 MLALKMGNGL SLDEAGNLTS QNVTTVSPPL KKTKSNINLE ISAPLTVTSE ALTVAAAAPL
121 MVAGNTLTMQ SQAPLTVHDS KLSIATQGPL TVSEGKLALQ TSGPLTTTDS STLTITASPP
181 LTTATGSLGI DLKEPIYTQN GKLGLKYGAP LHVTDDLNTL TVATGPGVTI NNTSLQTKVT
241 GALGFDSQGN MQLNVAGGLR IDSQNRRLIL DVSYPFDAQN QLNLRLGQGP LFINSAHNLD
301 INYNKGLYLF TASNNSKKLE VNLSTAKGLM FDATAIAINA GDGLEFGSPN APNTNPLKTK
361 IGHGLEFDSN KAMVPKLGTG LSFDSTGAIT VGNKNNDKLT LWTTPAPSPN CRLNAEKDAK
421 LTLVLTKCGS QILATVSVLA VKGSLAPISG TVQSAHLIIR FDENGVLLNN SFLDPEYWNF
481 RNGDLTEGTA YTNAVGFMPN LSAYPKSHGK TAKSNIVSQV YLNGDKTKPV TLTITLNGTQ
541 ETGDTTsFCV ASRGGSSCYa aaPSAYSMSF SWDWSGHNYI NEIFATSSYT FSYIAQE*
```
(SEQ ID NO:1)

Fig. 1

```
  1 MKRARPSEDT FNPVYPYDTE TGPPTVPFLT PPFVSPNGFQ ESPPGVLSLR LSEPLVTSNG
 61 MLALKMGNGL SLDEAGNLTS QNVTTVSPPL KKTKSNINLE ISAPLTVTSE ALTVAAAAPL
121 MVAGNTLTMQ SQAPLTVHDS KLSIATQGPL TVSEGKLALQ TSGPLTTTDS STLTITASPP
181 LTTATGSLGI DLKEPIYTQN GKLGLKYGAP LHVTDDLNTL TVATGPGVTI NNTSLQTKVT
241 GALGFDSQGN MQLNVAGGLR IDSQNRRLIL DVSYPFDAQN QLNLRLGQGP LFINSAHNLD
301 INYNKGLYLF TASNNSKKLE VNLSTAKGLM FDATAIAINA GDGLEFGSPN APNTNPLKTK
361 IGHGLEFDSN KAMVPKLGTG LSFDSTGAIT VGNKNNDKLT LWTTPAPSPN CRLNAEKDAK
421 LTLVLTKCGS QILATVSVLA VKGSLAPISG TVQSAHLIIR FDENGVLLNN SFLDPEYWNF
481 RNGDLTEGTA YTNAVGFMPN LSAYPKSHGK TAKSNIVSQV YLNGDKTKPV TLTITLNGTQ
541 ETGDTTsFCK VVGGGSSCSP aaaPSAYSMS FSWDWSGHNY INEIFATSSY TFSYIAQE*
    (SEQ ID NO:2)
```

Fig. 2

```
  1 MKRARPSEDT FNPVYPYDTE TGPPTVPFLT PPFVSPNGFQ ESPPGVLSLR LSEPLVTSNG
 61 MLALKMGNGL SLDEAGNLTS QNVTTVSPPL KKTKSNINLE ISAPLTVTSE ALTVAAAAPL
121 MVAGNTLTMQ SQAPLTVHDS KLSIATQGPL TVSEGKLALQ TSGPLTTTDS STLTITASPP
181 LTTATGSLGI DLKEPIYTQN GKLGLKYGAP LHVTDDLNTL TVATGPGVTI NNTSLQTKVT
241 GALGFDSQGN MQLNVAGGLR IDSQNRRLIL DVSYPFDAQN QLNLRLGQGP LFINSAHNLD
301 INYNKGLYLF TASNNSKKLE VNLSTAKGLM FDATAIAINA GDGLEFGSPN APNTNPLKTK
361 IGHGLEFDSN KAMVPKLGTG LSFDSTGAIT VGNKNNDKLT LWTTPAPSPN CRLNAEKDAK
421 LTLVLTKCGS QILATVSVLA VKGSLAPISG TVQSAHLIIR FDENGVLLNN SFLDPEYWNF
481 RNGDLTEGTA YTNAVGFMPN LSAYPKSHGK TAKSNIVSQV YLNGDKTKPV TLTITLNGTQ
541 ETGDTTsFFC VSDGGGSSCP aaaPSAYSMS FSWDWSGHNY INEIFATSSY TFSYIAQE*
    (SEQ ID NO:3)
```

Fig. 3

```
   1 ATGAAGCGCG CAAGACCGTC TGAAGATACC TTCAACCCCG TGTATCCATA TGACACGGAA
  61 ACCGGTCCTC CAACTGTGCC TTTTCTTACT CCTCCCTTTG TATCCCCCAA TGGGTTTCAA
 121 GAGAGTCCCC CTGGGGTACT CTCTTTGCGC TATCCGAAC CTCTAGTTAC CTCCAATGGC
 181 ATGCTTGCGC TCAAAATGGG CAACGGCCTC TCTCTGGACG AGGCCGGCAA CCTTACCTCC
 241 CAAAATGTAA CCACTGTGAG CCCACCTCTC AAAAAAACCA AGTCAAACAT AAACCTGGAA
 301 ATATCTGCAC CCCTCACAGT TACCTCAGAA GCCCTAACTG TGGCTGCCGC CGCACCTCTA
 361 ATGGTCGCGG GCAACACACT CACCATGCAA TCACAGGCCC CGCTAACCGT GCACGACTCC
 421 AAACTTAGCA TTGCCACCCA AGGACCCCTC ACAGTGTCAG AAGGAAAGCT AGCCCTGCAA
 481 ACATCAGGCC CCTCACCAC CACCGATAGC AGTACCCTTA CTATCACTGC CTCACCCCCT
 541 CTAACTACTG CCACTGGTAG CTTGGGCATT GACTTGAAAG AGCCCATTTA TACACAAAAT
 601 GGAAAACTAG GACTAAAGTA CGGGGCTCCT TGCATGTAA CAGACGACCT AAACACTTTG
 661 ACCGTAGCAA CTGGTCCAGG TGTGACTATT AATAATACTT CCTTGCAAAC TAAAGTTACT
 721 GGAGCCTTGG GTTTTGATTC ACAAGGCAAT ATGCAACTTA ATGTAGCAGG AGGACTAAGG
 781 ATTGATTCTC AAAACAGACG CCTTATACTT GATGTTAGTT ATCCGTTTGA TGCTCAAAAC
 841 CAACTAAATC TAAGACTAGG ACAGGGCCCT CTTTTATAA ACTCAGCCCA CAACTTGGAT
 901 ATTAACTACA ACAAAGGCCT TTACTTGTTT ACAGCTTCAA ACAATTCCAA AAAGCTTGAG
 961 GTTAACCTAA GCACTGCCAA GGGGTTGATG TTTGACGCTA CAGCCATAGC CATTAATGCA
1021 GGAGATGGGC TTGAATTTGG TTCACCTAAT GCACCAAACA CAAATCCCCT CAAAACAAAA
1081 ATTGGCCATG GCCTAGAATT TGATTCAAAC AAGGCTATGG TTCCTAAACT AGGAACTGGC
1141 CTTAGTTTTG ACAGCACAGG TGCCATTACA GTAGGAAACA AAAATAATGA TAAGCTAACT
1201 TTGTGGACCA CACCAGCTCC ATCTCCTAAC TGTAGACTAA ATGCAGAGAA AGATGCTAAA
1261 CTCACTTTGG TCTTAACAAA ATGTGGCAGT CAAATACTTG CTACAGTTTC AGTTTTGGCT
1321 GTTAAAGGCA GTTTGGCTCC AATATCTGGA ACAGTTCAAA GTGCTCATCT TATTATAAGA
1381 TTTGACGAAA ATGGAGTGCT ACTAAACAAT TCCTTCCTGG ACCCAGAATA TTGGAACTTT
1441 AGAAATGGAG ATCTTACTGA AGGCACAGCC TATACAAACG CTGTTGGATT TATGCCTAAC
1501 CTATCAGCTT ATCCAAAATC TCACGGTAAA ACTGCCAAAA GTAACATTGT CAGTCAAGTT
1561 TACTTAAACG GAGACAAAAC TAAACCTGTA ACACTAACCA TTACACTAAA CGGTACACAG
1621 GAAACAGGAG ACACAACTag tTTCTGCGTT GCGTCCCGCG GTGGGTCCTC CTGCTACgcg
1681 gccgctCCtt ccGCATACTC TATGTCATTT TCATGGGACT GGTCTGGCCA CAACTACATT
1741 AATGAAATAT TTGCCACATC CTCTTACACT TTTTCATACA TTGCCCAAGA ATAA
        (SEQ ID NO:4)
```

Fig. 4

```
   1 ATGAAGCGCG CAAGACCGTC TGAAGATACC TTCAACCCCG TGTATCCATA TGACACGGAA
  61 ACCGGTCCTC CAACTGTGCC TTTTCTTACT CCTCCCTTTG TATCCCCCAA TGGGTTTCAA
 121 GAGAGTCCCC CTGGGGTACT CTCTTTGCGC CTATCCGAAC CTCTAGTTAC CTCCAATGGC
 181 ATGCTTGCGC TCAAAATGGG CAACGGCCTC TCTCTGGACG AGGCCGGCAA CCTTACCTCC
 241 CAAAATGTAA CCACTGTGAG CCCACCTCTC AAAAAAACCA AGTCAAACAT AAACCTGGAA
 301 ATATCTGCAC CCCTCACAGT TACCTCAGAA GCCCTAACTG TGGCTGCCGC CGCACCTCTA
 361 ATGGTCGCGG GCAACACACT CACCATGCAA TCACAGGCCC CGCTAACCGT GCACGACTCC
 421 AAACTTAGCA TTGCCACCCA AGGACCCCTC ACAGTGTCAG AAGGAAAGCT AGCCCTGCAA
 481 ACATCAGGCC CCTCACCAC CACCGATAGC AGTACCCTTA CTATCACTGC CTCACCCCCT
 541 CTAACTACTG CCACTGGTAG CTTGGGCATT GACTTGAAAG AGCCCATTTA TACACAAAAT
 601 GGAAAACTAG GACTAAAGTA CGGGGCTCCT TTGCATGTAA CAGACGACCT AAACACTTTG
 661 ACCGTAGCAA CTGGTCCAGG TGTGACTATT AATAATACTT CCTTGCAAAC TAAAGTTACT
 721 GGAGCCTTGG GTTTTGATTC ACAAGGCAAT ATGCAACTTA ATGTAGCAGG AGGACTAAGG
 781 ATTGATTCTC AAAACAGACG CCTTATACTT GATGTTAGTT ATCCGTTTGA TGCTCAAAAC
 841 CAACTAAATC TAAGACTAGG ACAGGGCCCT CTTTTTATAA ACTCAGCCCA CAACTTGGAT
 901 ATTAACTACA ACAAAGGCCT TTACTTGTTT ACAGCTTCAA ACAATTCCAA AAAGCTTGAG
 961 GTTAACCTAA GCACTGCCAA GGGGTTGATG TTTGACGCTA CAGCCATAGC CATTAATGCA
1021 GGAGATGGGC TTGAATTTGG TTCACCTAAT GCACCAAACA CAAATCCCCT CAAAACAAAA
1081 ATTGGCCATG GCCTAGAATT TGATTCAAAC AAGGCTATGG TTCCTAAACT AGGAACTGGC
1141 CTTAGTTTTG ACAGCACAGG TGCCATTACA GTAGGAAACA AAAATAATGA TAAGCTAACT
1201 TTGTGGACCA CACCAGCTCC ATCTCCTAAC TGTAGACTAA ATGCAGAGAA AGATGCTAAA
1261 CTCACTTTGG TCTTAACAAA ATGTGGCAGT CAAATACTTG CTACAGTTTC AGTTTTGGCT
1321 GTTAAAGGCA GTTTGGCTCC AATATCTGGA ACAGTTCAAA GTGCTCATCT TATTATAAGA
1381 TTTGACGAAA ATGGAGTGCT ACTAAACAAT TCCTTCCTGG ACCCAGAATA TTGGAACTTT
1441 AGAAATGGAG ATCTTACTGA AGGCACAGCC TATACAAACG CTGTTGGATT TATGCCTAAC
1501 CTATCAGCTT ATCCAAAATC TCACGGTAAA ACTGCCAAAA GTAACATTGT CAGTCAAGTT
1561 TACTTAAACG GAGACAAAAC TAAACCTGTA ACACTAACCA TTACACTAAA CGGTACACAG
1621 GAAACAGGAG ACACAACTag tTTCTGCAAG GTCGTGGGTG GTGGTTCCTC CTGCTCCCCG
1681 gcggccgctC CttccGCATA CTCTATGTCA TTTTCATGGG ACTGGTCTGG CCACAACTAC
1741 ATTAATGAAA TATTTGCCAC ATCCTCTTAC ACTTTTTCAT ACATTGCCCA AGAATAA
     (SEQ ID NO:5)
```

Fig. 5

```
   1 ATGAAGCGCG CAAGACCGTC TGAAGATACC TTCAACCCCG TGTATCCATA TGACACGGAA
  61 ACCGGTCCTC CAACTGTGCC TTTTCTTACT CCTCCCTTTG TATCCCCCAA TGGGTTTCAA
 121 GAGAGTCCCC CTGGGGTACT CTCTTTGCGC CTATCCGAAC CTCTAGTTAC CTCCAATGGC
 181 ATGCTTGCGC TCAAAATGGG CAACGGCCTC TCTCTGGACG AGGCCGGCAA CCTTACCTCC
 241 CAAAATGTAA CCACTGTGAG CCCACCTCTC AAAAAAACCA AGTCAAACAT AAACCTGGAA
 301 ATATCTGCAC CCCTCACAGT TACCTCAGAA GCCCTAACTG TGGCTGCCGC CGCACCTCTA
 361 ATGGTCGCGG GCAACACACT CACCATGCAA TCACAGGCCC CGCTAACCGT GCACGACTCC
 421 AAACTTAGCA TTGCCACCCA AGGACCCCTC ACAGTGTCAG AAGGAAAGCT AGCCCTGCAA
 481 ACATCAGGCC CCTCACCAC CACCGATAGC AGTACCCTTA CTATCACTGC CTCACCCCCT
 541 CTAACTACTG CCACTGGTAG CTTGGGCATT GACTTGAAAG AGCCCATTTA TACACAAAAT
 601 GGAAAACTAG GACTAAAGTA CGGGGCTCCT TTGCATGTAA CAGACGACCT AAACACTTTG
 661 ACCGTAGCAA CTGGTCCAGG TGTGACTATT AATAATACTT CCTTGCAAAC TAAAGTTACT
 721 GGAGCCTTGG GTTTTGATTC ACAAGGCAAT ATGCAACTTA ATGTAGCAGG AGGACTAAGG
 781 ATTGATTCTC AAAACAGACG CCTTATACTT GATGTTAGTT ATCCGTTTGA TGCTCAAAAC
 841 CAACTAAATC TAAGACTAGG ACAGGGCCCT CTTTTTATAA ACTCAGCCCA CAACTTGGAT
 901 ATTAACTACA ACAAAGGCCT TTACTTGTTT ACAGCTTCAA ACAATTCCAA AAAGCTTGAG
 961 GTTAACCTAA GCACTGCCAA GGGGTTGATG TTTGACGCTA CAGCCATAGC CATTAATGCA
1021 GGAGATGGGC TTGAATTTGG TTCACCTAAT GCACCAAACA CAAATCCCCT CAAAACAAAA
1081 ATTGGCCATG GCCTAGAATT TGATTCAAAC AAGGCTATGG TTCCTAAACT AGGAACTGGC
1141 CTTAGTTTTG ACAGCACAGG TGCCATTACA GTAGGAAACA AAAATAATGA TAAGCTAACT
1201 TTGTGGACCA CACCAGCTCC ATCTCCTAAC TGTAGACTAA ATGCAGAGAA AGATGCTAAA
1261 CTCACTTTGG TCTTAACAAA ATGTGGCAGT CAAATACTTG CTACAGTTTC AGTTTTGGCT
1321 GTTAAAGGCA GTTTGGCTCC AATATCTGGA ACAGTTCAAA GTGCTCATCT TATTATAAGA
1381 TTTGACGAAA ATGGAGTGCT ACTAAACAAT TCCTTCCTGG ACCCAGAATA TTGGAACTTT
1441 AGAAATGGAG ATCTTACTGA AGGCACAGCC TATACAAACG CTGTTGGATT TATGCCTAAC
1501 CTATCAGCTT ATCCAAAATC TCACGGTAAA ACTGCCAAAA GTAACATTGT CAGTCAAGTT
1561 TACTTAAACG GAGACAAAAC TAAACCTGTA ACACTAACCA TTACACTAAA CGGTACACAG
1621 GAAACAGGAG ACACAACTag tTTCTTCTGC GTTTCCGACG GTGGTGGTTC CTCCTGCCCG
1681 gcggccgctC CttccGCATA CTCTATGTCA TTTTCATGGG ACTGGTCTGG CCACAACTAC
1741 ATTAATGAAA TATTTGCCAC ATCCTCTTAC ACTTTTTCAT ACATTGCCCA AGAATAA
     (SEQ ID NO:6)
```

Fig. 6

```
  1 MKRARPSEDT FNPVYPYDTE TGPPTVPFLT PPFVSPNGFQ ESPPGVLSLR LSEPLVTSNG
 61 MLALKMGNGL SLDEAGNLTS QNVTTVSPPL KKTKSNINLE ISAPLTVTSE ALTVAAAAPL
121 MVAGNTLTMQ SQAPLTVHDS KLSIATQGPL TVSEGKLALQ TSGPLTTTDS STLTITASPP
181 LTTATGSLGI DLKEPIYTQN GKLGLKYGAP LHVTDDLNTL TVATGPGVTI NNTSLQTKVT
241 GALGFDSQGN MQLNVAGGLR IDSQNRRLIL DVSYPFDAQN QLNRLGQGP  LFINSAHNLD
301 INYNKGLYLF TASNNSKKLE VNLSTAKGLM FDATAIAINA GDGLEFGSPN APNTNPLKTK
361 IGHGLEFDSN KAMVPKLGTG LSFDSTGAIT VGNKNNDKLT LWTTPAPSPN CRLNAEKDAK
421 LTLVLTKCGS QILATVSVLA VKGSLAPISG TVQSAHLIIR FDENGVLLNN SFLDPEYWNF
481 RNGDLTEGNA VGFMPNLSAY PKSHGKTAKS NIVSQVYLNG DKTKPVTLTI TLNGTQETGD
541 TTsFCVASRG GSSCYaaaPS AYSMSFSWDW SGHNYINEIF ATSSYTFSYI AQE*
```

(SEQ ID NO:7)

Fig. 7

```
  1 MKRARPSEDT FNPVYPYDTE TGPPTVPFLT PPFVSPNGFQ ESPPGVLSLR LSEPLVTSNG
 61 MLALKMGNGL SLDEAGNLTS QNVTTVSPPL KKTKSNINLE ISAPLTVTSE ALTVAAAAPL
121 MVAGNTLTMQ SQAPLTVHDS KLSIATQGPL TVSEGKLALQ TSGPLTTTDS STLTITASPP
181 LTTATGSLGI DLKEPIYTQN GKLGLKYGAP LHVTDDLNTL TVATGPGVTI NNTSLQTKVT
241 GALGFDSQGN MQLNVAGGLR IDSQNRRLIL DVSYPFDAQN QLNLRLGQGP LFINSAHNLD
301 INYNKGLYLF TASNNSKKLE VNLSTAKGLM FDATAIAINA GDGLEFGSPN APNTNPLKTK
361 IGHGLEFDSN KAMVPKLGTG LSFDSTGAIT VGNKNNDKLT LWTTPAPSPN CRLNAEKDAK
421 LTLVLTKCGS QILATVSVLA VKGSLAPISG TVQSAHLIIR FDENGVLLNN SFLDPEYWNF
481 RNGDLTEGNA VGFMPNLSAY PKSHGKTAKS NIVSQVYLNG DKTKPVTLTI TLNGTQETGD
541 TTsFCKVVGG GSSCSPaaaP SAYSMSFSWD WSGHNYINEI FATSSYTFSY IAQE* (SEQ
    ID NO:8)
```

Fig. 8

```
  1 MKRARPSEDT FNPVYPYDTE TGPPTVPFLT PPFVSPNGFQ ESPPGVLSLR LSEPLVTSNG
 61 MLALKMGNGL SLDEAGNLTS QNVTTVSPPL KKTKSNINLE ISAPLTVTSE ALTVAAAAPL
121 MVAGNTLTMQ SQAPLTVHDS KLSIATQGPL TVSEGKLALQ TSGPLTTTDS STLTITASPP
181 LTTATGSLGI DLKEPIYTQN GKLGLKYGAP LHVTDDLNTL TVATGPGVTI NNTSLQTKVT
241 GALGFDSQGN MQLNVAGGLR IDSQNRRLIL DVSYPFDAQN QLNLRLGQGP LFINSAHNLD
301 INYNKGLYLF TASNNSKKLE VNLSTAKGLM FDATAIAINA GDGLEFGSPN APNTNPLKTK
361 IGHGLEFDSN KAMVPKLGTG LSFDSTGAIT VGNKNNDKLT LWTTPAPSPN CRLNAEKDAK
421 LTLVLTKCGS QILATVSVLA VKGSLAPISG TVQSAHLIIR FDENGVLLNN SFLDPEYWNF
481 RNGDLTEGNA VGFMPNLSAY PKSHGKTAKS NIVSQVYLNG DKTKPVTLTI TLNGTQETGD
541 TTsFFCVSDG GGSSCPaaaP SAYSMSFSWD WSGHNYINEI FATSSYTFSY IAQE* (SEQ
    ID NO:9)
```

Fig. 9

```
   1 ATGAAGCGCG CAAGACCGTC TGAAGATACC TTCAACCCCG TGTATCCATA TGACACGGAA
  61 ACCGGTCCTC CAACTGTGCC TTTTCTTACT CCTCCCTTTG TATCCCCCAA TGGGTTTCAA
 121 GAGAGTCCCC CTGGGGTACT CTCTTTGCGC CTATCCGAAC CTCTAGTTAC CTCCAATGGC
 181 ATGCTTGCGC TCAAAATGGG CAACGGCCTC TCTCTGGACG AGGCCGGCAA CCTTACCTCC
 241 CAAAATGTAA CCACTGTGAG CCCACCTCTC AAAAAAACCA AGTCAAACAT AAACCTGGAA
 301 ATATCTGCAC CCCTCACAGT TACCTCAGAA GCCCTAACTG TGGCTGCCGC CGCACCTCTA
 361 ATGGTCGCGG GCAACACACT CACCATGCAA TCACAGGCCC CGCTAACCGT GCACGACTCC
 421 AAACTTAGCA TTGCCACCCA AGGACCCCTC ACAGTGTCAG AAGGAAAGCT AGCCCTGCAA
 481 ACATCAGGCC CCCTCACCAC CACCGATAGC AGTACCCTTA CTATCACTGC CTCACCCCCT
 541 CTAACTACTG CCACTGGTAG CTTGGGCATT GACTTGAAAG AGCCCATTTA TACACAAAAT
 601 GGAAAACTAG GACTAAAGTA CGGGGCTCCT TGCATGTAAC AGACGACCT AAACACTTTG
 661 ACCGTAGCAA CTGGTCCAGG TGTGACTATT AATAATACTT CCTTGCAAAC TAAAGTTACT
 721 GGAGCCTTGG GTTTTGATTC ACAAGGCAAT ATGCAACTTA ATGTAGCAGG AGGACTAAGG
 781 ATTGATTCTC AAAACAGACG CCTTATACTT GATGTTAGTT ATCCGTTTGA TGCTCAAAAC
 841 CAACTAAATC TAAGACTAGG ACAGGGCCCT CTTTTTATAA ACTCAGCCCA CAACTTGGAT
 901 ATTAACTACA ACAAAGGCCT TTACTTGTTT ACAGCTTCAA CAATTCCAA AAAGCTTGAG
 961 GTTAACCTAA GCACTGCCAA GGGGTTGATG TTTGACGCTA CAGCCATAGC CATTAATGCA
1021 GGAGATGGGC TTGAATTTGG TTCACCTAAT GCACCAAACA CAAATCCCCT CAAAACAAAA
1081 ATTGGCCATG GCCTAGAATT TGATTCAAAC AAGGCTATGG TTCCTAAACT AGGAACTGGC
1141 CTTAGTTTTG ACAGCACAGG TGCCATTACA GTAGGAAACA AAATAATGA TAAGCTAACT
1201 TTGTGGACCA CACCAGCTCC ATCTCCTAAC TGTAGACTAA ATGCAGAGAA AGATGCTAAA
1261 CTCACTTTGG TCTTAACAAA ATGTGGCAGT CAAATACTTG CTACAGTTTC AGTTTTGGCT
1321 GTTAAAGGCA GTTTGGCTCC AATATCTGGA ACAGTTCAAA GTGCTCATCT TATTATAAGA
1381 TTTGACGAAA ATGGAGTGCT ACTAAACAAT TCCTTCCTGG ACCCAGAATA TTGGAACTTT
1441 AGAAATGGAG ATCTTACTGA AGGCAACGCT GTTGGATTTA TGCCTAACCT ATCAGCTTAT
1501 CCAAAATCTC ACGGTAAAAC TGCCAAAAGT AACATTGTCA GTCAAGTTTA CTTAAACGGA
1561 GACAAAACTA AACCTGTAAC ACTAACCATT ACACTAAACG GTACACAGGA AACAGGAGAC
1621 ACAACTAgtT TCTGCGTTGC GTCCCGCGGT GGGTCCTCCT GCTACgcggc cgctCCttcc
1681 GCATACTCTA TGTCATTTTC ATGGGACTGG TCTGGCCACA ACTACATTAA TGAAATATTT
1741 GCCACATCCT CTTACACTTT TTCATACATT GCCCAAGAAT AA (SEQ ID NO:10)
```

Fig. 10

```
   1 ATGAAGCGCG CAAGACCGTC TGAAGATACC TTCAACCCCG TGTATCCATA TGACACGGAA
  61 ACCGGTCCTC CAACTGTGCC TTTTCTTACT CCTCCCTTTG TATCCCCCAA TGGGTTTCAA
 121 GAGAGTCCCC CTGGGGTACT CTCTTTGCGC CTATCCGAAC CTCTAGTTAC CTCCAATGGC
 181 ATGCTTGCGC TCAAAATGGG CAACGGCCTC TCTCTGGACG AGGCCGGCAA CCTTACCTCC
 241 CAAAATGTAA CCACTGTGAG CCCACCTCTC AAAAAAACCA AGTCAAACAT AAACCTGGAA
 301 ATATCTGCAC CCCTCACAGT TACCTCAGAA GCCCTAACTG TGGCTGCCGC CGCACCTCTA
 361 ATGGTCGCGG GCAACACACT CACCATGCAA TCACAGGCCC CGCTAACCGT GCACGACTCC
 421 AAACTTAGCA TTGCCACCCA AGGACCCCTC ACAGTGTCAG AAGGAAAGCT AGCCCTGCAA
 481 ACATCAGGCC CCCTCACCAC CACCGATAGC AGTACCCTTA CTATCACTGC CTCACCCCCT
 541 CTAACTACTG CCACTGGTAG CTTGGGCATT GACTTGAAAG AGCCCATTTA TACACAAAAT
 601 GGAAAACTAG GACTAAAGTA CGGGGCTCCT TTGCATGTAA CAGACGACCT AAACACTTTG
 661 ACCGTAGCAA CTGGTCCAGG TGTGACTATT AATAATACTT CCTTGCAAAC TAAAGTTACT
 721 GGAGCCTTGG GTTTTGATTC ACAAGGCAAT ATGCAACTTA ATGTAGCAGG AGGACTAAGG
 781 ATTGATTCTC AAAACAGACG CCTTATACTT GATGTTAGTT ATCCGTTTGA TGCTCAAAAC
 841 CAACTAAATC TAAGACTAGG ACAGGGCCCT CTTTTATAA ACTCAGCCCA AACTTGGAT
 901 ATTAACTACA ACAAAGGCCT TTACTTGTTT ACAGCTTCAA ACAATTCCAA AAAGCTTGAG
 961 GTTAACCTAA GCACTGCCAA GGGGTTGATG TTTGACGCTA CAGCCATAGC CATTAATGCA
1021 GGAGATGGGC TTGAATTTGG TTCACCTAAT GCACCAAACA CAAATCCCCT CAAAACAAAA
1081 ATTGGCCATG GCCTAGAATT TGATTCAAAC AAGGCTATGG TTCCTAAACT AGGAACTGGC
1141 CTTAGTTTTG ACAGCACAGG TGCCATTACA GTAGGAAACA AAAATAATGA TAAGCTAACT
1201 TTGTGGACCA CACCAGCTCC ATCCTAAC TGTAGACTAA ATGCAGAGAA AGATGCTAAA
1261 CTCACTTTGG TCTTAACAAA ATGTGGCAGT CAAATACTTG CTACAGTTTC AGTTTTGGCT
1321 GTTAAAGGCA GTTTGGCTCC AATATCTGGA ACAGTTCAAA GTGCTCATCT TATTATAAGA
1381 TTTGACGAAA ATGGAGTGCT ACTAAACAAT TCCTTCCTGG ACCCAGAATA TTGGAACTTT
1441 AGAAATGGAG ATCTTACTGA AGGCAACGCT GTTGGATTTA TGCCTAACCT ATCAGCTTAT
1501 CCAAAATCTC ACGGTAAAAC TGCCAAAAGT AACATTGTCA GTCAAGTTTA CTTAAACGGA
1561 GACAAAACTA AACCTGTAAC ACTAACCATT ACACTAAACG GTACACAGGA AACAGGAGAC
1621 ACAACTagtT TCTGCAAGGT CGTGGGTGGT GGTTCCTCCT GCTCCCCGgc ggccgctCCt
1681 tccGCATACT CTATGTCATT TTCATGGGAC TGGTCTGGCC ACAACTACAT TAATGAAATA
1741 TTTGCCACAT CCTCTTACAC TTTTTCATAC ATTGCCCAAG AATAA (SEQ ID NO:11)
```

Fig. 11

```
   1 ATGAAGCGCG CAAGACCGTC TGAAGATACC TTCAACCCCG TGTATCCATA TGACACGGAA
  61 ACCGGTCCTC CAACTGTGCC TTTTCTTACT CCTCCCTTTG TATCCCCCAA TGGGTTTCAA
 121 GAGAGTCCCC CTGGGGTACT CTCTTTGCGC CTATCCGAAC CTCTAGTTAC CTCCAATGGC
 181 ATGCTTGCGC TCAAAATGGG CAACGGCCTC TCTCTGGACG AGGCCGGCAA CCTTACCTCC
 241 CAAAATGTAA CCACTGTGAG CCCACCTCTC AAAAAAACCA AGTCAAACAT AAACCTGGAA
 301 ATATCTGCAC CCCTCACAGT TACCTCAGAA GCCCTAACTG TGGCTGCCGC CGCACCTCTA
 361 ATGGTCGCGG GCAACACACT CACCATGCAA TCACAGGCCC CGCTAACCGT GCACGACTCC
 421 AAACTTAGCA TTGCCACCCA AGGACCCCTC ACAGTGTCAG AAGGAAAGCT AGCCCTGCAA
 481 ACATCAGGCC CCCTCACCAC CACCGATAGC AGTACCCTTA CTATCACTGC CTCACCCCCT
 541 CTAACTACTG CCACTGGTAG CTTGGGCATT GACTTGAAAG AGCCCATTTA TACACAAAAT
 601 GGAAAACTAG GACTAAAGTA CGGGGCTCCT TTGCATGTAA CAGACGACCT AAACACTTTG
 661 ACCGTAGCAA CTGGTCCAGG TGTGACTATT AATAATACTT CCTTGCAAAC TAAAGTTACT
 721 GGAGCCTTGG GTTTTGATTC ACAAGGCAAT ATGCAACTTA ATGTAGCAGG AGGACTAAGG
 781 ATTGATTCTC AAAACAGACG CCTTATACTT GATGTTAGTT ATCCGTTTGA TGCTCAAAAC
 841 CAACTAAATC TAAGACTAGG ACAGGGCCCT CTTTTTATAA ACTCAGCCCA CAACTTGGAT
 901 ATTAACTACA ACAAAGGCCT TTACTTGTTT ACAGCTTCAA ACAATTCCAA AAAGCTTGAG
 961 GTTAACCTAA GCACTGCCAA GGGGTTGATG TTTGACGCTA CAGCCATAGC CATTAATGCA
1021 GGAGATGGGC TTGAATTTGG TTCACCTAAT GCACCAAACA CAAATCCCCT CAAAACAAAA
1081 ATTGGCCATG GCCTAGAATT TGATTCAAAC AAGGCTATGG TTCCTAAACT AGGAACTGGC
1141 CTTAGTTTTG ACAGCACAGG TGCCATTACA GTAGGAAACA AAATAATGA TAAGCTAACT
1201 TTGTGGACCA CACCAGCTCC ATCTCCTAAC TGTAGACTAA ATGCAGAGAA AGATGCTAAA
1261 CTCACTTTGG TCTTAACAAA ATGTGGCAGT CAAATACTTG CTACAGTTTC AGTTTTGGCT
1321 GTTAAAGGCA GTTTGGCTCC AATATCTGGA ACAGTTCAAA GTGCTCATCT TATTATAAGA
1381 TTTGACGAAA ATGGAGTGCT ACTAAACAAT TCCTTCCTGG ACCCAGAATA TTGGAACTTT
1441 AGAAATGGAG ATCTTACTGA AGGCAACGCT GTTGGATTTA TGCCTAACCT ATCAGCTTAT
1501 CCAAAATCTC ACGGTAAAAC TGCCAAAAGT AACATTGTCA GTCAAGTTTA CTTAAACGGA
1561 GACAAAACTA AACCTGTAAC ACTAACCATT ACACTAAACG GTACACAGGA AACAGGAGAC
1621 ACAACTagtT TCTTCTGCGT TTCCGACGGT GGTGGTTCCT CCTGCCCGgc ggccgctCCt
1681 tccGCATACT CTATGTCATT TTCATGGGAC TGGTCTGGCC ACAACTACAT TAATGAAATA
1741 TTTGCCACAT CCTCTTACAC TTTTTCATAC ATTGCCCAAG AATAA (SEQ ID NO:12)
```

Fig. 12

| λD | linker | RBS | | Ad5 fiber knob |
|---|---|---|---|---|
| ...S I V<br>110 | [ G S ]₁₆ | G K E V P | * | M G A I ...(SEQ ID NO:18)<br>406 |
| ...AGCATCGTT | [GGATCT]₁₆ | GGTAAGGAGGTACCG | TAG | ATGGGTGCCATT...(SEQ ID NO:19) |

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| knobΔ-L1 |  | F | C | V | A | S | R | G | G | S | S | C | Y |  |
| knobΔ-L16 |  | F | C | K | V | V | G | G | G | S | S | C | S | P |
| knobΔ-L33 | F | F | C | V | S | D | G | G | G | S | S | C | P |  |

(SEQ ID NO:13)
(SEQ ID NO:14)
(SEQ ID NO:15)

Fig. 18

RECOMBINANT MODIFIED ADENOVIRUS FIBER PROTEIN

CROSS-REFERENCE TO RELATED APPLICATIONS

The present application is the §371 National Stage application of PCT International Application serial no. PCT/EP2004/004999, having an international filing date of May 10, 2004, which claims priority to U.S. Provisional Application Ser. No. 60/470,562, filed May 14, 2003, now expired.

FIELD OF THE INVENTION

The present invention relates generally to a recombinant adenovirus having a modified fiber protein that broadens the tropism of the adenovirus in comparison to wild-type virus. The modified fiber protein contains a peptide ligand for a cell surface binding site other than the coxsackievirus and adenovirus receptor (CAR) comprising a 14 amino acid core sequence containing both fixed and variable amino acid residues. The peptide ligand is inserted within the adenovirus fiber protein sequence such that it is accessible to the alternative cell surface binding site, and yet fiber knob trimerization is preserved. The present invention also relates to isolated nucleic acid molecules which encode the modified adenovirus fiber proteins disclosed, as well as recombinant vectors and hosts cells containing said nucleic acid molecules. The present invention further relates to a phage-display library wherein said library contains a population of recombinant phage which express a phage coat protein fused to a modified adenovirus fiber knob comprising a peptide ligand for a cell surface binding site other than CAR. The invention also relates to a method of identifying said peptide ligands by screening said library on CAR-negative or CAR-positive cells, as well as methods for transducing cells and/or tissues with a recombinant adenovirus described herein.

BACKGROUND OF THE INVENTION

Recombinant adenovirus vectors have proven to be an efficient and versatile gene therapy system for the targeted transfer of recombinant genes to diseased cells or tissue. Adenovirus vectors infect a broad range of target cells; however, high levels of gene transfer depend upon the presence of the coxsackievirus and adenovirus receptor (CAR) in the target cell. Several cell types and tissues that represent important targets for gene therapy are refractory to adenoviral infection, mainly because of low CAR expression levels (see, e.g., Havenga et al., 2001, *J. Virol.* 75:3335-3342). Similarly, some target cells that are readily infected by adenovirus require high levels of adenovirus particles to achieve transduction (Arthur et al., 1997, *Cancer Gene Ther.* 4:17-25), exacerbating any immune response associated with adenoviral infection. Thus, considerable efforts have been directed toward increasing the efficiency of adenovirus delivery to therapeutically relevant human cells and tissues.

The cellular entry mechanism of adenovirus serotype 5 (Ad5) is composed of two separate and uncoupled steps. First, the virus binds to the host cell through a high-affinity interaction between the trimeric carboxy-terminal knob domain of the viral fiber proteins and CAR displayed on the cell surface. This primary interaction, which dictates the infectivity of the virus is followed by the association of RGD sequences in the penton base with $\alpha_v\beta_3$ and $\alpha_v\beta_5$ integrins on the cell-surface, thereby activating internalization of the virus. Strategies to alter Ad5 tropism are based on modification of the viral capsid proteins to permit the recognition of alternative cell-specific receptors. Adenovirus capsid proteins include hexon, penton base, and fiber proteins. Since the binding of the virus with its cognate cellular receptor controls the tropism of the virus, the majority of efforts have been directed at genetically modifying the carboxy-terminal knob domain of the fiber protein (for a review, see Krasnyhk et al., 2000, *Mol. Ther.* 1:391-405). Many laboratories have shown that it is possible to replace the Ad5 fiber gene, either partially or completely, with that of different adenovirus serotypes, thus generating a tropism derived from the donor serotype. Indeed, some of the Ad5-chimeras that have been created exhibit enhanced tropism for defined cell types. However, the flexibility of this "fiber swapping" approach is hampered by the number of serotypes available and their limited tropism. In addition, impaired viability and reduced yield of the viral chimeras have limited the exploitation of this strategy.

Recently, various labs have shown that short peptides can be incorporated at defined sites of the Ad5 fiber knob domain. The HI loop, which protrudes from the knob domain, structurally tolerates the insertion of a wide number of peptide sequences leaving fiber trimerization and CAR binding function intact. These findings prompted the screening of phage-displayed peptide libraries as a promising route to identify ligands with a desired binding specificity. The fact that ligands selected from phage libraries often do not retain their binding properties when grafted into a different protein location, i.e. the HI loop of the Ad5 fiber knob, has resulted in a paucity of successful reports using this strategy. Furthermore, insertion of these peptides can affect fiber trimerization and virus assembly.

Krasnykh et al. (1998, *J. Virol.* 72:1844-1852) recombinantly expressed an Ad5 fiber protein containing a FLAG octapeptide within the HI loop domain of the fiber knob. The heterologous peptide did not ablate fiber trimerization or disturb formation of the cell-binding site within the knob. Recombinant adenovirus containing said modified Ad5 fiber protein maintained proper biological function.

Dmitriev et al. (1998, *J. Virol.* 72:9706-9713) show that the incorporation of a peptide containing Arg-Gly-Asp (RGD) into the HI loop of the Ad5 fiber loop allowed the resulting recombinant fiber to utilize the RGD-integrin interaction as an alternative infection pathway to CAR.

Einfeld et al. (1999, *J. Virol.* 73:9130-9136) developed a pseudoreceptor consisting of a membrane-anchored single-chain antibody that recognizes a linear decapeptide from the hemagglutinin (HA) protein. Incorporation of this HA peptide into the HI loop of the Ad2 fiber knob enabled the resulting recombinant adenovirus to transduce pseudoreceptor expressing cells under conditions where CAR binding was blocked.

Xia et al. (2000, *J. Virol.* 74:11359-11366) screened a nonapeptide phage-display library against the extracellular domain of the human transferrin receptor (hTfR) to identify epitopes specific to the receptor. Two of the sequences identified were inserted within the HI loop of the Ad5 fiber knob, showing proper fiber trimerization and gene transfer to hTfR expressing cells.

Nicklin et al. (2001, *Mol. Ther.* 4:534-542) demonstrated that two endothelial cell (EC)-binding peptides redirected adenovirus tropism to ECs when inserted within the HI loop of the fiber knob in which CAR binding had been ablated.

The present invention overcomes the limitations of the previous work by expressing a functional Ad5 fiber knob domain on the capsid of bacteriophage λ as a carboxy-terminal fusion to the major head protein D. This phage display system was employed to construct a large collection of peptide sequences incorporated within a functional Ad5 fiber knob wherein the binding to wild-type CAR was ablated. After panning this library on CAR-negative mouse embryo fibroblasts NIH-3T3, three peptide ligands in the knob context were isolated that show binding to CAR-negative cells.

Viruses incorporating these peptides ligands have an enhanced infectivity of CAR-negative cells and cells expressing low levels of CAR. Accordingly, generating recombinant adenoviruses comprising a modified fiber protein incorporating these novel peptide ligands injects a higher activity and functionality into the adenovirus gene therapy/gene vaccination system.

SUMMARY OF THE INVENTION

The present invention relates to a recombinant adenovirus having a modified fiber protein which comprises a peptide ligand for a cell surface binding site other than CAR. The peptide ligand comprises a core amino acid sequence of 14 residue positions such that residue positions one, two and thirteen are Xaa residues, preferably tyrosine (Tyr), tryptophan (Trp), or phenylalanine (Phe); residue positions three and twelve are cysteine (Cys) residues; residue positions four through eleven are Xaa residues, preferably glycine (Gly), serine (Ser), or valine (Val); and, residue position fourteen is an Xaa residue, preferably proline (Pro). The core amino acid sequence may be deleted by one or more residues at any residue position within the sequence, except at the fixed Cys residues at position three and position twelve. It is preferable that the region of the core amino acid sequence located between the fixed Cys residues comprises at least two amino acid residues. Additionally, up to 10 amino acid residues may be added between residue position three and residue position twelve. The amino acid sequence of the peptide ligand does not comprise a consecutive Arg-Gly-Asp (RGD) sequence between residue positions three and twelve, and the peptide ligand does not consist of the amino acid sequence as disclosed in SEQ ID NO:46. A recombinant adenovirus having a modified fiber protein with the ability to bind to a cell surface binding site other than CAR has an effect of broadening the wild-type tropism of the adenovirus, expanding the functionality of the adenovirus system for gene therapy.

The present invention further relates to a recombinant adenovirus with a modified fiber protein which comprises a peptide ligand for a cell surface binding site other than CAR, wherein the peptide ligand comprises a core amino acid sequence of 14 residue positions such that residue positions one and thirteen are Xaa residues, preferably tyrosine (Tyr), tryptophan (Trp), or phenylalanine (Phe); residue position two is a phenylalanine (Phe) residue; residue positions three and twelve are cysteine (Cys) residues; residue positions four through eleven are Xaa residues, preferably glycine (Gly), serine (Ser), or valine (Val); and residue position fourteen is an Xaa residue, preferably proline (Pro). The core amino acid sequence may be deleted by one or more residues at any residue position within the sequence, except at the fixed Cys residues at position three and position twelve or the Phe residue at position two. It is preferable that the region of the core amino acid sequence located between the fixed Cys residues comprises at least two amino acid residues. Additionally, up to 10 amino acid residues may be added between residue position three and residue position twelve. The amino acid sequence of the peptide ligand does not comprise a consecutive Arg-Gly-Asp (RGD) sequence between residue positions three and twelve.

The present invention also relates to a recombinant adenovirus having a modified fiber protein which comprises a peptide ligand for a cell surface binding site other than CAR, wherein the peptide ligand comprises a core amino acid sequence of 14 residue positions such that residue positions one, two and thirteen are Xaa residues, preferably tyrosine (Tyr), tryptophan (Trp), or phenylalanine (Phe); residue positions three and twelve are cysteine (Cys) residues; residue positions four through seven are Xaa residues, preferably glycine (Gly), serine (Ser), or valine (Val); residue positions eight and nine are glycine (Gly) residues; residue positions ten and eleven are serine (Ser) residues; and, residue position fourteen is an Xaa residue, preferably proline (Pro). The core amino acid sequence may be deleted by one or more residues at the variable residue positions within the sequence including residue positions one, two, four through seven, thirteen and fourteen. Additionally, up to 10 amino acid residues may be added between residue position three and residue position eight. The amino acid sequence of the peptide ligand does not comprise a consecutive Arg-Gly-Asp (RGD) sequence between residue positions three and eight.

The present invention further relates to a recombinant adenovirus with a modified fiber protein which comprises a peptide ligand for a cell surface binding site other than CAR, wherein the peptide ligand comprises a core amino acid sequence of 14 residue positions such that residue positions one and thirteen are Xaa residues, preferably tyrosine (Tyr), tryptophan (Trp), or phenylalanine Phe); residue position two is a phenylalanine (Phe) residue; residue positions three and twelve are cysteine (Cys) residues; residue positions four through seven are Xaa residues, preferably glycine (Gly), serine (Ser), or valine (Val); residue positions eight and nine are glycine (Gly) residues; residue positions ten and eleven are serine (Ser) residues; and, residue position fourteen is an Xaa residue, preferably proline (Pro). The core amino acid sequence may be deleted by one or more residues at the variable residue positions within the sequence including residue positions one, four through seven, thirteen and fourteen. Additionally, up to 10 amino acid residues may be added between residue position three and residue position eight. The amino acid sequence of the peptide ligand does not comprise a consecutive Arg-Gly-Asp (RGD) sequence between residue positions three and eight.

The present invention also relates to a recombinant adenovirus with a modified fiber protein which comprises a peptide ligand for a cell surface binding site other than CAR, said peptide ligand comprising a core amino acid sequence as described in each of the embodiments listed above. The core amino acid sequence may be deleted by one or more residues at any residue position within the sequence, except at the fixed residue positions. It is preferable that the region of the core amino acid sequence located between the fixed Cys residues at position three and position twelve comprises at least two amino acid residues. The amino acid sequence of the peptide ligand does not comprise a consecutive Arg-Gly-Asp (RGD) sequence between residue positions three and twelve, and the peptide ligand does not consist of the amino acid sequence as disclosed in SEQ ID NO:46.

The present invention also relates to a recombinant adenovirus having a modified fiber protein comprising a peptide ligand for a cell surface binding site other than CAR, wherein said peptide ligand comprises the amino acid sequence selected from the group consisting of SEQ ID NO:13, SEQ ID NO:14 and SEQ ID NO:15.

The present invention relates to a recombinant adenovirus containing a fiber protein modified as described herein such that the peptide ligand of the modified adenovirus fiber protein is integrated within any portion of the fiber protein that enables accessibility of the peptide ligand to the cell surface binding site. In one embodiment, the peptide ligand is inserted within an exposed loop domain of the adenovirus fiber knob, preferably from Ad5, including but not limited to the HI loop domain of the Ad5 fiber knob. In particular, the peptide ligand can be inserted between amino acid residue 546 and amino acid residue 547 of the Ad5 fiber protein within the HI loop of the fiber knob.

The present invention relates to a recombinant adenovirus comprising a modified Ad5 fiber protein consisting of the amino acid sequence as disclosed in FIG. 1 and as set forth in SEQ ID NO:1.

The present invention also relates to a recombinant adenovirus comprising a modified Ad5 fiber protein consisting of the amino acid sequence as disclosed in FIG. 2 and as set forth in SEQ ID NO:2.

The present invention further relates to a recombinant adenovirus comprising a modified Ad5 fiber protein consisting of the amino acid sequence as disclosed in FIG. 3 and as set forth in SEQ ID NO:3.

The present invention is also directed to a recombinant adenovirus wherein, prior to modification, the adenovirus is of a first serotype; and after modification, at least a portion of the fiber protein of said first adenovirus serotype has been removed and replaced with the same or similar portion of a fiber protein from a second adenovirus serotype, wherein said portion of the second adenovirus serotype fiber protein has been modified as described in this specification. The portion of the fiber protein from said second adenovirus serotype which is used to replace the portion of the fiber protein removed from said first adenovirus serotype contains a peptide ligand as described in this specification. Therefore, one embodiment of the present invention relates to a recombinant adenovirus wherein the fiber protein, or a portion thereof, has been replaced by a modified fiber protein, or portion thereof, containing a peptide ligand, of an alternate serotype of human or non-human origin. If the modified adenovirus fiber protein comprises a peptide ligand contained within its knob domain, the knob domain comprising the peptide ligand can be used to replace a wild-type knob domain of the alternate adenovirus serotype. In particular, the present invention relates to a recombinant adenovirus of any serotype of human origin or non-human origin, including but not limited to chimp, rhesus, dog, cat, and avian, wherein the knob domain of the fiber protein is replaced with the knob domain of an Ad5 fiber knob which contains a peptide ligand as described in this specification.

The present invention also relates to a recombinant adenovirus comprising a modified fiber protein as disclosed herein which is further modified to abolish the wild-type cell surface binding of the fiber protein. In one embodiment, a modified Ad5 fiber protein as disclosed herein is further modified to abolish CAR binding of the modified protein. CAR binding of the Ad5 fiber protein is ablated as a result of specific sequence modifications to the fiber protein, including but not limited to the deletion of amino acid residue 489 to amino acid residue 492 of the protein. The inability of a recombinant adenovirus of the present invention to bind its wild-type cell surface binding site will help to target the recombinant adenovirus to specific cell types expressing the cell surface binding site of the particular peptide ligand incorporated within the modified fiber domain.

The present invention relates to a recombinant adenovirus comprising a modified Ad5 fiber protein consisting of the amino acid sequence as disclosed in FIG. 7 and as set forth in SEQ ED NO:7, wherein wild-type CAR binding of the modified Ad5 fiber protein is ablated.

The present invention also relates to a recombinant adenovirus comprising a modified Ad5 fiber protein consisting of the amino acid sequence as disclosed in FIG. 8 and as set forth in SEQ ID NO:8, wherein wild-type CAR binding of the modified Ad5 fiber protein is ablated.

The present invention further relates to a recombinant adenovirus comprising a modified Ad5 fiber protein consisting of the amino acid sequence as disclosed in FIG. 9 and as set forth in SEQ ID NO:9, wherein wild-type CAR binding of the modified Ad5 fiber protein is ablated.

The present invention relates to an isolated adenovirus fiber protein that is modified to encompass the characteristics described above. Any one of the serotypes of human or non-human adenovirus can be used as the source of the fiber protein gene. The modified adenovirus fiber protein of the present invention, including but not limited to a modified Ad5 fiber protein, is a fiber protein having a peptide ligand, as described in this specification, inserted within its coding region. In one embodiment, the peptide ligand is inserted within an exposed loop domain of the fiber knob, including but not limited to the HI loop domain. For example, the peptide ligand can be inserted between amino acid residue 546 and amino acid residue 547 located within the HI loop of the Ad5 fiber protein. The present invention also includes a modified fiber protein wherein a knob domain of the fiber protein of one adenovirus serotype is replaced with a knob domain of an alternate adenovirus serotype which contains a peptide ligand of the present invention. An isolated adenovirus fiber protein that is modified as described in the present application can be used as a tool to identify the therapeutically relevant cells and tissues to which the modified protein will bind, indicating the possibility of transduction with vectors containing said modified fiber proteins. The modified, isolated adenovirus fiber protein as described can also be used as a "binding determinant" that can be linked to other moieties (i.e., virus, protein or DNA) in order to direct said moiety to a target receptor.

The present invention is also directed to a modified adenovirus fiber protein wherein, prior to modification, the fiber protein is of a first adenovirus serotype; and after modification, at least a portion of the fiber protein of said first adenovirus serotype has been removed and replaced with a similar portion of a modified fiber protein of a second adenovirus serotype. The portion of the fiber protein from the second adenovirus serotype which is used to replace the portion removed from the first adenovirus serotype fiber protein contains a peptide ligand as described in this specification. Therefore, one embodiment of the present invention relates to a modified adenovirus fiber protein comprising a portion of a fiber protein from an alternative adenovirus serotype which contains a peptide ligand as described in this specification. If the modified adenovirus fiber protein comprises a peptide ligand within its knob domain, the knob domain comprising the peptide ligand can be used to replace a wild-type knob domain of an alternate adenovirus serotype. In particular, the present invention relates to a modified adenovirus fiber protein of any serotype of human or non-human origin wherein the knob domain of the fiber protein is replaced with the knob domain of an Ad5 fiber knob containing a peptide ligand as described in this specification.

The present invention relates to an isolated Ad5 fiber protein consisting of the amino acid sequence as disclosed in FIG. 1 and as set forth in SEQ ID NO:1.

The present invention also relates to an isolated Ad5 fiber protein consisting of the amino acid sequence as disclosed in FIG. 2 and as set forth in SEQ ID NO:2.

The present invention further relates to an isolated Ad5 fiber protein consisting of the amino acid sequence as disclosed in FIG. 3 and as set forth in SEQ ID NO:3.

The present invention also relates to a modified fiber protein as disclosed herein that has been further modified to abolish binding to its wild-type cell surface binding site. In one embodiment, wild-type CAR binding of a modified Ad5 fiber protein is ablated. CAR binding of the Ad5 fiber protein is ablated as a result of specific sequence modifications to the fiber protein, including but not limited to deletion of amino acid residue 489 to amino acid residue 492.

The present invention relates to an isolated Ad5 fiber protein consisting of the amino acid sequence as disclosed in FIG. 7 and as set forth in SEQ ID NO:7, wherein wild-type CAR binding of the modified Ad5 fiber protein is ablated.

The present invention also relates to an isolated Ad5 fiber protein consisting of the amino acid sequence as disclosed in FIG. 8 and as set forth in SEQ ID NO:8, wherein wild-type CAR binding of the modified Ad5 fiber protein is ablated.

The present invention further relates to an isolated Ad5 fiber protein consisting of the amino acid sequence as disclosed in FIG. 9 and as set forth in SEQ ID NO:9, wherein wild-type CAR binding of the modified Ad5 fiber protein is ablated.

The present invention relates to an isolated peptide ligand consisting of the amino acid sequence as set forth in SEQ ID NO:13.

The present invention also relates to an isolated peptide ligand consisting of the amino acid sequence as set forth in SEQ ID NO:14.

The present invention further relates to an isolated peptide ligand consisting of the amino acid sequence as set forth in SEQ ID NO:15.

The present invention relates to an isolated nucleic acid molecule encoding a modified adenovirus fiber protein, including but not limited to a modified Ad5 fiber protein, encompassing the characteristics described above. The isolated nucleic acid molecule of the present invention may include a deoxyribonucleic acid molecule (DNA) which may be single (coding or noncoding strand) or double stranded, as well as synthetic DNA, such as a synthesized, single stranded polynucleotide. The isolated nucleic acid molecule of the present invention may also include a ribonucleic acid molecule (RNA). The present invention also relates to recombinant vectors and recombinant hosts, both prokaryotic and eukaryotic, which contain the isolated nucleic acid molecules disclosed throughout this specification, in addition to a process of expressing a modified adenovirus fiber protein of the present invention in a recombinant host cell.

The present invention relates to an isolated nucleic acid molecule encoding a modified Ad5 fiber protein consisting of the nucleotide sequence as disclosed in FIG. 4 and as set forth in SEQ ID NO:4.

The present invention also relates to an isolated nucleic acid molecule encoding a modified Ad5 fiber protein consisting of the nucleotide sequence as disclosed in FIG. 5 and as set forth in SEQ ID NO:5.

The present invention further relates to an isolated nucleic acid molecule encoding a modified Ad5 fiber protein consisting of the nucleotide sequence as disclosed in FIG. 6 and as set forth in SEQ ID NO:6.

The present invention relates to an isolated nucleic acid molecule encoding a modified Ad5 fiber protein that lacks the ability to bind CAR consisting of the nucleotide sequence as disclosed in FIG. 10 and as set forth in SEQ ID NO:10.

The present invention also relates to an isolated nucleic acid molecule encoding a modified Ad5 fiber protein that lacks the ability to bind CAR consisting of the nucleotide sequence as disclosed in FIG. 11 and as set forth in SEQ ID NO:11.

The present invention further relates to an isolated nucleic acid molecule encoding a modified Ad5 fiber protein that lacks the ability to bind CAR consisting of the nucleotide sequence as disclosed in FIG. 12 and as set forth in SEQ ID NO:12.

Other aspects of this invention include adenoviral vectors comprising the nucleic acid molecules encoding the modified adenovirus fiber proteins described herein, including but not limited to adenoviral vectors that are at least partially deleted in E1 and devoid of E1 activity; packaging cells comprising the adenoviral vectors; and host cells from which to harvest the recombinant adenovirus, including but not limited to 293 cells or PER.C6® cells. In one embodiment of the invention, the adenoviral vector will further comprise a passenger transgene.

Another aspect of the present invention is a phage-display library of recombinant phage, wherein each recombinant phage displays on its outer surface a fusion protein which comprises a phage coat protein fused to a modified knob domain of an adenovirus fiber protein. The modified fiber knob, including but not limited to an Ad5 fiber knob domain, contains a peptide ligand comprising a core amino acid sequence of 14 residue positions wherein residue positions one, two and thirteen are Xaa residues, preferably tyrosine (Tyr), tryptophan (Trp), or phenylalanine (Phe); residue positions three and twelve are cysteine (Cys) residues; residue positions four through eleven are Xaa residues, preferably glycine (Gly), serine (Ser), or valine (Val); and, residue position fourteen is an Xaa residue, preferably proline (Pro). A portion of the modified fiber knobs contain a peptide ligand for a cell surface binding site other than CAR. The core amino acid sequence may be deleted by one or more residues at any residue position within the sequence, except at the fixed Cys residues at position three and position twelve. It is preferable that the region of the core amino acid sequence located between the fixed Cys residues comprises at least two amino acid residues. Additionally, up to 10 amino acid residues may be added between residue position three and residue position twelve. The amino acid sequence of the peptide ligand does not comprise a consecutive Arg-Gly-Asp (RGD) sequence between residue positions three and twelve, and the peptide ligand does not consist of the amino acid sequence as disclosed in SEQ ID NO:46.

Another embodiment of the present invention is a phage-display library comprising recombinant phage, each displaying on its outer surface a fusion protein which comprises a phage coat protein fused to an adenovirus fiber knob containing at least one of the variety of peptide ligands diagrammed in FIG. 13. Thus, included within said library are modified fiber knobs, including but not limited to modified Ad5 fiber knobs, which contain a peptide ligand for a cell surface binding site other than CAR comprising a core amino acid sequence of 14 residue positions, wherein residue positions one, two and thirteen are Xaa residues, preferably tyrosine (Tyr), tryptophan (Trp), or phenylalanine (Phe); residue positions three and twelve are cysteine (Cys) residues; residue positions four through eleven are Xaa residues, preferably glycine (Gly), serine (Ser), or valine (Val); and, residue position fourteen is an Xaa residue, preferably proline (Pro). The core amino acid sequence may be deleted by one or more residues at any residue position within the sequence, except at the Cys residues at position three and position twelve In this embodiment, the amino acid sequence of the peptide ligand does not comprise a consecutive Arg-Gly-Asp (RGD)

sequence between residue positions three and twelve, and the peptide ligand does not consist of the amino acid sequence as disclosed in SEQ ID NO:46.

As recited above, a portion of the modified fiber knobs contained within a phage-display library of the present invention, including but not limited to modified Ad5 fiber knobs, contain peptide ligands for cell surface binding sites other than CAR. The fiber knob contained within the phage-display library can be further modified to abolish wild-type cell surface binding. In one embodiment, the modified fiber knob displayed in the phage library comprises a peptide ligand as described herein which is inserted within an exposed loop domain of the knob, including but not limited to the HI loop domain. In one embodiment, the peptide ligand can be inserted between amino acid residue 546 and amino acid residue 547 located within the fiber knob of the Ad5 fiber protein.

In a further embodiment of the invention, the phage-display libraries described herein are displayed on bacteriophage λ, wherein the modified fiber knob is fused to the major head D protein of λ phage. The phage-display libraries of the present invention overcome the limitations of prior phage-display peptide libraries used to identify peptide ligands possessing an altered binding specificity when incorporated into adenovirus fibers because the candidate peptide ligands are expressed within a functional fiber knob in the phage-display system. By using the phage-display system of the present invention, the peptide ligands are surveyed for the ability to bind a cell surface attachment site other than CAR in the fiber knob context.

The present invention further relates to a method for identifying a peptide ligand for a cell specific binding site other than CAR which comprises (a) providing a phage-display library characterized by the above description, and (b) screening said library on either CAR-negative or CAR-positive cells. In one embodiment, a phage-display library of the present invention is screened on CAR-negative NIH-3T3 cells.

The present invention also relates to methods of transducing a cell and/or tissue with a recombinant adenovirus described in this specification. By using a recombinant adenovirus as described herein to transduce cells/tissues, both the ability and efficiency of adenovirus infectivity increases. In one embodiment, these methods comprise transducing cells that have little or no expression of CAR and are refractory to Ad5 infection with a recombinant adenovirus of the present invention. Cells and/or tissues that may be transduced with a recombinant adenovirus of the present invention include, but are not limited to, synoviocytes, smooth muscle cells, endothelial cells, cancer cells, primary tumors, dendritic cells, skeletal muscle, melanocytes and murine melanoma cells. Another embodiment includes a method of transducing immature dendritic cells, including but not limited to those of mouse or human origin, as well as murine skeletal muscle and human primary melanocytes, with a recombinant adenovirus of the present invention.

"Substantially free from other nucleic acids" means at least 90%, preferably 95%, more preferably 99%, and even more preferably 99.9%, free of other nucleic acids. As used interchangeably, the terms "substantially free from other nucleic acids," "substantially purified," "isolated nucleic acid" or "purified nucleic acid" also refer to DNA molecules which comprise a coding region for a modified adenovirus fiber protein of the present invention that has been purified away from other cellular components. Thus, a DNA preparation of a modified adenovirus fiber protein that is substantially free from other nucleic acids will contain, as a percent of its total nucleic acid, no more than 10%, preferably no more than 5%, more preferably no more than 1%, and even more preferably no more than 0.1%, of non-modified adenovirus fiber protein nucleic acids. Whether a given DNA preparation of a modified adenovirus fiber protein is substantially free from other nucleic acids can be determined by such conventional techniques of assessing nucleic acid purity as, e.g., agarose gel electrophoresis combined with appropriate staining methods, e.g., ethidium bromide staining, or by sequencing.

"Substantially free from other proteins" or "substantially purified" means at least 90%, preferably 95%, more preferably 99%, and even more preferably 99.9%, free of other proteins. Thus, a modified adenovirus fiber protein preparation that is substantially free from other proteins will contain, as a percent of its total protein, no more than 10%, preferably no more than 5%, more preferably no more than 1%, and even more preferably no more than 0.1%, of non-modified adenovirus fiber proteins. Whether a given modified adenovirus fiber protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting.

As used herein, "Ad5" refers to adenovirus serotype 5.

As used herein, "CAR" refers to the coxsackievirus and adenovirus receptor.

As used herein, "Xaa" refers to the three letter abbreviation representing any of the 20 amino acid residues.

As used herein, "variable amino acid residue position" or "variable residue position" refers to an amino acid residue position that may contain any of the 20 amino acid residues.

As used herein, "binding moiety" refers to a molecule that is exposed on the surface of the adenovirus which is able to bind to a molecule on a target cell.

As used herein, "target cell" refers to the cell to which a recombinant adenovirus can bind using its binding moiety.

As used herein, "peptide ligand" incorporated within an adenovirus fiber protein refers to a heterologous (i.e., not typically contained within the adenovirus fiber protein) polypeptide that has the ability to bind to a cell surface binding site on a target cell.

As used herein, "RGD" refers to a consecutive Arg-Gly-Asp amino acid sequence.

As used herein, "vector" refers to some means by which DNA fragments can be introduced into a host organism or host tissue, including but not limited to plasmids, virus (including adenovirus), bacteriophages and cosmids.

As used herein, "first generation," as used in reference to adenoviral vectors, describes said adenoviral vectors that are replication-defective. First generation adenovirus vectors typically have a deleted or inactivated E1 gene region, and preferably have a deleted or inactivated E3 gene region.

As used herein, "passenger transgene" is any gene which is not typically present in and is subcloned into a vector (e.g., an adenoviral vector) according to the present invention.

As used herein, "wt" refers to wild-type.

As used herein, "vp" refers to viral particles.

As used herein, "RPE" refers to R-phycoerythrin.

BRIEF DESCRIPTION OF THE DRAWINGS

FIG. 1 shows the amino acid sequence of a modified Ad5 fiber protein, Ad5 fiber-L1, as set forth in SEQ ID NO:1. This sequence contains the L1 peptide ligand (SEQ ID NO:13) within the HI loop of the fiber knob between amino acid residues 546 and 547 of the fiber protein. The knob domain is underlined. The L1 peptide ligand sequence is in italics. The amino acid residues added to the wild-type Ad5 fiber sequence to facilitate insertion of the L1 peptide ligand are in lowercase.

FIG. 2 shows the amino acid sequence of a modified Ad5 fiber protein, Ad5 fiber-L16, as set forth in SEQ ID NO:2. This sequence contains the L16 peptide ligand (SEQ ID NO:14) within the HI loop of the fiber knob between amino acid residues 546 and 547 of the fiber protein. The knob domain is underlined. The L16 peptide ligand sequence is in italics. The amino acid residues added to the wild-type Ad5 fiber sequence to facilitate insertion of the L16 peptide ligand are in lowercase.

FIG. 3 shows the amino acid sequence of a modified Ad5 fiber protein, Ad5 fiber-L33, as set forth in SEQ ID NO:3. This sequence contains the L33 peptide ligand (SEQ ID NO:15) within the HI loop of the fiber knob between amino acid residues 546 and 547 of the fiber protein. The knob domain is underlined. The L33 peptide ligand sequence is in italics. The amino acid residues added to the wild-type Ad5 fiber sequence to facilitate insertion of the L33 peptide ligand are in lowercase.

FIG. 4 shows the nucleotide sequence, as set forth in SEQ ID NO:4, encoding the Ad5 fiber-L1 protein as shown in FIG. 1, and as set forth in SEQ ID NO:1. This sequence represents the Ad5 fiber gene containing within what corresponds to the HI loop of the fiber knob the nucleic acid sequence encoding the L1 peptide ligand. The region encoding the knob is underlined. The nucleic acid sequence encoding the L1 peptide ligand is in italics. The additional sequence variation, seen in lowercase, account for an engineered restriction site used to facilitate insertion of the nucleotide sequence encoding L1 into the wild-type fiber, and acts to maintain the wild-type fiber amino acid sequence.

FIG. 5 shows the nucleotide sequence, as set forth in SEQ ID NO:5, encoding the Ad5 fiber-L16 protein as shown in FIG. 2, and as set forth in SEQ ID NO:2. This sequence represents the Ad5 fiber gene containing within what corresponds to the HI loop of the fiber knob the nucleic acid sequence encoding the L16 peptide ligand. The region encoding the knob is underlined. The nucleic acid sequence encoding the L16 peptide ligand is in italics. The additional sequence variation, seen in lowercase, account for an engineered restriction site used to facilitate insertion of the nucleotide sequence encoding L16 into the wild-type fiber, and acts to maintain the wild-type fiber amino acid sequence.

FIG. 6 shows the nucleotide sequence, as set forth in SEQ ID NO:6, encoding the Ad5 fiber-L33 protein as shown in FIG. 3, and as set forth in SEQ ID NO:3. This sequence represents the Ad5 fiber gene containing within what corresponds to the HI loop of the fiber knob the nucleic acid sequence encoding the L33 peptide ligand. The region encoding the knob is underlined. The nucleic acid sequence encoding the L33 peptide ligand is in italics. The additional sequence variation, seen in lowercase, account for an engineered restriction site used to facilitate insertion of the nucleotide sequence encoding L33 into the wild-type fiber, and acts to maintain the wild-type fiber amino acid sequence.

FIG. 7 shows the amino acid sequence of a modified Ad5 fiber-L1 protein, Ad5 fiberΔ-L1, as set forth in SEQ ID NO:7. This sequence harbors the deletion of amino acid residues TAYT (SEQ ID NO:45) from amino acid residue 489 to 492 of the Ad5 fiber protein, abrogating CAR binding. In addition, it contains the L1 peptide ligand (SEQ ID NO:13) within the HI loop of the fiber knob between amino acid residues 546 and 547. The knob domain is underlined. The amino acids flanking the deletion are double underlined. The L1 peptide ligand sequence is in italics. The additional sequence variation, seen in lowercase, account for an engineered restriction site used to facilitate insertion of the nucleotide sequence encoding L1 into the wild-type fiber, and acts to maintain the wild-type fiber amino acid sequence.

FIG. 8 shows the amino acid sequence of a modified Ads fiber-L16 protein, Ad5 fiberΔ-L16, as set forth in SEQ ID NO:8. This sequence harbors the deletion of amino acid residues TAYT (SEQ ID NO:45) from amino acid residue 489 to 492 of the Ad5 fiber protein, abrogating CAR binding. In addition, it contains the L16 peptide ligand (SEQ ID NO:14) within the HI loop of the fiber knob between amino acid residues 546 and 547. The knob domain is underlined. The amino acids flanking the deletion are double underlined. The L16 peptide ligand sequence is in italics. The additional sequence variation, seen in lowercase, account for an engineered restriction site used to facilitate insertion of the nucleotide sequence encoding L16 into the wild-type fiber, and acts to maintain the wild-type fiber amino acid sequence.

FIG. 9 shows the amino acid sequence of a modified Ad5 fiber-L33 protein, Ad5 fiberΔ-L33, as set forth in SEQ ID NO:9. This sequence harbors the deletion of amino acid residues TAYT (SEQ ID NO:45) from amino acid residue 489 to 492 of the Ad5 fiber protein, abrogating CAR binding. In addition, it contains the L33 peptide ligand (SEQ ID NO:15) within the HI loop of the fiber knob between amino acid residues 546 and 547. The knob domain is underlined. The amino acids flanking the deletion are double underlined. The L33 peptide ligand sequence is in italics. The additional sequence variation, seen in lowercase, account for an engineered restriction site used to facilitate insertion of the nucleotide sequence encoding L33 into the wild-type fiber, and acts to maintain the wild-type fiber amino acid sequence.

FIG. 10 shows the nucleotide sequence, as set forth in SEQ ID NO:10, encoding the Ad5 fiberΔ-L1 protein of the present invention. This sequence harbors the deletion of the nucleotides 1465 through 1476 (ACAGCCTATACA; SEQ ID NO:47) of the nucleic acid sequence encoding the wild-type. Ad5 fiber protein. This nucleotide deletion corresponds to the deletion of amino acid residues TAYT (SEQ ID NO:45), described herein, which abrogates Ad5 fiber protein binding to CAR. In addition, this sequence contains the nucleic acid sequence encoding the L1 peptide ligand within the HI loop of the fiber knob. The knob domain is underlined. The nucleotide codons flanking the deletion are double underlined. The nucleic acid sequence encoding the L1 peptide ligand is in italics. The additional sequence variation, seen in lowercase, account for an engineered restriction site used to facilitate insertion of the nucleotide sequence encoding L1 into the wild-type fiber, and acts to maintain the wild-type fiber amino acid sequence.

FIG. 11 shows the nucleotide sequence, as set forth in SEQ ID NO:11, encoding the Ad5 fiberΔ-L16 protein of the present invention. This sequence harbors the deletion of the nucleotides 1465 through 1476 (ACAGCCTATACA; SEQ ID NO:47) of the nucleic acid sequence encoding the wild-type Ad5 fiber protein. This nucleotide deletion corresponds to the deletion of amino acid residues TAYT (SEQ ID NO:45), described herein, which abrogates Ad5 fiber protein binding to CAR. In addition, this sequence contains the nucleic acid sequence encoding the L16 peptide ligand within the HI loop of the fiber knob. The knob domain is underlined. The nucleotide codons flanking the deletion are double underlined. The nucleic acid sequence encoding the L16 peptide ligand is in italics. The additional sequence variation, seen in lowercase, account for an engineered restriction site used to facilitate insertion of the nucleotide sequence encoding L16 into the wild-type fiber, and acts to maintain the wild-type fiber amino acid sequence.

FIG. 12 shows the nucleotide sequence, as set forth in SEQ ID NO:12, encoding the Ad5 fiberΔ-L33 protein of the present invention. This sequence harbors the deletion of the nucleotides 1465 through 1476 (ACAGCCTATACA; SEQ ID NO:47) of the nucleic acid sequence encoding the wild-type Ad5 fiber protein. This nucleotide deletion corresponds to the deletion of amino acid residues TAYT (SEQ ID NO:45), described herein, which abrogates Ad5 fiber protein binding to CAR. In addition, this sequence contains the nucleic acid sequence encoding the L33 peptide ligand within the HI loop of the fiber knob. The knob domain is underlined. The nucleotide codons flanking the deletion are double underlined. The nucleic acid sequence encoding the L33 peptide ligand is in italics. The additional sequence variation, seen in lowercase, account for an engineered restriction site used to facilitate insertion of the nucleotide sequence encoding L33 into the wild-type fiber, and acts to maintain the wild-type fiber amino acid sequence.

The bottom panel describes the composition of the oligonucleotide mixture, encoding the candidate peptide ligands, used to generate the knobΔ-14aa.cys library. The peptides were generated with a resin splitting technology. The numbers at the bottom of the panel indicate the 14 potential amino acid residue positions of the candidate peptide ligands that are inserted within knobΔ-L0. Within each bar, the shaded box represents the percentage of the individual codon of the codon pool used to generate that amino acid residue position. Attached to the shaded box are two stacked boxes showing the sequence of that individual codon and the amino acid residue it encodes. For example, at positions 1 and 2, 35% of the individual codon sequences used to generated the amino acid residues for those positions have an NNS nucleotide sequence. An "N" within the codon sequence denotes any of the four nucleotides: adenine (A), cytosine (C), thymine (T), or guanine (G). An "S" refers to an equimolar frequency of C and G nucleotides. Thus, NNS represents any amino acid residue, as depicted by the "Xxx" in the upper box of the bar. Alternatively, 20% of the individual codon sequences used to generate the amino acid residues in those positions have a TTC nucleotide sequence, encoding a phenylalanine residue (Phe). To add further variation in the library, 5% of the codon sequences used to generate each potential amino acid residue position, except those coding for the fixed cysteines (Cys) at positions 3 and 12, were deleted. The nucleotide and corresponding amino acid sequences flanking the 14 potential amino acid residue positions represent the location into which the synthesized peptide ligands are inserted within knobΔ-L0. The peptide ligands are inserted within knobΔ-L0 using the newly engineered SpeI and NotI restriction sites. After insertion of the candidate peptide ligands, the added Gly (G) residue seen in knobΔ-L0 between amino acid residues 546 and 547 of the Ad5 fiber protein is removed. The newly added Ser residue (S) flanks the amino-terminus of the inserted peptide ligand, and the newly added Ala-Ala-Ala (AAA) residues flank the carboxy-terminus.

FIG. 14 shows the structure of the λ-Ad5knob expression cassette. The nucleotide sequence (SEQ ID NO:18), and the corresponding amino acid sequence (SEQ ID NO:19), of the region between the D protein of lambda phage and the knob region of the Ad5 gene is detailed. A linker of 16 Gly-Ser (GS) repeats, a ribosome binding site (RBS) sequence and amber codon sequences are located between the carboxy-terminus of the λD protein and the amino-terminus of the knob protein. Numbers refer to position of amino acid residues in the wild type λD and fiber amino acid residues.

Figure 15:
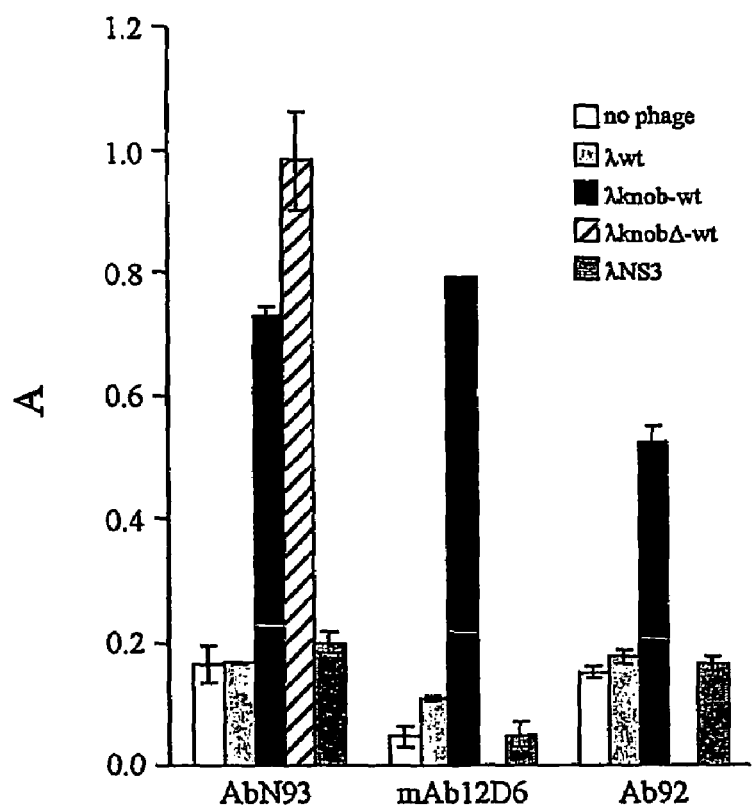

FIG. 15 demonstrates the display of trimeric Ad5 knob domain on λ capsid. The binding of mouse mAb12D6 and human AbN93 (both specific for the trimeric form of Ad5 knob), as well as Ab92 antibodies (which detect both the monomeric and the trimeric structure), to the proteins indicated was assessed by phage-ELISA. Results are expressed as $A=A_{405nm}-A_{620nm}$. Each point represents the mean of triplicate determinations. Standard deviation for each value is reported.

Figure 16:
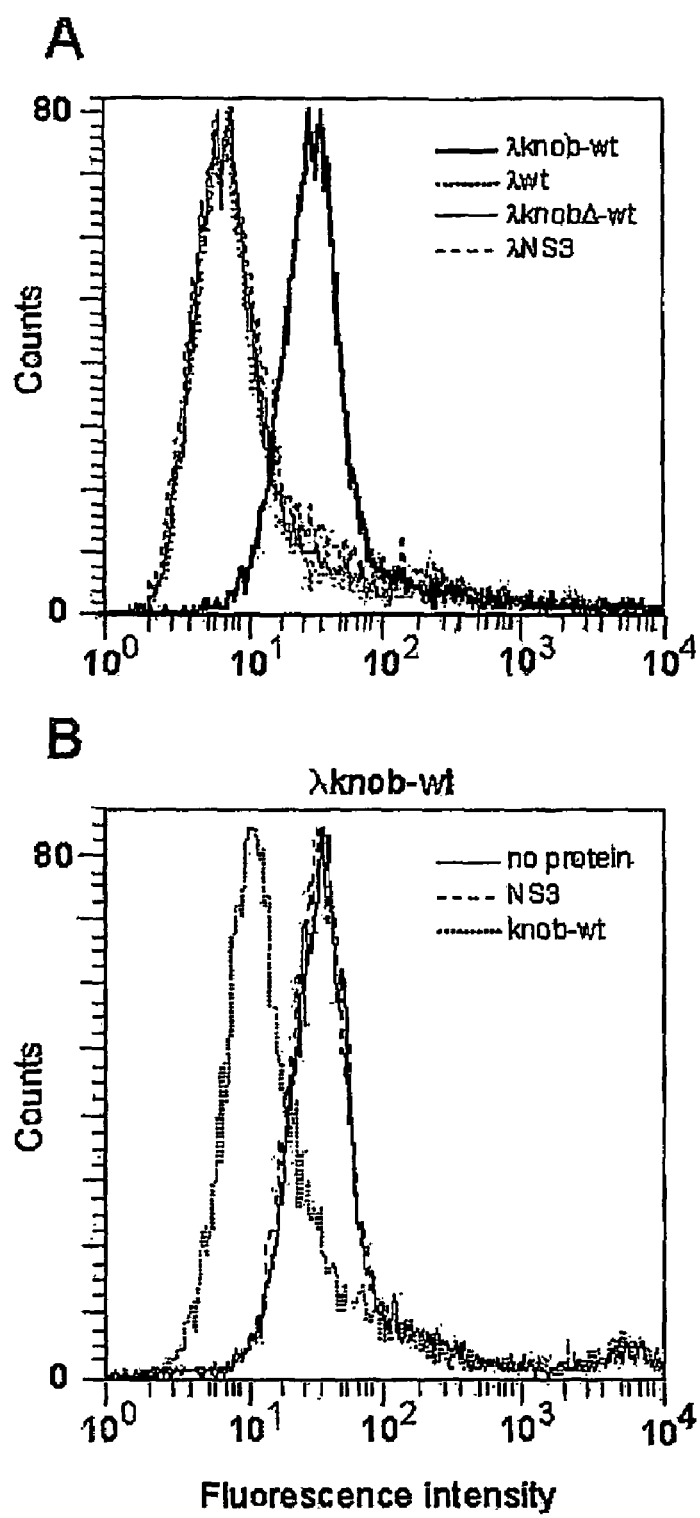

FIG. 16A-B show the FACS analysis of binding of λ-displayed Ad5 knob to CAR-positive 911 cells. (A) Binding of phage-borne Ad5 knob-wt and Ad5 knobΔ-wt to 911 cells. Negative controls (λwt and λNS3) are included. (B) Binding of λknob-wt to 911 cells in the presence of knob-wt protein. Control reactions in the absence of protein or in the presence of λNS3 are also reported.

Figure 17:
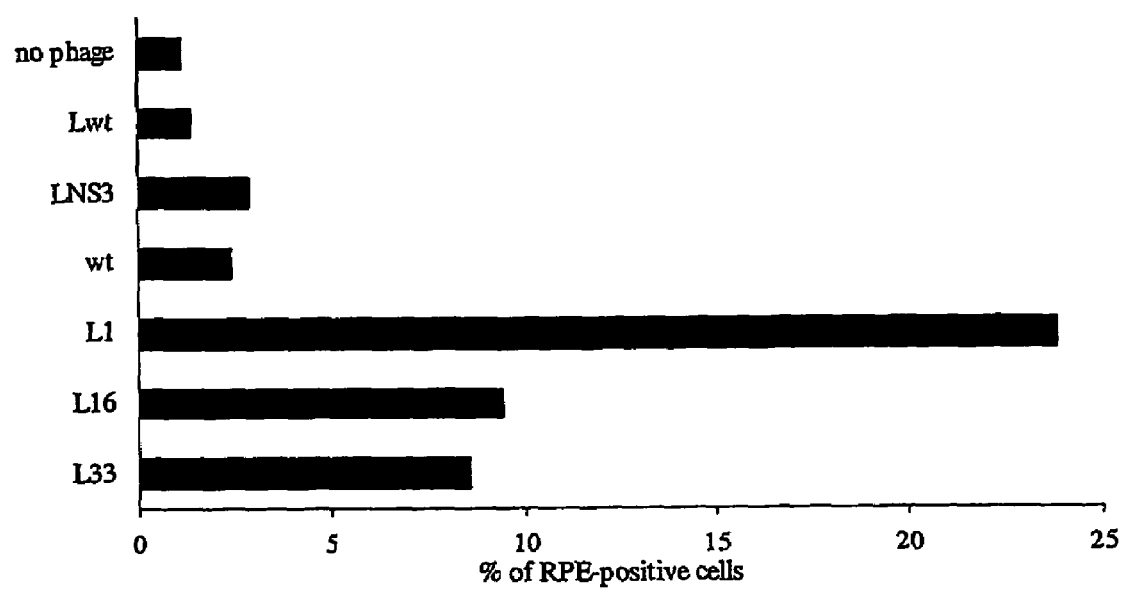

FIG. 17 shows that phage lysates from λknobΔ-L1 (L1), λknobΔ-L16 (L16) and λknobΔ-L33 (L33) bind NIH3T3 cells. Binding of the λ phage to NIH3T3 cells was assayed by flow cytometric analysis. Data are reported as the percentage of RPE-labeled population.

FIG. 18 shows the amino acid sequences of novel peptide ligands of the present invention. The amino acid residues making up the peptide ligands are reported in single letter code. The numbers at the top of the panel refer to the core amino acid sequence of the peptide ligands, made up of 14 potential amino acid residue positions.

Figure 19:
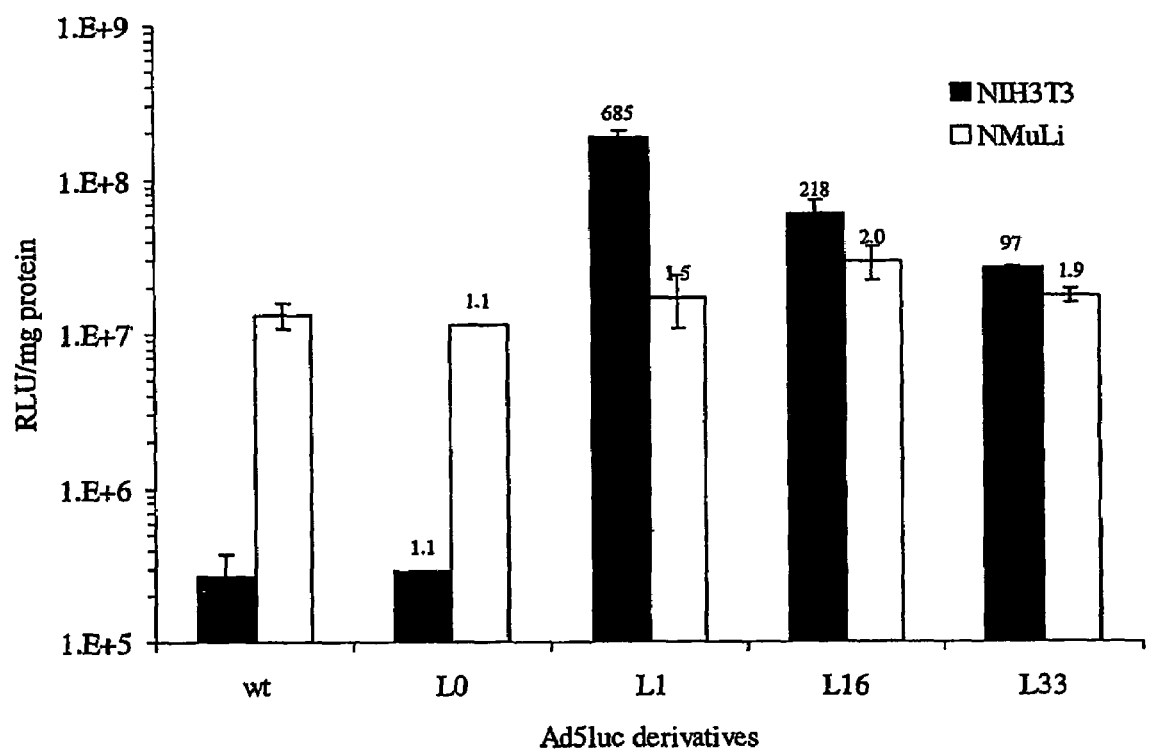

FIG. 19 shows the gene transfer efficiency of the Ad5luc-LX adenovirus derivatives (Ad5luc-L1, Ad5luc-L16 and Ad5luc-L33), in comparison to both wild-type Ad5luc and Ad5luc-L0, in NIH3T3 and NMuLi cells. NIH3T3 or NMuLi cells were infected with the indicated virus at a multiplicity of infection (moi) of 50. Luciferase activity is expressed as relative light units (RLU) per mg of protein. Each point in the display items represents the mean of triplicate determinations, and the standard deviation for each value is reported. Values on top of the histograms refer to the ratio between the activity of the virus and those of parent Ad5luc-wt.

Figure 20:
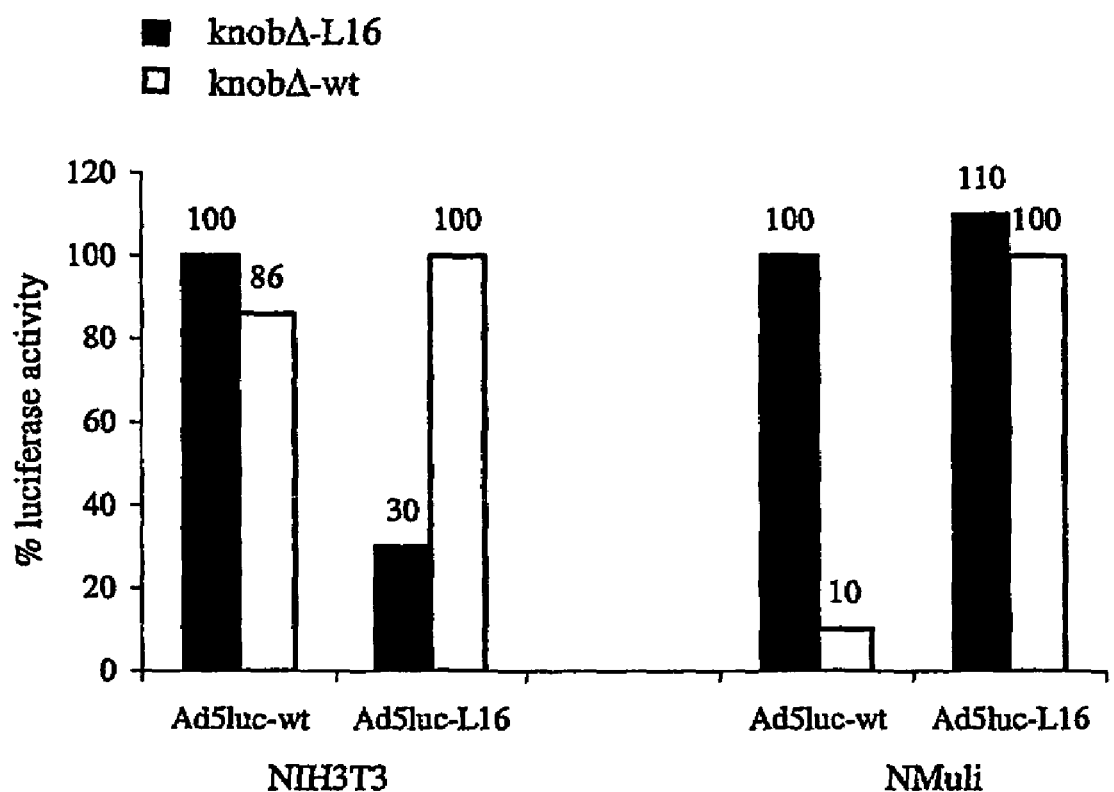

FIG. 20 shows the competition of Ad5luc-L16 infection with recombinant knob proteins, knobΔ-L16 and knob-wt, in NIH3T3 cells or NMuLi cells. Results are reported on top of the histograms and are expressed as the percentage of luciferase activity of cells in the presence of control protein (knobΔ-L16 for Ad5luc-wt and knob-wt for Ad5luc-L16).

Figure 21:
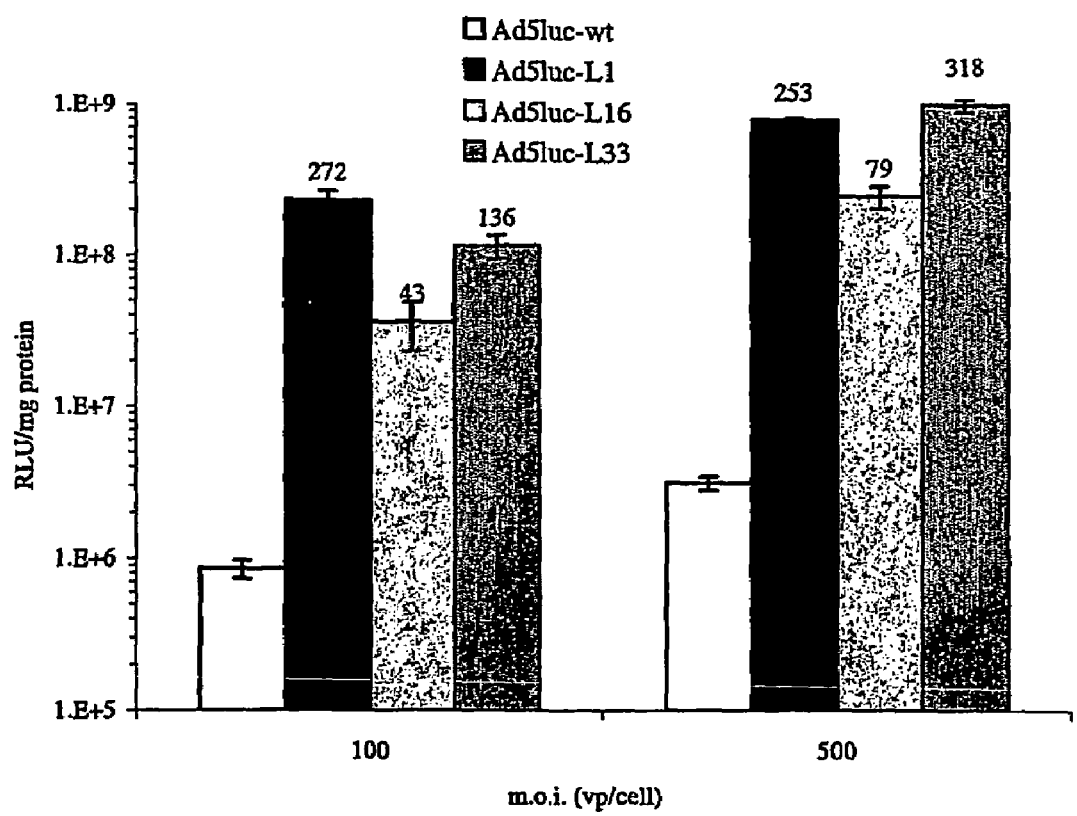

FIG. 21 shows the infection of CHO cells with the Ad5luc-LX derivatives (Ad5luc-L1, Ad5luc-L16 and Ad5luc-L33). CHO cells were infected with Ad5luc derivatives at different moi. Luciferase activity is expressed as relative light units (RLU) per mg of protein. Each point in the display items represents the mean of triplicate determinations, and the standard deviation for each value is reported. Values on top of the histograms refer to the ratio between the activity of the virus and those of parent Ad5luc-wt.

Figure 22:
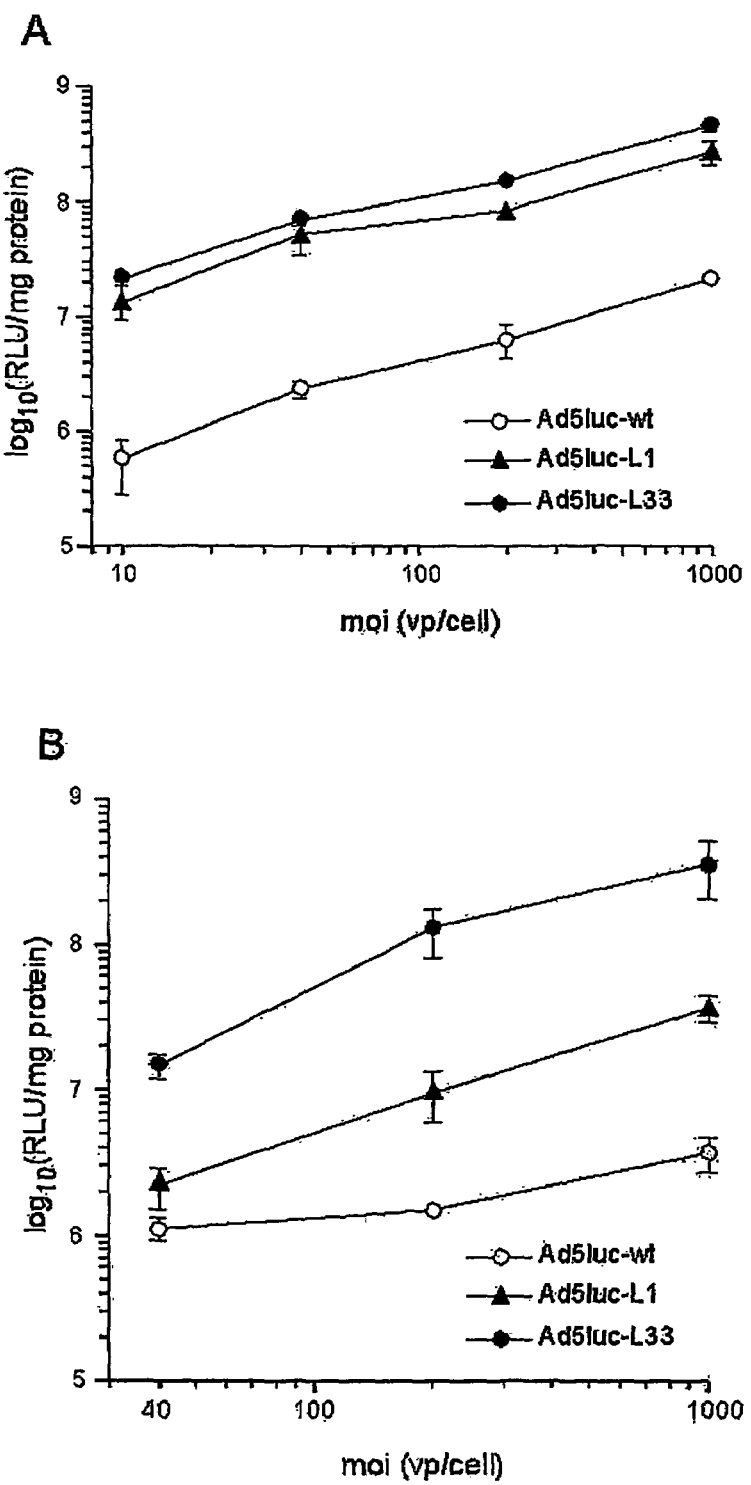

FIG. 22 shows that Ad5luc-LX derivatives efficiently transduce dendritic cells (DC). (A) Infection of bone marrow derived mouse immature DC. (B) Infection of monocyte-derived human immature DC. Luciferase activity is expressed as relative light units (RLU) per mg of protein. Each point in the display items represents the mean of triplicate determinations, and the standard deviation for each value is reported.

Figure 23:
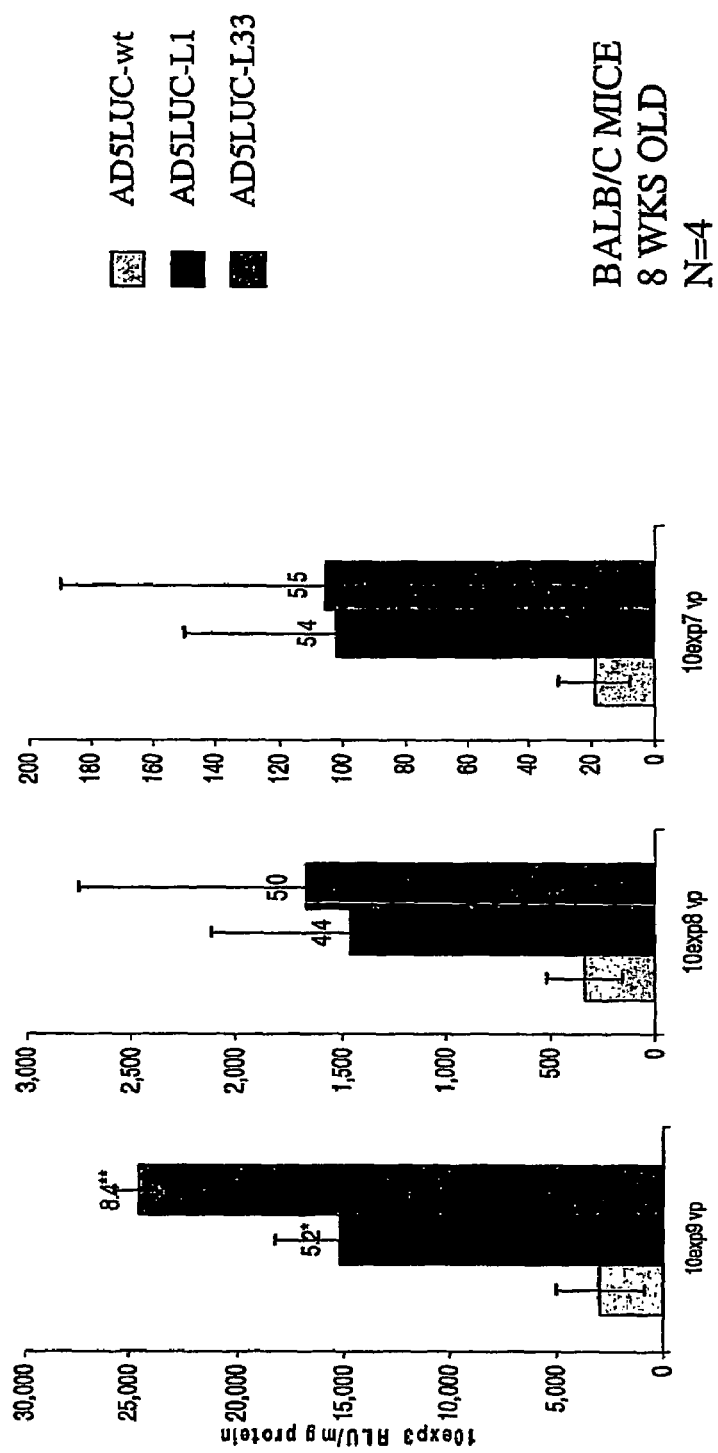

FIG. 23 shows that Ad5luc-LX derivatives exhibit increased muscle transduction in vivo. Mice were injected in the quadriceps with $^-10^9$, $10^8$ or $10^7$ viral particles (vp) of wild-type or Ad5luc-LX derivatives (L1, L33). Forty-eight hours after the infection, mice were sacrificed, muscles were removed and luciferase activity measured. Luciferase activity is expressed as relative light units (RLU) per mg of protein. Standard deviation for each value is reported.

Figure 24:
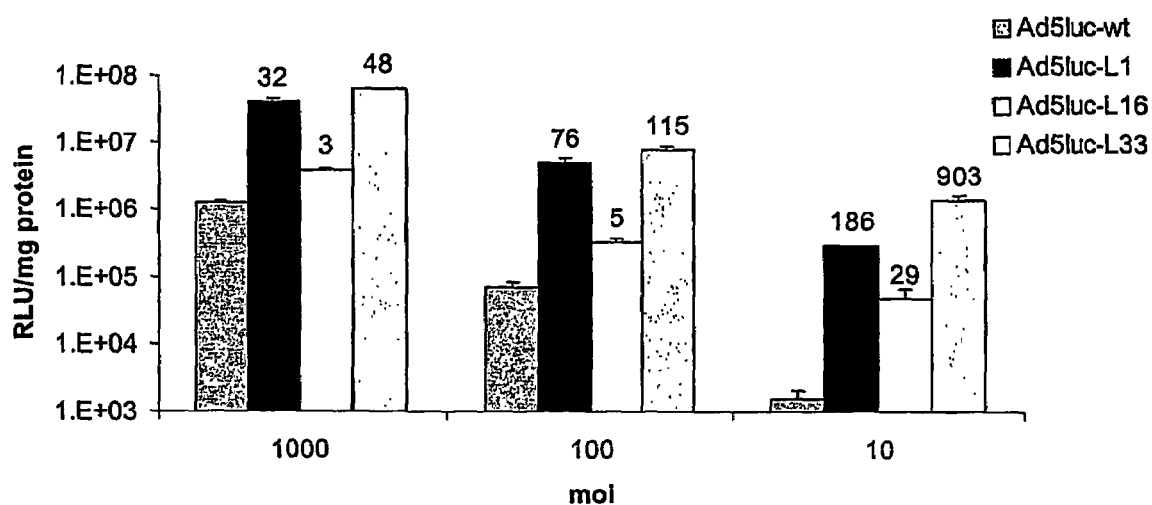

FIG. 24 shows the infection of human primary melanocytes with Ad5luc-LX derivatives (L1, L16 and L33). Cells were infected with Ad5luc derivatives at different moi. Luciferase activity is expressed as relative light units (RLU) per mg of protein. Each point in the display items represents the mean of triplicate determinations, and the standard deviation for each value is reported. Values on top of the histograms refer to the ratio between the activity of the virus and those of parent Ad5luc-wt.

DETAILED DESCRIPTION OF THE INVENTION

The present invention relates to a recombinant adenovirus having a modified fiber protein which comprises a peptide ligand for a cell surface binding site other than CAR. The modified fiber protein enables the adenovirus to attain a broadened tropism, thus providing a higher activity and functionality of the adenovirus gene therapy system. The peptide ligand of said modified fiber protein comprises a core amino acid sequence representing 14 potential residue positions which may or may not contain an amino acid residue. In one embodiment, the core amino acid sequence contains Xaa residues at positions one, two and thirteen, preferably tyrosine (Tyr), tryptophan (Trp), or phenylalanine (Phe); cysteine (Cys) residues at positions three and twelve; Xaa residues at positions four through eleven, preferably glycine (Gly), serine (Ser), or valine (Val); and, an Xaa residue at position fourteen, preferably proline (Pro). Xaa is a three letter abbreviation symbolizing that any of the 20 amino acid residues may be represented in that particular residue position. Thus, a recombinant adenovirus of this embodiment contains a modified fiber protein comprising a peptide ligand where only two residue positions, out of the 14 potential residue positions, are fixed amino acid residues: the Cys residues at positions three and twelve. The amino acid residue positions that are variable in this embodiment, positions one, two, four through eleven, thirteen and fourteen, contain preferences for particular amino acid residues. However, the amino acid sequence of the peptide ligand does not comprise a consecutive Arg-Gly-Asp (RGD) amino acid sequence in its flexible loop domain located between the fixed Cys residues at positions three and twelve. Additionally, the peptide ligand does not consist of the amino acid sequence as disclosed in SEQ ID NO:46.

Amino acid preferences at the variable residue positions of the core amino acid sequence are created as a result of the method in which the pool of peptide ligands used to modify the adenovirus fiber proteins of the present invention is generated. As generally described in Example 3 and depicted in FIG. 13, the oligonucleotides that encode the peptide ligands of the present invention are synthesized by a resin-splitting methodology. Using this methodology, nucleic acid codons encoding a single amino acid residue are sequentially added to generate a specific oligonucleotide sequence of a desired length. For example, all of the peptide ligands of the present invention contain Cys residues at residue position three and twelve; thus, codons that only encode Cys are used when synthesizing the nucleic acid sequence to encode the third and twelfth residue positions. To generate a peptide ligand that has the potential of having any amino acid at a particular residue position (i.e., a variable residue position), nucleic acid codons that encode each amino acid residue are utilized when synthesizing that particular residue position. A variable residue position can favor a particular amino acid, or groups of amino acids, by increasing the percentage of codon encoding that particular amino acid, or groups of amino acids, within the codon pool when synthesizing that particular residue position. By using this method, the core amino acid sequences of the peptide ligands described in the present invention are created to contain variable residue positions that favor particular amino acids. Tyrosine, tryptophan, and phenylalanine residues are favored at certain positions because their aromatic ring structures facilitate interactions with hydrophobic receptor structures. Due to its tendency to adopt an extended structure, proline is favored at residue position fourteen of the peptide ligands of the present invention to increase accessibility of the inserted peptide ligand. Of the remaining variable residue positions, generally located in the middle of the core sequence (i.e., the loop domain of the peptide ligand), amino acids that help to increase loop flexibility are favored. Thus, these residue positions are biased to contain amino acids with small lateral chains, such as glycine, serine and valine.

The core amino acid sequence of the peptide ligand of the present invention may be deleted by one or more residues at any residue position within the core sequence, except at the fixed residue positions. Thus, some of the 14 potential residue positions of the core sequence will not contain an amino acid residue. A deletion can only occur at the variable amino acid residue positions (i.e., those characterized by an Xaa residue). Thus, if the only fixed amino acid residues are the Cys residues located at residue positions three and twelve, as described herein, any of the remaining 12 potential residue positions may lack an amino acid residue. It is preferable that the region of the core amino acid sequence located between the fixed Cys residues at position three and position twelve comprises at least two amino acid residues. The number of empty amino acid residue positions varies according to the frequency at which deletion of codon is introduced at each position during oligonucleotide synthesis. The deletion of an amino acid residue within the core sequence does not change the numbering system of the 14 potential amino acid residue positions. For example, if the fixed amino acid residues are located at position number three and twelve, but the amino acid at position two has been deleted such that it lacks an amino acid residue, the numbering of the fixed amino acid residues remains the same. Thus, in this example, the fixed amino acids are still located at residue position number three and twelve, rather than being shifted to residue position number two and eleven.

Additionally, the present invention contemplates that up to 10 amino acid residues may be added between the fixed residue positions of the peptide ligand core sequence. The fixed residues are located near the ends of the core amino acid sequence; thus, the addition of amino acid residues between the fixed residues increases the length of the flexible loop domain of the peptide ligand sequence. Accordingly, the largest possible peptide ligand is 24 amino acids in length. With the addition of amino acid residues in this region of the core sequence, the numbering of the 14 potential amino acid residue positions does not change. For example, if the fixed residues are located at residue position number three and twelve, and two amino acid residues are added between the fixed residue positions, the numbering of the fixed amino acid residues remains the same. Thus, in this example, the fixed amino acids are still located at residue position number three and twelve, rather than being shifted to residue position number three and fourteen. The two amino acids that are added within the loop domain of the peptide ligand are numbered using the prime (') symbol designation. For example, if one of the amino acids is added between residue positions four and five, and the other is added between residue positions seven and eight, the two newly added amino acids will be contained with residue positions four prime (4') and seven prime (7'), respectively. More than one amino acid can be added between the amino acid residue positions located within the loop domain.

The present invention further relates to a recombinant adenovirus with a modified fiber protein which comprises a peptide ligand for a cell surface binding site other than CAR, wherein the peptide ligand comprises a core amino acid sequence of 14 potential residue positions such that 3 of the 14 potential amino acid residue positions are fixed with a particular amino acid residue. In this embodiment, residue positions one and thirteen are Xaa residues, preferably tyrosine (Tyr), tryptophan (Trp), or phenylalanine (Phe); residue position two is a phenylalanine (Phe) residue; residue positions three and twelve are cysteine (Cys) residues; residue positions four through eleven are Xaa residues, preferably glycine (Gly), serine (Ser), or valine (Val); and, residue position fourteen is an Xaa residue, preferably proline (Pro). Thus, the fixed amino acid residue positions are located at positions two, three, and twelve, containing Phe, Cys, and Cys residues, respectively. The core amino acid sequences of this embodiment, including the preferable amino acid residues located at the variable residue positions, are generated as described in the previous embodiment. The core amino acid sequence may be deleted by one or more residues at the variable amino acid residue positions (i.e., at all residue positions except positions two, three and twelve). It is preferable that the region of the core amino acid sequence located between the fixed Cys residues comprises at least two amino acid residues. An addition of up to 10 amino acid residues may be tolerated within the flexible loop domain of the peptide ligands of the instant embodiment. The loop domain is located between the fixed Cys residues at positions the and twelve, and thus, up to 10 amino acid residues can be added between said amino acid residue positions. As described in this specification, the numbering of the amino acid residues within the core amino acid sequence remains the same in the event of a deletion and/or addition of amino acids to the core sequence. The amino acid sequence of the peptide ligand does not comprise a consecutive Arg-Gly-Asp (RGD) sequence in the flexible loop domain located between the fixed Cys residues of the instant embodiment.

The present invention also relates to a recombinant adenovirus with a modified fiber protein which comprises a peptide ligand for a cell surface binding site other than CAR, wherein the peptide ligand comprises a core amino acid sequence of 14 potential residue positions such that 6 of the 14 potential amino acid residue positions are fixed with a particular amino acid residue. In this embodiment, residue positions one, two and thirteen are Xaa residues, preferably tyrosine (Tyr), tryptophan (Trp), or phenylalanine (Phe); residue positions three and twelve are cysteine (Cys) residues; residue positions four through seven are Xaa residues, preferably glycine (Gly), serine (Ser), or valine (Val); residue positions eight and nine are glycine (Gly) residues; residue positions ten and eleven are serine (Ser) residues; and, residue position fourteen is an Xaa residue, preferably proline (Pro). In the previous embodiments, each of the 8 potential amino acid residues making up the flexible loop domain of the peptide ligand (i.e., spanning and including residue positions four through eleven) contain an Xaa residue, preferably a Gly, Ser, or Val residue. In this embodiment, 4 of the 8 potential amino acid residues in the flexible loop domain are fixed: positions eight and nine are Gly residues, and positions ten and eleven are Ser residues. The core amino acid sequence may be deleted by one or more residues at the variable residue positions within the sequence including residue positions one, two, four through seven, thirteen and fourteen. Additionally, up to 10 amino acid residues may be added between the fixed residue positions at residue positions three and eight. The fixed amino acid residues located within the flexible loop domain at residue positions eight through eleven remain as four consecutive amino acids and are never separated by intervening, additional amino acids. The amino acid sequence of the peptide ligand does not comprise a consecutive Arg-Gly-Asp (RGD) sequence between the fixed residue positions located at residue positions three and eight.

The present invention further relates to a recombinant adenovirus with a modified fiber protein which comprises a peptide ligand for a cell surface binding site other than CAR, wherein the peptide ligand comprises a core amino acid sequence of 14 potential residue positions such that 7 of the 14 potential amino acid residue positions are fixed with a particular amino acid residue. In this embodiment, residue positions one and thirteen are Xaa residues, preferably tyrosine (Tyr), tryptophan (Trp), or phenylalanine (Phe); position two is a phenylalanine (Phe) residue; residue positions three and twelve are cysteine (Cys) residues; residue positions four through seven are Xaa residues, preferably glycine (Gly), serine (Ser), or valine (Val); residue positions eight and nine are glycine (Gly) residues; residue positions ten and eleven are serine (Ser) residues; and, residue position fourteen is an Xaa residue, preferably proline (Pro). As with the previous embodiment, 4 of the 8 potential amino acid residues located within the flexible loop domain of the peptide ligand are fixed: positions eight and nine are Gly residues; and positions ten and eleven are Ser residues. In this embodiment, the core amino acid sequence of the peptide ligand contains one additional fixed amino acid at residue position two, containing a Phe residue. The core amino acid sequence may be deleted by one or more residues at the variable residue positions within the sequence including residue positions one, four through seven, thirteen and fourteen. Additionally, up to 10 amino acid residues may be added between the fixed residue positions at residue positions three and eight. The fixed amino acid residues located within the flexible loop domain, residue positions eight through eleven, remain as four consecutive amino acids and are never separated by intervening, additional amino acids. The amino acid sequence of the peptide ligand does not comprise a consecutive Arg-Gly-Asp (RGD) sequence between the fixed residue positions located at residue position three and eight.

The present invention also relates to a recombinant adenovirus having a modified fiber protein comprising a peptide ligand for a cell surface binding site other than CAR, wherein said peptide ligand comprises the amino acid sequence selected from the group consisting of FCVASRGGSSCY (SEQ ID NO:13), FCKVVGGGSSCSP (SEQ ID NO:14) and FFCVSDGGGSSCP (SEQ ID NO:15).

The present invention is also directed to a recombinant adenovirus wherein, prior to modification, the adenovirus is of a first serotype; and after modification, at least a portion of the fiber protein of said first adenovirus serotype has been removed and replaced with the same or similar portion of a fiber protein from a second adenovirus serotype, wherein the fiber protein from the second adenovirus serotype has been modified as described in this specification. The portion of the fiber protein from the second adenovirus serotype which is used to replace the portion removed from the first adenovirus serotype fiber protein contains a peptide ligand as described in this specification. In this context, "a same or similar portion of a fiber protein from a second adenovirus serotype" means that the portion of the second adenovirus serotype fiber protein used to replace the portion removed from the first adenovirus serotype fiber protein is approximately the same size and consists of approximately the same protein domain(s) as the removed portion from the first adenovirus serotype fiber protein. Therefore, one embodiment of the present invention relates to a recombinant adenovirus wherein the fiber protein has been replaced by a modified fiber protein of an alternate serotype. In another embodiment, if the modified adenovirus fiber protein comprises a peptide ligand contained within its knob domain from one adenovirus serotype (as described further herein), the knob domain comprising the peptide ligand can be used to replace a wild-type knob domain of an alternative adenovirus serotype, as long as proper fiber trimerization is maintained. In particular, the present invention relates to a recombinant adenovirus of any serotype of human or non-human origin wherein the knob domain of the adenovirus is replaced with the knob domain of a modified Ad5 fiber knob as described in this specification. A recombinant adenovirus containing a chimeric viral genome, e.g., encoding a chimeric fiber protein as described herein, will be useful in gene therapy/gene vaccination prime-boost regimes to help prevent or limit host neutralization responses which may present upon re-administration of the respective viral vector.

The present invention further relates to a recombinant adenovirus containing a modified adenovirus fiber protein that is further modified to eliminate the native tropism of the adenovirus. The present invention also relates to a modified adenovirus fiber protein which is further modified as described above. For example, any modified CAR-recognizing adenovirus fiber protein disclosed herein can be further modified to abolish CAR binding of the modified protein. CAR binding of an adenovirus fiber protein can be ablated as a result of specific sequence modifications, as described in Roelvink et al., 1999, *Science* 286:1568-1571; hereby incorporated by reference. In one embodiment of the invention, a modified Ad5 fiber protein of the present invention is further modified to ablate CAR binding by deletion of a four-amino acid sequence TAYT (SEQ ID NO:45) located from amino acid residue 489 to amino acid residue 492 of the fiber protein. The inability of a recombinant adenovirus of the present invention to bind its wild-type cell surface binding site, e.g., CAR for Ad5, will help to target the recombinant adenovirus to specific cell types expressing the cell surface binding site of the particular peptide ligand incorporated within the modified fiber domain.

The isolated adenovirus fiber proteins contained within the recombinant adenoviruses of the present invention are described below. An isolated adenovirus fiber protein that is modified as described herein can be used as a tool to identify the therapeutically relevant cells and tissues to which a recombinant adenovirus comprising said modified protein will bind and possibly transduce its contents. The modified, isolated adenovirus fiber protein as described herein can also be used as a "binding determinant" that can be linked to other moieties (i.e., virus, protein or DNA) in order to direct said moiety to a target receptor. Any one of the serotypes of human or non-human adenovirus can be used as the source of the fiber protein gene. In one embodiment of the invention, the source of the fiber protein gene is Ad5. The fiber protein is modified in that it comprises amino acid residues that are not typically found in the protein as isolated from wild-type adenovirus (i.e., comprising the native protein, or wild-type protein). These non-wild-type amino acid residues comprise a sequence that represents a peptide ligand for a cell surface binding site. Non-wild-type amino acid residues are preferably introduced into the fiber protein at the level of gene expression (i.e., by introduction of a nucleic acid sequence that encodes then peptide ligand).

The peptide ligands of the present invention comprise a core amino acid sequence of 14 potential amino acid residue positions from which amino acid residues may be added or deleted as described in detail in this specification. This sequence imparts upon the recombinant adenovirus comprising the resultant modified adenovirus fiber protein an ability to bind to cells by means of a cell surface binding site other than, and in addition to, CAR. This gives the recombinant adenovirus a broadened tropism in comparison to wild-type adenovirus. The adenovirus fiber protein and peptide ligand can be engineered to include compatible novel restriction sites to enable the oligonucleotides encoding the peptide ligand to be inserted within the gene encoding the fiber protein. To this end, the insertion of the peptide ligand amino acid sequence into the fiber protein can occur at the nucleic acid level.

A cell surface binding site comprises a binding moiety for a modified adenovirus fiber protein as described herein and encompasses a receptor (e.g., a protein, carbohydrate, glycoprotein, or proteoglycan), any oppositely charged molecule (i.e., oppositely charged with respect to the modified fiber protein), or other type of cell surface molecule to which the modified fiber protein can bind, thereby promoting cell entry. A modified fiber protein of the present invention, and methods of use thereof, is not limited to any particular mechanism of cellular interaction (i.e., interaction with a particular cell surface binding site) and is not to be so construed. The cell surface binding site according to the invention is one that previously was inaccessible to interaction with a wild-type adenovirus fiber protein, or accessible at a very low level. Thus, the modified adenovirus fiber protein, as a result of the inserted peptide ligand, can interact with a binding site present on a cell surface with which a wild-type fiber protein does not bind, or binds with very low affinity. This has the effect of increasing the efficiency of entry of vectors into cells, as well as both increasing the specificity and broadening the range of adenovirus targeting.

The modified adenovirus fiber protein of the present invention, including but not limited to a modified Ad5 fiber protein, comprises a peptide ligand inserted within a fiber protein as described herein. The peptide ligand of the modified fiber protein is integrated within any portion of the fiber protein that enables accessibility of the peptide ligand to the cell surface binding site. The crystal structure of the Ads fiber knob has been described (see, Xia et al., 1994, *Structure* 2:1259-1270). The fiber knob monomer consists of an eight-stranded anti-parallel β-sandwich fold; and the overall structure of the fiber knob trimer resembles a three-bladed propeller with certain β-strands of each of the three monomers comprising the faces of the blades. Only 35% of the fiber knob comprises the β-strands. In particular, the following residues of the Ad5 fiber knob appear to be important for hydrogen bonding in the β-sandwich motif: 400-402, 419-428, 431-440, 454-461, 479-482, 485-486, 516-521, 529-536, 550-557, and 573-578. The remaining 65% of the monomer sequence consists of turns and loops connecting the β-strands. The six prominent loops of the Ad5 fiber knob monomer do not appear to be critical in forming the fiber protein secondary structure. In particular, residues inclusive of 403-418 comprise the AB loop, residues inclusive of 441-453 comprise the CD loop, residues inclusive of 487-514 comprise the DG loop, residues inclusive of 522-528 comprise the GH loop, residues inclusive of 537-549 comprise the HI loop and residues inclusive of 558-572 comprise the IJ loop.

While the addition of the peptide ligand within the fiber protein must produce an accessible binding moiety for cell targeting, it must not disturb the ability for the fiber protein to trimerize. Accordingly, insertion of the peptide ligand within an exposed loop domain which contributes the least to intramolecular interactions in the knob is preferred. Therefore, in one embodiment of the invention, the peptide ligand is inserted within an exposed loop domain of an adenovirus fiber knob. While such loops are defined herein with respect to the Ad5 sequence, the sequence alignment of other fiber knob species has been described (see, Xia, D. et al., supra). The corresponding residues in the fiber knob that are important for protein binding/folding appear to be conserved between fiber proteins of different adenoviral serotypes. This suggests that even for those adenoviral species in which the crystal structure of the fiber protein is not known, outside of these conserved residues lie non-conserved regions, or regions that do not exhibit the high level of conservation observed for the residues critical to protein functionality. It is likely that the sequence of the fiber knob protein in these non-conserved regions exist as a loop due to the absence of important intra-molecular interactions in these regions of the protein.

The fiber knob loop in which the peptide ligand of the present invention can be inserted is selected from the group consisting of the AB, CD, DO, GH, HI and IJ loops. In Ad5, these loop comprise amino acid residues selected from the group consisting of residues 403-418, 441-453, 487-514, 522-528, 537-549, and 558-572, respectively. In one embodiment of the invention, the peptide ligand is inserted within the HI loop of an adenovirus fiber knob, including but not limited to an Ad5 fiber knob. In Ad5, the HI loop comprises 13 amino acid residues, each hydrophilic, and is exposed outside of the knob. The HI loop has been shown to be an optimal location in which to incorporate heterologous ligands because it demonstrates a high degree of flexibility. Also, there is variability in the length of the HI loop in the different adenovirus serotypes, suggesting that alterations in the original loop structure are likely tolerated without affecting proper folding of the knob domain. In the present invention, the peptide ligand for the cell surface binding site can be incorporated within the fiber protein, optimally within a loop domain of the fiber knob, without removing any endogenous fiber protein sequence. Alternatively; the peptide ligand can take the place of a portion of the protein sequence of the adenovirus fiber protein, albeit without disturbing normal function of the protein. In one embodiment of the invention, and as exemplified in the Examples section herein, the peptide ligand can be inserted between amino acid residue 546 and amino acid residue 547 of the Ad5 fiber protein within the HI loop of the fiber knob. This heterologous amino acid sequence is preferably introduced at the nucleic acid level of the fiber protein. The presence of the peptide ligand in the fiber protein will allow the recombinant adenovirus to achieve CAR-independent gene transfer.

It is important that the modified fiber protein of the present invention maintains proper trimer formation to support target cell interaction. Trimer formation can be assessed using a vaccinia expression system. Generally, the recombinant vaccinia virus vector, pTKgpt-3S, described by Falkner, 1988, *J. Virol.* 62:1849-1854, can be used to produce the modified adenovirus fiber protein in isolation from the remainder of the adenovirus. This vector provides a convenient cloning site for the fiber protein and includes the *E. coli* gpt gene as a selectable marker for the recombinant vaccinia virus containing the adenoviral fiber gene. Fiber protein has also been expressed in recombinant vaccinia viruses using the two virus bacteriophage T7 RNA polymerase approach described by Fuerst et al., 1986, *Proc. Natl. Acad. Sci. USA* 83:8122-8126. Other eukaryotic expression vectors, such as recombinant retroviruses, can also be used to produce normally glycosylated fiber protein in sufficient amounts for functional testing of trimerization. The vaccinia-produced fiber protein can be readily tested for trimerization using western blot analysis in conjunction with monoclonal antibodies capable of differentiating between monomeric and trimeric forms of the protein. Two such monoclonal antibodies, antibody 4D2.5 and antibody 2A6.36, have been characterized by Hong and Engler, 1991, *Virology* 185:758-767. Other antibodies can be produced as described by Hong and Engler, using standard techniques. Using these antibodies, information about the structure of the modified fiber can be obtained by both Western blot and by indirect immunofluorescence.

Binding of the modified fiber protein to a target cell can be determined using standard techniques. For example, the recombinant adenovirus containing the modified fiber protein can be radiolabeled, added to cells, and incubated. Unbound virus is washed away and the amount of radioactivity bound to the cells is measured. Alternatively, cells can be infected with recombinant virus comprising the modified fiber protein using a known virus titer. Then, cell lysis can be determined with a cytopathic assay. Only cells where the virus binds can be infected, resulting in cell death.

The present invention relates in part to a recombinant adenovirus comprising a modified Ad5 fiber protein consisting of the amino acid sequence as disclosed in FIG. 1 and as set forth in SEQ ID NO:1. A further embodiment of the invention is an isolated Ad5 fiber protein consisting of the amino acid sequence of SEQ ID NO:1. SEQ ID NO:1 (the Ad5 fiber-L1 protein) represents the amino acid sequence of an Ad5 fiber protein which has inserted within the HI loop of the fiber knob, between amino acid residues 546 and 547, the L1 peptide ligand consisting of the amino acid sequence as set forth in SEQ ID NO:13. SEQ ID NO:1 is as follows, wherein the knob domain is underlined, the L1 peptide ligand sequence is in italics, and the residues added to the wild-type Ad5 fiber sequence in order to facilitate insertion of the peptide ligand and to maintain the wild-type sequence are in lowercase:

```
                                              (SEQ ID NO:1)
 1 MKRARPSEDT FNPVYPYDTE TGPPTVPFLT PPFVSPNGFQ
   ESPPGVLSLR LSEPLVTSNG

61 MLALKMGNGL SLDEAGNLTS QNVTTVSPPL KKTKSNINLE
```

```
        ISAPLTVTSE ALTVAAAAPL

121 MVAGNTLTMQ SQAPLTVHDS KLSIATQGPL TVSEGKLALQ
    TSGPLTTTDS STLTITASPP

181 LTTATGSLGI DLKEPIYTQN GKLGLKYGAP LHVTDDLNTL
    TVATGPGVTI NNTSLQTKVT

241 GALGFDSQGN MQLNVAGGLR IDSQNRRLIL DVSYPFDAQN
    QLNLRLGQGP LFINSAHNLD

301 INYNKGLYLF TASNNSKKLE VNLSTAKGLM FDATAIAINA
    GDGLEFGSPN APNTNPLKTK

361 IGHGLEFDSN KAMVPKLGTG LSFDSTGAIT VGNKNNDKLT
    LWTTPAPSPN CRLNAEKDAK

421 LTLVLTKCGS QILATVSVLA VKGSLAPISG TVQSAHLIIR
    FDENGVLLNN SFLDPEYWNF

481 RNGDLTEGTA YTNAVGFMPN LSAYPKSHGK TAKSNIVSQV
    YLNGDKTKPV TLTITLNGTQ

541 ETGDTTsFCV ASRGGSSCYa aaPSAYSMSF SWDWSGHNYI
    NEIFATSSYT FSYIAQE*.
```

The present invention also relates in part to a recombinant adenovirus comprising a modified Ad5 fiber protein consisting of the amino acid sequence as disclosed in FIG. 2 and as set forth in SEQ ID NO:2. A further embodiment of the invention is an isolated Ad5 fiber protein consisting of the amino acid sequence of SEQ ID NO:2. SEQ ID NO:2 (the Ad5 fiber-L16 protein) represents the amino acid sequence of an Ad5 fiber protein which has inserted within the HI loop of the fiber knob, between amino acids 546 and 547, the L16 peptide ligand consisting of the amino acid sequence as set forth in SEQ ID NO:14. SEQ ID NO:2 is as follows, wherein the knob domain is underlined, the L16 peptide ligand sequence is in italics, and the residues added to the wild-type Ad5 fiber sequence in order to facilitate insertion of the peptide ligand and to maintain the wild-type sequence are in lowercase:

```
                                              (SEQ ID NO:2)
  1 MKRARPSEDT FNPVYPYDTE TGPPTVPFLT PPFVSPNGFQ
    ESPPGVLSLR LSEPLVTSNG

61 MLALKMGNGL SLDEAGNLTS QNVTTVSPPL KKTKSNINLE
    ISAPLTVTSE ALTVAAAAPL

121 MVAGNTLTMQ SQAPLTVHDS KLSIATQGPL TVSEGKLALQ
    TSGPLTTTDS STLTITASPP

181 LTTATGSLGI DLKEPIYTQN GKLGLKYGAP LHVTDDLNTL
    TVATGPGVTI NNTSLQTKVT

241 GALGFDSQGN MQLNVAGGLR IDSQNRRLIL DVSYPFDAQN
    QLNLRLGQGP LFINSAHNLD

301 INYNKGLYLF TASNNSKKLE VNLSTAKGLM FDATAIAINA
    GDGLEFGSPN APNTNPLKTK

361 IGHGLEFDSN KAMVPKLGTG LSFDSTGAIT VGNKNNDKLT
    LWTTPAPSPN CRLNAEKDAK

421 LTLVLTKCGS QILATVSVLA VKGSLAPISG TVQSAHLIIR
    FDENGVLLNN SFLDPEYWNF

481 RNGDLTEGTA YTNAVGFMPN LSAYPKSHGK TAKSNIVSQV
    YLNGDKTKPV TLTITLNGTQ

541 ETGDTTsFCK VVGGGSSCSP aaaPSAYSMS FSWDWSGHNY
    INEIFATSSY TFSYIAQE*.
```

The present invention also relates in part to a recombinant adenovirus comprising a modified Ad5 fiber protein consisting of the amino acid sequence as disclosed in FIG. 3 and as set forth in SEQ ID NO:3. A further embodiment of the invention is an isolated Ad5 fiber protein consisting of the amino acid sequence of SEQ ID NO:3. SEQ ID NO:3 (the Ad5 fiber-L33 protein) represents the amino acid sequence of an Ad5 fiber protein which has inserted within the HI loop of the fiber knob, between amino acids 546 and 547, the L33 peptide ligand consisting of the amino acid sequence as set forth in SEQ ID NO:15. SEQ ID NO:3 is as follows, wherein the knob domain is underlined, the L33 peptide ligand sequence is in italics, and the residues added to the wild-type Ad5 fiber sequence in order to facilitate insertion of the peptide ligand and to maintain the wild-type sequence are in lowercase:

```
                                              (SEQ ID NO:3)
  1 MKRARPSEDT FNPVYPYDTE TGPPTVPFLT PPFVSPNGFQ
    ESPPGVLSLR LSEPLVTSNG

61 MLALKMGNGL SLDEAGNLTS QNVTTVSPPL KKTKSNINLE
    ISAPLTVTSE ALTVAAAAPL

121 MVAGNTLTMQ SQAPLTVHDS KLSIATQGPL TVSEGKLALQ
    TSGPLTTTDS STLTITASPP

181 LTTATGSLGI DLKEPIYTQN GKLGLKYGAP LHVTDDLNTL
    TVATGPGVTI NNTSLQTKVT

241 GALGFDSQGN MQLNVAGGLR IDSQNRRLIL DVSYPFDAQN
    QLNLRLGQGP LFINSAHNLD

301 INYNKGLYLF TASNNSKKLE VNLSTAKGLM FDATAIAINA
    GDGLEFGSPN APNTNPLKTK

361 IGHGLEFDSN KAMVPKLGTG LSFDSTGAIT VGNKNNDKLT
    LWTTPAPSPN CRLNAEKDAK

421 LTLVLTKCGS QILATVSVLA VKGSLAPISG TVQSAHLIIR
    FDENGVLLNN SFLDPEYWNF

481 RNGDLTEGTA YTNAVGFMPN LSAYPKSHGK TAKSNIVSQV
    YLNGDKTKPV TLTITLNGTQ

541 ETGDTTsFFC VSDGGGSSCP aaaPSAYSMS FSWDWSGHNY
    INEIFATSSY TFSYIAQE*.
```

The present invention relates to an isolated peptide consisting of the amino acid sequence as set forth in SEQ ID NO:13 (the L1 peptide ligand), disclosed as follows: FCVASRGGSSCY.

The present invention also relates to an isolated peptide consisting of the amino acid sequence as set forth in SEQ ID NO:14 (the L16 peptide ligand), disclosed as follows: FCKVVGGGSSCSP.

The present invention further relates to an isolated peptide consisting of the amino acid sequence as set forth in SEQ ID NO:15 (the L33 peptide ligand), disclosed as follows: FFCVSDGGGSSCP.

The present invention also relates to a modified fiber protein as disclosed herein that has been further modified to abolish binding to its wild-type cell surface binding site. CAR is the main cell surface binding site for many, but not all, adenovirus serotypes. In one embodiment, wild-type CAR binding of a modified Ad5 fiber protein is ablated. Ablating the ability of adenovirus to bind its wild-type receptor (e.g., CAR for many adenovirus serotypes) requires the presence of an alternative and efficient interaction between the virus capsid and a receptor expressed on an E1-expressing cell line for amplifying the virus. CAR binding of the Ad5 fiber protein is ablated as a result of specific sequence modifications to the fiber protein, including but not limited to deletion of amino acid residue 489 to amino acid residue 492.

The present invention relates in part to an isolated Ad5 fiber protein consisting of the amino acid sequence as disclosed in FIG. 7 and as set forth in SEQ ID NO:7. SEQ ID NO:7 (the Ad5 fiberΔ-L1 protein) represents the amino acid sequence of an Ad5 fiber protein harboring the deletion of amino acid residues TAYT (SEQ ID NO:45) from amino acid residue 489 to 492 of the Ad5 fiber protein, abrogating CAR binding. Additionally, the L1 peptide (SEQ ID NO:13) is inserted within the HI loop of the fiber knob, between amino acids 546 and 547. SEQ ID NO:7 is as follows, wherein the knob domain is underlined, the amino acids flanking the deletion are double underlined, the L1 peptide ligand sequence is in italics, and the residues added to the wild-type Ad5 fiber sequence in order to facilitate insertion of the peptide ligand and to maintain the wild-type sequence are in lowercase:

```
                                                    (SEQ ID NO:7)
  1 MKRARPSEDT FNPVYPYDTE TGPPTVPFLT PPFVSPNGFQ
    ESPPGVLSLR LSEPLVTSNG

61 MLALKMGNGL SLDEAGNLTS QNVTTVSPPL KKTKSNINLE
    ISAPLTVTSE ALTVAAAAPL

121 MVAGNTLTMQ SQAPLTVHDS KLSIATQGPL TVSEGKLALQ
    TSGPLTTTDS STLTITASPP

181 LTTATGSLGI DLKEPIYTQN GKLGLKYGAP LHVTDDLNTL
    TVATGPGVTI NNTSLQTKVT

241 GALGFDSQGN MQLNVAGGLR IDSQNRRLIL DVSYPFDAQN
    QLNLRLGQGP LFINSAHNLD

301 INYNKGLYLF TASNNSKKLE VNLSTAKGLM FDATAIAINA
    GDGLEFGSPN APNTNPLKTK

361 IGHGLEFDSN KAMVPKLGTG LSFDSTGAIT VGNKNND

-continued

```
541 TTsFFCVSDG GGSSCPaaaP SAYSMSFSWD WSGHNYINEI
    FATSSYTFSY IAQE*.
```

The heterologous peptide ligand sequence, preferably, will be inserted within the fiber protein at the level of the nucleic acid. Accordingly, the present invention further relates to isolated nucleic acid molecules encoding any modified adenovirus fiber protein encompassing the characteristics described within this specification. The isolated nucleic acid molecule of the present invention may include a deoxyribonucleic acid molecule (DNA) which may be single (coding or noncoding strand) or double stranded, as well as synthetic DNA, such as a synthesized, single stranded polynucleotide. The isolated nucleic acid molecule of the present invention may also include a ribonucleic acid molecule (RNA). Another aspect of the invention relates to recombinant vectors and recombinant hosts, both prokaryotic and eukaryotic, which contain the isolated nucleic acid molecules encoding the modified adenovirus fiber proteins disclosed throughout this specification, in addition to a process of expressing a modified adenovirus fiber protein of the present invention in a recombinant host cell.

In accordance with the present invention, the means of generating a modified fiber protein as disclosed herein, particularly the means of introducing the heterologous peptide ligand sequence at the level of DNA, is well known in the art and may employ molecular biology, microbiology, and recombinant DNA techniques. Such techniques are explained fully in the literature. See, e.g., Sambrook et al., 1989, *Molecular Cloning: A Laboratory Manual;* Cold Spring Harbor Laboratory, Cold Spring Harbor, N.Y. The nucleic acid molecules of the present invention are substantially free from other nucleic acids.

Any of a variety of procedures may be used to clone a wild-type adenovirus fiber protein of a specific serotype. These methods include, but are not limited to, (1) a RACE PCR cloning technique (Frohman et al., 1988, *Proc. Natl. Acad. Sci. USA* 85: 8998-9002). 5' and/or 3' RACE may be performed to generate a full-length cDNA sequence. This strategy involves using gene-specific oligonucleotide primers for PCR amplification of the adenovirus fiber protein cDNA. These gene-specific primers are designed through identification of adenovirus fiber protein sequences by searching any number of publicly available nucleic acid and protein databases; (2) direct functional expression of an adenovirus fiber protein cDNA following the construction of an adenovirus fiber protein-containing cDNA library in an appropriate expression vector system; (3) screening an adenovirus fiber protein-containing cDNA library constructed in a bacteriophage or plasmid shuttle vector with a labeled degenerate oligonucleotide probe designed from the amino acid sequence of an adenovirus fiber protein; (4) screening an adenovirus fiber protein-containing cDNA library constructed in a bacteriophage or plasmid shuttle vector with a partial cDNA encoding an adenovirus fiber protein. This partial cDNA is obtained by the specific PCR amplification of adenovirus fiber protein DNA fragments through the design of degenerate oligonucleotide primers from the amino acid sequence known for various adenovirus fiber proteins of different serotypes; or (5) for cloning an Ad5 fiber protein, designing 5' and 3' gene specific oligonucleotides using the wild-type Ad5 sequence located within SEQ ID NOs:4-6 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding the specific adenovirus fiber protein.

Once the wild-type adenovirus fiber protein has been isolated, the peptide ligand is inserted with the fiber protein such that the now modified adenovirus fiber protein contains a binding moiety of which the wild-type protein did not have. The peptide ligand can be inserted into or in place of a portion of the adenovirus fiber protein sequence. The method of making such a modified fiber protein is described in the Examples section to follow. Generally, the method comprises introducing a oligonucleotide sequence that encodes the heterologous peptide ligand into the nucleic acid sequence encoding the adenovirus fiber protein so as to insert the peptide ligand within the protein sequence of the wild-type fiber protein, optimally within a loop of the fiber knob. This can be accomplished by cloning the nucleic acid sequence encoding the wild-type fiber protein into a plasmid or some other vector for ease of manipulation of the sequence. Then, one or two unique restriction sites can be added into the fiber protein to create a spot at which further sequences, e.g., the peptide ligand DNA sequence, can be inserted into the fiber DNA sequence. A double-stranded synthetic oligonucleotide encoding the heterologous peptide ligand generally is created from overlapping synthetic single-stranded sense and antisense oligonucleotides. The resulting double-stranded oligonucleotide contains flanking restriction sites that are complementary to the unique restriction sites previously incorporated into the fiber gene DNA. The plasmid or other vector is cleaved with the appropriate restriction enzyme(s), and the oligonucleotide sequence having compatible cohesive ends is ligated into the plasmid or other vector to either add to or replace part of the wild-type DNA. Other means of in vitro site-directed mutagenesis known to those skilled in the art can be used (in particular, using PCR), by means of commercially available kits, to introduce the peptide ligand sequence into the adenovirus fiber protein coding sequence.

The present invention relates to the isolated or purified nucleic acid molecule described in FIG. 4 (the Ad5 fiber-L1 DNA), and as set forth in SEQ ID NO:4, which encodes the modified Ad5 fiber protein described in FIG. 1 (SEQ ID NO:1; Ad5 fiber-L1). The nucleotide sequence of Ad5 fiber-L1 is as follows, wherein the knob is underlined, the nucleic acid sequence encoding the L1 peptide ligand is in italics, and the additional sequence variation accounting for the engineered restriction site to facilitate insertion of the nucleotide sequence encoding L1 into the fiber sequence is in lowercase:

```
                                        (SEQ ID NO:4)
  1 ATGAAGCGCG CAAGACCGTC TGAAGATACC TTCAACCCCG
    TGTATCCATA TGACACGGAA

61 ACCGGTCCTC CAACTGTGCC TTTTCTTACT CCTCCCTTTG
    TATCCCCCAA TGGGTTTCAA

121 GAGAGTCCCC CTGGGGTACT CTCTTTGCGC CTATCCGAAC
    CTCTAGTTAC CTCCAATGGC

181 ATGCTTGCGC TCAAAATGGG CAACGGCCTC TCTCTGGACG
    AGGCCGGCAA CCTTACCTCC

241 CAAAATGTAA CCACTGTGAG CCCACCTCTC AAAAAAACCA
    AGTCAAACAT AAACCTGGAA

301 ATATCTGCAC CCCTCACAGT TACCTCAGAA GCCCTAACTG
    TGGCTGCCGC CGCACCTCTA
```

-continued

```
 361 ATGGTCGCGG GCAACACACT CACCATGCAA TCACAGGCCC
     CGCTAACCGT GCACGACTCC

421 AAACTTAGCA TTGCCACCCA AGGACCCCTC ACAGTGTCAG
     AAGGAAAGCT AGCCCTGCAA

481 ACATCAGGCC CCCTCACCAC CACCGATAGC AGTACCCTTA
     CTATCACTGC CTCACCCCCT

541 CTAACTACTG CCACTGGTAG CTTGGGCATT GACTTGAAAG
     AGCCCATTTA TACACAAAAT

601 GGAAAACTAG GACTAAAGTA CGGGGCTCCT TTGCATGTAA
     CAGACGACCT AAACACTTTG

661 ACCGTAGCAA CTGGTCCAGG TGTGACTATT AATAATACTT
     CCTTGCAAAC TAAAGTTACT

721 GGAGCCTTGG GTTTTGATTC ACAAGGCAAT ATGCAACTTA
     ATGTAGCAGG AGGACTAAGG

781 ATTGATTCTC AAAACAGACG CCTTATACTT GATGTTAGTT
     ATCCGTTTGA TGCTCAAAAC

841 CAACTAAATC TAAGACTAGG ACAGGGCCCT CTTTTTATAA
     ACTCAGCCCA CAACTTGGAT

901 ATTAACTACA ACAAAGGCCT TTACTTGTTT ACAGCTTCAA
     ACAATTCCAA AAAGCTTGAG

961 GTTAACCTAA GCACTGCCAA GGGGTTGATG TTTGACGCTA
     CAGCCATAGC CATTAATGCA

1021 GGAGATGGGC TTGAATTTGG TTCACCTAAT GCACCAAACA
     CAAATCCCCT CAAAACAAAA

1081 ATTGGCCATG GCCTAGAATT TGATTCAAAC AAGGCTATGG
     TTCCTAAACT AGGAACTGGC

1141 CTTAGTTTTG ACAGCACAGG TGCCATTACA GTAGGAAACA
     AAAATAATGA TAAGCTAACT

1201 TTGTGGACCA CACCAGCTCC ATCTCCTAAC TGTAGACTAA
     ATGCAGAGAA AGATGCTAAA

1261 CTCACTTTGG TCTTAACAAA ATGTGGCAGT CAAATACTTG
     CTACAGTTTC AGTTTTGGCT

1321 GTTAAAGGCA GTTTGGCTCC AATATCTGGA ACAGTTCAAA
     GTGCTCATCT TATTATAAGA

1381 TTTGACGAAA ATGGAGTGCT ACTAAACAAT TCCTTCCTGG
     ACCCAGAATA TTGGAACTTT

1441 AGAAATGGAG ATCTTACTGA AGGCACAGCC TATACAAACG
     CTGTTGGATT TATGCCTAAC

1501 CTATCAGCTT ATCCAAAATC TCACGGTAAA ACTGCCAAAA
     GTAACATTGT CAGTCAAGTT

1561 TACTTAAACG GAGACAAAAC TAAACCTGTA ACACTAACCA
     TTACACTAAA CGGTACACAG

1621 GAAACAGGAG ACACAACTag tTTCTGCGTT GCGTCCCGCG
     GTGGGTCCTC CTGCTACgcg 1681 gccgctCCtt ccGCATACTC TATGTCATTT TCATGGGACT
     GGTCTGGCCA CAACTACATT

1741 AATGAAATAT TGCCACATC CTCTTACACT TTTTCATACA
     TTGCCCAAGA ATAA.
```

The present invention also relates to the isolated or purified nucleic acid molecule described in FIG. 5 (the Ad5 fiber-L16 DNA), and as set forth in SEQ ID NO:5, which encodes the modified Ad5 fiber protein described in FIG. 2 (SEQ ID NO:2; Ad5 fiber-L16). The nucleotide sequence of Ad5 fiber-L16 is as follows, wherein the knob is underlined, the nucleic acid sequence encoding the L16 peptide ligand is in italics, and the additional sequence variation accounting for the engineered restriction site to facilitate insertion of the nucleotide sequence encoding L16 into the fiber sequence is in lower-case:

```
                                             (SEQ ID NO:5)
   1 ATGAAGCGCG CAAGACCGTC TGAAGATACC TTCAACCCCG
     TGTATCCATA TGACACGGAA

61 ACCGGTCCTC CAACTGTGCC TTTTCTTACT CCTCCCTTTG
     TATCCCCCAA TGGGTTTCAA

121 GAGAGTCCCC CTGGGGTACT CTCTTTGCGC CTATCCGAAC
     CTCTAGTTAC CTCCAATGGC

181 ATGCTTGCGC TCAAAATGGG CAACGGCCTC TCTCTGGACG
     AGGCCGGCAA CCTTACCTCC

241 CAAAATGTAA CCACTGTGAG CCCACCTCTC AAAAAAACCA
     AGTCAAACAT AAACCTGGAA

301 ATATCTGCAC CCCTCACAGT TACCTCAGAA GCCCTAACTG
     TGGCTGCCGC CGCACCTCTA

361 ATGGTCGCGG GCAACACACT CACCATGCAA TCACAGGCCC
     CGCTAACCGT GCACGACTCC

421 AAACTTAGCA TTGCCACCCA AGGACCCCTC ACAGTGTCAG
     AAGGAAAGCT AGCCCTGCAA

481 ACATCAGGCC CCCTCACCAC CACCGATAGC AGTACCCTTA
     CTATCACTGC CTCACCCCCT

541 CTAACTACTG CCACTGGTAG CTTGGGCATT GACTTGAAAG
     AGCCCATTTA TACACAAAAT

601 GGAAAACTAG GACTAAAGTA CGGGGCTCCT TTGCATGTAA
     CAGACGACCT AAACACTTTG

661 ACCGTAGCAA CTGGTCCAGG TGTGACTATT AATAATACTT
     CCTTGCAAAC TAAAGTTACT

721 GGAGCCTTGG GTTTTGATTC ACAAGGCAAT ATGCAACTTA
     ATGTAGCAGG AGGACTAAGG

781 ATTGATTCTC AAAACAGACG CCTTATACTT GATGTTAGTT
     ATCCGTTTGA TGCTCAAAAC

841 CAACTAAATC TAAGACTAGG ACAGGGCCCT CTTTTTATAA
     ACTCAGCCCA CAACTTGGAT

901 ATTAACTACA ACAAAGGCCT TTACTTGTTT ACAGCTTCAA
     ACAATTCCAA AAAGCTTGAG

961 GTTAACCTAA GCACTGCCAA GGGGTTGATG TTTGACGCTA
     CAGCCATAGC CATTAATGCA

1021 GGAGATGGGC TTGAATTTGG TTCACCTAAT GCACCAAACA
     CAAATCCCCT CAAAACAAAA

1081 ATTGGCCATG GCCTAGAATT TGATTCAAAC AAGGCTATGG
     TTCCTAAACT AGGAACTGGC

1141 CTTAGTTTTG ACAGCACAGG TGCCATTACA GTAGGAAACA
     AAAATAATGA TAAGCTAACT

1201 TTGTGGACCA CACCAGCTCC ATCTCCTAAC TGTAGACTAA
     ATGCAGAGAA AGATGCTAAA

1261 CTCACTTTGG TCTTAACAAA ATGTGGCAGT CAAATACTTG
     CTACAGTTTC AGTTTTGGCT

1321 GTTAAAGGCA GTTTGGCTCC AATATCTGGA ACAGTTCAAA
     GTGCTCATCT TATTATAAGA

1381 TTTGACGAAA ATGGAGTGCT ACTAAACAAT TCCTTCCTGG
     ACCCAGAATA TTGGAACTTT
```

```
1441  AGAAATGGAG ATCTTACTGA AGGCACAGCC TATACAAACG
      CTGTTGGATT TATGCCTAAC

1501  CTATCAGCTT ATCCAAAATC TCACGGTAAA ACTGCCAAAA
      GTAACATTGT CAGTCAAGTT

1561  TACTTAAACG GAGACAAAAC TAAACCTGTA ACACTAACCA
      TTACACTAAA CGGTACACAG

1621  GAAACAGGAG ACACAACTag tTTCTGCAAG GTCGTGGGTG
      GTGGTTCCTC CTGCTCCCCG 1681  gcggccgctC CttccGCATA CTCTATGTCA TTTTCATGGG
      ACTGGTCTGG CCACAACTAC

1741  ATTAATGAAA TATTTGCCAC ATCCTCTTAC ACTTTTTCAT
      ACATTGCCCA AGAATAA.
```

The present invention further relates to the isolated or purified nucleic acid molecule described in FIG. 6 (the Ad5 fiber-L33 DNA), and as set forth in SEQ ID NO:6, which encodes the modified Ad5 fiber protein described in FIG. 3 (SEQ ID NO:3; Ad5 fiber-L33). The nucleotide sequence of Ad5 fiber-L33 is as follows, wherein the knob is underlined, the nucleic acid sequence encoding the L33 peptide ligand is in italics, and the additional sequence variation accounting for the engineered restriction site to facilitate insertion of the nucleotide sequence encoding L33 into the fiber sequence is in lowercase:

```
                                          (SEQ ID NO:6)
   1  ATGAAGCGCG CAAGACCGTC TGAAGATACC TTCAACCCCG
      TGTATCCATA TGACACGGAA

61  ACCGGTCCTC CAACTGTGCC TTTTCTTACT CCTCCCTTTG
      TATCCCCCAA TGGGTTTCAA

121  GAGAGTCCCC CTGGGGTACT CTCTTTGCGC CTATCCGAAC
      CTCTAGTTAC CTCCAATGGC

181  ATGCTTGCGC TCAAAATGGG CAACGGCCTC TCTCTGGACG
      AGGCCGGCAA CCTTACCTCC

241  CAAAATGTAA CCACTGTGAG CCCACCTCTC AAAAAAACCA
      AGTCAAACAT AAACCTGGAA

301  ATATCTGCAC CCCTCACAGT TACCTCAGAA GCCCTAACTG
      TGGCTGCCGC CGCACCTCTA

361  ATGGTCGCGG GCAACACACT CACCATGCAA TCACAGGCCC
      CGCTAACCGT GCACGACTCC

421  AAACTTAGCA TTGCCACCCA AGGACCCCTC ACAGTGTCAG
      AAGGAAAGCT AGCCCTGCAA

481  ACATCAGGCC CCCTCACCAC CACCGATAGC AGTACCCTTA
      CTATCACTGC CTCACCCCCT

541  CTAACTACTG CCACTGGTAG CTTGGGCATT GACTTGAAAG
      AGCCCATTTA TACACAAAAT

601  GGAAAACTAG GACTAAAGTA CGGGGCTCCT TTGCATGTAA
      CAGACGACCT AAACACTTTG

661  ACCGTAGCAA CTGGTCCAGG TGTGACTATT AATAATACTT
      CCTTGCAAAC TAAAGTTACT

721  GGAGCCTTGG GTTTTGATTC ACAAGGCAAT ATGCAACTTA
      ATGTAGCAGG AGGACTAAGG

781  ATTGATTCTC AAAACAGACG CCTTATACTT GATGTTAGTT
      ATCCGTTTGA TGCTCAAAAC

841  CAACTAAATC TAAGACTAGG ACAGGGCCCT CTTTTTATAA
      ACTCAGCCCA CAACTTGGAT
```

```
 901  ATTAACTACA ACAAAGGCCT TTACTTGTTT ACAGCTTCAA
      ACAATTCCAA AAAGCTTGAG

961  GTTAACCTAA GCACTGCCAA GGGGTTGATG TTTGACGCTA
      CAGCCATAGC CATTAATGCA

1021  GGAGATGGGC TTGAATTTGG TTCACCTAAT GCACCAAACA
      CAAATCCCCT CAAAACAAAA

1081  ATTGGCCATG GCCTAGAATT TGATTCAAAC AAGGCTATGG
      TTCCTAAACT AGGAACTGGC

1141  CTTAGTTTTG ACAGCACAGG TGCCATTACA GTAGGAAACA
      AAAATAATGA TAAGCTAACT

1201  TTGTGGACCA CACCAGCTCC ATCTCCTAAC TGTAGACTAA
      ATGCAGAGAA AGATGCTAAA

1261  CTCACTTTGG TCTTAACAAA ATGTGGCAGT CAAATACTTG
      CTACAGTTTC AGTTTTGGCT

1321  GTTAAAGGCA GTTTGGCTCC AATATCTGGA ACAGTTCAAA
      GTGCTCATCT TATTATAAGA

1381  TTTGACGAAA ATGGAGTGCT ACTAAACAAT TCCTTCCTGG
      ACCCAGAATA TTGGAACTTT

1441  AGAAATGGAG ATCTTACTGA AGGCACAGCC TATACAAACG
      CTGTTGGATT TATGCCTAAC

1501  CTATCAGCTT ATCCAAAATC TCACGGTAAA ACTGCCAAAA
      GTAACATTGT CAGTCAAGTT

1561  TACTTAAACG GAGACAAAAC TAAACCTGTA ACACTAACCA
      TTACACTAAA CGGTACACAG

1621  GAAACAGGAG ACACAACTag tTTCTTCTGC GTTTCCGACG
      GTGGTGGTTC CTCCTGCCCG 1681  gcggccgctC CttccGCATA CTCTATGTCA TTTTCATGGG
      ACTGGTCTGG CCACAACTAC

1741  ATTAATGAAA TATTTGCCAC ATCCTCTTAC ACTTTTTCAT
      ACATTGCCCA AGAATAA.
```

The present invention relates to the isolated or purified nucleic acid molecule described in FIG. 10 (the Ad5 fiberΔ-L1 DNA), and as set forth in SEQ ID NO:10, which encodes the Ad5 fiberΔ-L1 protein of the present invention, as described in FIG. 7 and as set forth in SEQ ID NO:7. This sequence harbors the deletion of nucleotides 1465 through 1476 (ACAGCCTATACA; SEQ ID NO:47) of the nucleic acid sequence encoding the wild-type Ad5 fiber protein. This nucleotide deletion corresponds to the deletion of amino acid residues TAYT (SEQ ID NO:45), described herein, which abrogates Ad5 fiber protein binding to CAR. In addition, this sequence contains the nucleic acid sequence encoding the L1 peptide ligand within the HI loop of the fiber knob. The nucleotide sequence of Ad5 fiberΔ-L1 is as follows, wherein the knob is underlined, the nucleotide codons flanking the deletion are double underlined, the nucleic acid sequence encoding the L1 peptide ligand is in italics, and the additional sequence variation accounting for the engineered restriction site to facilitate insertion of the nucleotide sequence encoding L1 into the fiber sequence and to maintain the wild-type sequence is in lowercase:

```
                                         (SEQ ID NO:10)
   1  ATGAAGCGCG CAAGACCGTC TGAAGATACC TTCAACCCCG
      TGTATCCATA TGACACGGAA

61  ACCGGTCCTC CAACTGTGCC TTTTCTTACT CCTCCCTTTG
      TATCCCCCAA TGGGTTTCAA
```

```
121  GAGAGTCCCC CTGGGGTACT CTCTTTGCGC CTATCCGAAC
     CTCTAGTTAC CTCCAATGGC

181  ATGCTTGCGC TCAAAATGGG CAACGGCCTC TCTCTGGACG
     AGGCCGGCAA CCTTACCTCC

241  CAAAATGTAA CCACTGTGAG CCCACCTCTC AAAAAAACCA
     AGTCAAACAT AAACCTGGAA

301  ATATCTGCAC CCCTCACAGT TACCTCAGAA GCCCTAACTG
     TGGCTGCCGC CGCACCTCTA

361  ATGGTCGCGG GCAACACACT CACCATGCAA TCACAGGCCC
     CGCTAACCGT GCACGACTCC

421  AAACTTAGCA TTGCCACCCA AGGACCCCTC ACAGTGTCAG
     AAGGAAAGCT AGCCCTGCAA

481  ACATCAGGCC CCCTCACCAC CACCGATAGC AGTACCCTTA
     CTATCACTGC CTCACCCCCT

541  CTAACTACTG CCACTGGTAG CTTGGGCATT GACTTGAAAG
     AGCCCATTTA TACACAAAAT

601  GGAAAACTAG GACTAAAGTA CGGGGCTCCT TTGCATGTAA
     CAGACGACCT AAACACTTTG

661  ACCGTAGCAA CTGGTCCAGG TGTGACTATT AATAATACTT
     CCTTGCAAAC TAAAGTTACT

721  GGAGCCTTGG GTTTTGATTC ACAAGGCAAT ATGCAACTTA
     ATGTAGCAGG AGGACTAAGG

781  ATTGATTCTC AAAACAGACG CCTTATACTT GATGTTAGTT
     ATCCGTTTGA TGCTCAAAAC

841  CAACTAAATC TAAGACTAGG ACAGGGCCCT CTTTTTATAA
     ACTCAGCCCA CAACTTGGAT

901  ATTAACTACA ACAAAGGCCT TTACTTGTTT ACAGCTTCAA
     ACAATTCCAA AAAGCTTGAG

961  GTTAACCTAA GCACTGCCAA GGGGTTGATG TTTGACGCTA
     CAGCCATAGC CATTAATGCA

1021 GGAGATGGGC TTGAATTTGG TTCACCTAAT GCACCAAACA
     CAAATCCCCT CAAAACAAAA

1081 ATTGGCCATG GCCTAGAATT TGATTCAAAC AAGGCTATGG
     TTCCTAAACT AGGAACTGGC

1141 CTTAGTTTTG ACAGCACAGG TGCCATTACA GTAGGAAACA
     AAAATAATGA TAAGCTAACT

1201 TTGTGGACCA CACCAGCTCC ATCTCCTAAC TGTAGACTAA
     ATGCAGAGAA AGATGCTAAA

1261 CTCACTTTGG TCTTAACAAA ATGTGGCAGT CAAATACTTG
     CTACAGTTTC AGTTTTGGCT

1321 GTTAAAGGCA GTTTGGCTCC AATATCTGGA ACAGTTCAAA
     GTGCTCATCT TATTATAAGA

1381 TTTGACGAAA ATGGAGTGCT ACTAAACAAT TCCTTCCTGG
     ACCCAGAATA TTGGAACTTT

1441 AGAAATGGAG ATCTTACTGA AGGCAACGCT GTTGGATTTA
     TGCCTAACCT ATCAGCTTAT

1501 CCAAAATCTC ACGGTAAAAC TGCCAAAAGT AACATTGTCA
     GTCAAGTTTA CTTAAACGGA

1561 GACAAAACTA AACCTGTAAC ACTAACCATT ACACTAAACG
     GTACACAGGA AACAGGAGAC

1621 ACAACTagtT TCTGCGTTGC GTCCCGCGGT GGGTCCTCCT
     GCTACgcggc cgctCCttcc
```

```
1681 GCATACTCTA TGTCATTTTC ATGGGACTGG TCTGGCCACA
     ACTACATTAA TGAAATATTT

1741 GCCACATCCT CTTACACTTT TTCATACATT GCCCAAGAAT
     AA.
```

The present invention also relates to the isolated or purified nucleic acid molecule described in FIG. 11 (the Ad5 fiberΔ-L16 DNA), and as set forth in SEQ ID NO:11, which encodes the Ad5 fiberΔ-L16 protein of the present invention, as described in FIG. 8 and as set forth in SEQ ID NO:8. This sequence harbors the deletion of nucleotides 1465 through 1476 (ACAGCCTATACA; SEQ ID NO:47) of the nucleic acid sequence encoding the wild-type Ad5 fiber protein. This nucleotide deletion corresponds to the deletion of amino acid residues TAYT (SEQ ID NO:45), described herein, which abrogates Ad5 fiber protein binding to CAR. In addition, this sequence contains the nucleic acid sequence encoding the L16 peptide ligand within the HI loop of the fiber knob. The nucleotide sequence of Ad5 fiberΔ-L16 is as follows, wherein the knob is underlined, the nucleotide codons flanking the deletion are double underlined, the nucleic acid sequence encoding the L16 peptide ligand is in italics, and the additional sequence variation accounting for the engineered restriction site to facilitate insertion of the nucleotide sequence encoding L16 into the fiber sequence and to maintain the wild-type sequence is in lowercase:

```
                                           (SEQ ID NO:11)
1    ATGAAGCGCG CAAGACCGTC TGAAGATACC TTCAACCCCG
     TGTATCCATA TGACACGGAA

61   ACCGGTCCTC CAACTGTGCC TTTTCTTACT CCTCCCTTTG
     TATCCCCCAA TGGGTTTCAA

121  GAGAGTCCCC CTGGGGTACT CTCTTTGCGC CTATCCGAAC
     CTCTAGTTAC CTCCAATGGC

181  ATGCTTGCGC TCAAAATGGG CAACGGCCTC TCTCTGGACG
     AGGCCGGCAA CCTTACCTCC

241  CAAAATGTAA CCACTGTGAG CCCACCTCTC AAAAAAACCA
     AGTCAAACAT AAACCTGGAA

301  ATATCTGCAC CCCTCACAGT TACCTCAGAA GCCCTAACTG
     TGGCTGCCGC CGCACCTCTA

361  ATGGTCGCGG GCAACACACT CACCATGCAA TCACAGGCCC
     CGCTAACCGT GCACGACTCC

421  AAACTTAGCA TTGCCACCCA AGGACCCCTC ACAGTGTCAG
     AAGGAAAGCT AGCCCTGCAA

481  ACATCAGGCC CCCTCACCAC CACCGATAGC AGTACCCTTA
     CTATCACTGC CTCACCCCCT

541  CTAACTACTG CCACTGGTAG CTTGGGCATT GACTTGAAAG
     AGCCCATTTA TACACAAAAT

601  GGAAAACTAG GACTAAAGTA CGGGGCTCCT TTGCATGTAA
     CAGACGACCT AAACACTTTG

661  ACCGTAGCAA CTGGTCCAGG TGTGACTATT AATAATACTT
     CCTTGCAAAC TAAAGTTACT

721  GGAGCCTTGG GTTTTGATTC ACAAGGCAAT ATGCAACTTA
     ATGTAGCAGG AGGACTAAGG

781  ATTGATTCTC AAAACAGACG CCTTATACTT GATGTTAGTT
     ATCCGTTTGA TGCTCAAAAC
```

-continued

```
 841 CAACTAAATC TAAGACTAGG ACAGGGCCCT CTTTTTATAA
     ACTCAGCCCA CAACTTGGAT

901 ATTAACTACA ACAAAGGCCT TTACTTGTTT ACAGCTTCAA
     ACAATTCCAA AAAGCTTGAG

961 GTTAACCTAA GCACTGCCAA GGGGTTGATG TTTGACGCTA
     CAGCCATAGC CATTAATGCA

1021 GGAGATGGGC TTGAATTTGG TTCACCTAAT GCACCAAACA
     CAAATCCCCT CAAAACAAAA

1081 ATTGGCCATG GCCTAGAATT TGATTCAAAC AAGGCTATGG
     TTCCTAAACT AGGAACTGGC

1141 CTTAGTTTTG ACAGCACAGG TGCCATTACA GTAGGAAACA
     AAAATAATGA TAAGCTAACT

1201 TTGTGGACCA CACCAGCTCC ATCTCCTAAC TGTAGACTAA
     ATGCAGAGAA AGATGCTAAA

1261 CTCACTTTGG TCTTAACAAA ATGTGGCAGT CAAATACTTG
     CTACAGTTTC AGTTTTGGCT

1321 GTTAAAGGCA GTTTGGCTCC AATATCTGGA ACAGTTCAAA
     GTGCTCATCT TATTATAAGA

1381 TTTGACGAAA ATGGAGTGCT ACTAAACAAT TCCTTCCTGG
     ACCCAGAATA TTGGAACTTT

1441 AGAAATGGAG ATCTTACTGA AGGCAACGCT GTTGGATTTA
     TGCCTAACCT ATCAGCTTAT

1501 CCAAAATCTC ACGGTAAAAC TGCCAAAAGT AACATTGTCA
     GTCAAGTTTA CTTAAACGGA

1561 GACAAAACTA AACCTGTAAC ACTAACCATT ACACTAAACG
     GTACACAGGA AACAGGAGAC

1621 ACAACTagtT TCTGCAAGGT CGTGGGTGGT GGTTCCTCCT
     GCTCCCCGgc ggccgctCCt 1681 tccGCATACT CTATGTCATT TTCATGGGAC TGGTCTGGCC
     ACAACTACAT TAATGAAATA

1741 TTTGCCACAT CCTCTTACAC TTTTTCATAC ATTGCCCAAG
     AATAA.
```

The present invention further relates to the isolated or purified nucleic acid molecule described in FIG. 12 (the Ad5 fiberΔ-L33 DNA), and as set forth in SEQ ID NO:12, which encodes the Ad5 fiberΔ-L33 protein of the present invention, as described in FIG. 9 and as set forth in SEQ ID NO:9. This sequence harbors the deletion of nucleotides 1465 through 1476 (ACAGCCTATACA; SEQ ID NO:47) of the nucleic acid sequence encoding the wild-type Ad5 fiber protein. This nucleotide deletion corresponds to the deletion of amino acid residues TAYT (SEQ ID NO:45), described herein, which abrogates Ad5 fiber protein binding to CAR. In addition, this sequence contains the nucleic acid sequence encoding the L33 peptide ligand within the HI loop of the fiber knob. The nucleotide sequence of Ad5 fiberΔ-L33 is as follows, wherein the knob is underlined, the nucleotide codons flanking the deletion are double underlined, the nucleic acid sequence encoding the L33 peptide ligand is in italics, and the additional sequence variation accounting for the engineered restriction site to facilitate insertion of the nucleotide sequence encoding L33 into the fiber sequence and to maintain the wild-type sequence is in lowercase:

(SEQ ID NO:12)
```
   1 ATGAAGCGCG CAAGACCGTC TGAAGATACC TTCAACCCCG
     TGTATCCATA TGACACGGAA

61 ACCGGTCCTC CAACTGTGCC TTTTCTTACT CCTCCCTTTG
     TATCCCCCAA TGGGTTTCAA

121 GAGAGTCCCC CTGGGGTACT CTCTTTGCGC CTATCCGAAC
     CTCTAGTTAC CTCCAATGGC

181 ATGCTTGCGC TCAAAATGGG CAACGGCCTC TCTCTGGACG
     AGGCCGGCAA CCTTACCTCC

241 CAAAATGTAA CCACTGTGAG CCCACCTCTC AAAAAAACCA
     AGTCAAACAT AAACCTGGAA

301 ATATCTGCAC CCCTCACAGT TACCTCAGAA GCCCTAACTG
     TGGCTGCCGC CGCACCTCTA

361 ATGGTCGCGG GCAACACACT CACCATGCAA TCACAGGCCC
     CGCTAACCGT GCACGACTCC

421 AAACTTAGCA TTGCCACCCA AGGACCCCTC ACAGTGTCAG
     AAGGAAAGCT AGCCCTGCAA

481 ACATCAGGCC CCCTCACCAC CACCGATAGC AGTACCCTTA
     CTATCACTGC CTCACCCCCT

541 CTAACTACTG CCACTGGTAG CTTGGGCATT GACTTGAAAG
     AGCCCATTTA TACACAAAAT

601 GGAAAACTAG GACTAAAGTA CGGGGCTCCT TTGCATGTAA
     CAGACGACCT AAACACTTTG

661 ACCGTAGCAA CTGGTCCAGG TGTGACTATT AATAATACTT
     CCTTGCAAAC TAAAGTTACT

721 GGAGCCTTGG GTTTTGATTC ACAAGGCAAT ATGCAACTTA
     ATGTAGCAGG AGGACTAAGG

781 ATTGATTCTC AAAACAGACG CCTTATACTT GATGTTAGTT
     ATCCGTTTGA TGCTCAAAAC

841 CAACTAAATC TAAGACTAGG ACAGGGCCCT CTTTTTATAA
     ACTCAGCCCA CAACTTGGAT

901 ATTAACTACA ACAAAGGCCT TTACTTGTTT ACAGCTTCAA
     ACAATTCCAA AAAGCTTGAG

961 GTTAACCTAA GCACTGCCAA GGGGTTGATG TTTGACGCTA
     CAGCCATAGC CATTAATGCA

1021 GGAGATGGGC TTGAATTTGG TTCACCTAAT GCACCAAACA
     CAAATCCCCT CAAAACAAAA

1081 ATTGGCCATG GCCTAGAATT TGATTCAAAC AAGGCTATGG
     TTCCTAAACT AGGAACTGGC

1141 CTTAGTTTTG ACAGCACAGG TGCCATTACA GTAGGAAACA
     AAAATAATGA TAAGCTAACT

1201 TTGTGGACCA CACCAGCTCC ATCTCCTAAC TGTAGACTAA
     ATGCAGAGAA AGATGCTAAA

1261 CTCACTTTGG TCTTAACAAA ATGTGGCAGT CAAATACTTG
     CTACAGTTTC AGTTTTGGCT

1321 GTTAAAGGCA GTTTGGCTCC AATATCTGGA ACAGTTCAAA
     GTGCTCATCT TATTATAAGA

1381 TTTGACGAAA ATGGAGTGCT ACTAAACAAT TCCTTCCTGG
     ACCCAGAATA TTGGAACTTT

1441 AGAAATGGAG ATCTTACTGA AGGCAACGCT GTTGGATTTA
     TGCCTAACCT ATCAGCTTAT

1501 CCAAAATCTC ACGGTAAAAC TGCCAAAAGT AACATTGTCA
     GTCAAGTTTA CTTAAACGGA
```

-continued

```
1561  GACAAAACTA AACCTGTAAC ACTAACCATT ACACTAAACG
      GTACACAGGA AACAGGAGAC

1621  ACAACTagtT TCTTCTGCGT TTCCGACGGT GGTGGTTCCT
      CCTGCCCGgc ggccgctCCt 1681  tccGCATACT CTATGTCATT TTCATGGGAC TGGTCTGGCC
      ACAACTACAT TAATGAAATA

1741  TTTGCCACAT CCTCTTACAC TTTTTCATAC ATTGCCCAAG
      AATAA.
```

The degeneracy of the genetic code is such that, for all but two amino acids, more than a single codon encodes a particular amino acid. This allows for the construction of synthetic or recombinant DNA that encode the specific modified Ad5 fiber proteins of the present invention where the nucleotide sequences of the synthetic or recombinant DNA differs significantly from the nucleotide sequences of SEQ ID NOs:4-6 but still encode the same modified Ad5 fiber proteins of SEQ ID NOs:1-3, respectively. Such synthetic or recombinant DNA are intended to be within the scope of the present invention. If it is desired to express such synthetic or recombinant DNA in a particular host cell or organism, the codon usage of such synthetic or recombinant DNA can be adjusted to reflect the codon usage of that particular host, thus leading to higher levels of expression of the modified Ad5 fiber protein in the host. In other words, this redundancy in the various codons which code for specific amino acids is within the scope of the present invention. Therefore, the present invention discloses codon redundancy which may result in differing DNA molecules expressing an identical protein.

As used herein, "purified" and "isolated" are utilized interchangeably to stand for the proposition that the nucleic acid, protein, or respective fragment thereof in question has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in pure quantities so as to afford the opportunity to generate polyclonal antibodies, monoclonal antibodies, amino acid sequencing, and peptide digestion. Therefore, the nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods while a chemically synthesized nucleic acid sequence is considered to be substantially purified when purified from its chemical precursors.

The present invention further relates to recombinant vectors that comprise the substantially purified nucleic acid molecules disclosed throughout this specification. These vectors may be comprised of DNA or RNA. For most cloning purposes, DNA vectors are preferred. Typical vectors include plasmids, modified viruses, bacteriophage, cosmids, yeast artificial chromosomes, and other forms of episomal or integrated DNA that can encode a modified adenovirus fiber protein. It is well within the purview of the skilled artisan to determine an appropriate vector for a particular gene transfer or other use.

The cloned nucleic acid encoding a modified adenovirus fiber protein obtained through the methods described above may be recombinantly expressed by molecular cloning into an expression vector (such as pcDNA3.neo, pcDNA3.1, pCR2.1, pBlueBacHis2 or pLITMUS28) containing a suitable promoter and other appropriate transcription regulatory elements, and transferred into prokaryotic or eukaryotic host cells to produce recombinant modified adenovirus fiber protein. Expression vectors are defined herein as DNA sequences that are required for the transcription of cloned DNA and the translation of their mRNAs in an appropriate host. Such vectors can be used to express DNA in a variety of recombinant hosts cells such as bacteria, blue green algae, plant cells, insect cells and mammalian cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Methods to determine the DNA sequence(s) that yields optimal levels of modified adenovirus fiber protein are well known in the art. Following determination of the DNA cassette yielding optimal expression, this modified adenovirus fiber protein nucleic acid construct is transferred to a variety of expression vectors (including recombinant viruses), including but not limited to those for mammalian cells, plant cells, insect cells, oocytes, bacteria and yeast cells.

Therefore, another aspect of the present invention includes host cells that have been engineered to contain and/or express DNA sequences encoding modified adenovirus fiber proteins of the present invention. Recombinant host cells may be prokaryotic or eukaryotic, including but not limited to, bacteria such as E. coli, fungal cells such as yeast, mammalian cells including, but not limited to, cell lines of bovine, porcine, monkey and rodent origin; and insect cells including but not limited to Drosophila and silkworm derived cell lines. Such recombinant host cells can be cultured under suitable conditions to produce modified adenovirus fiber protein. The expression vector may be introduced into host cells via any one of a number of techniques including but not limited to transformation, transfection, protoplast fusion, and electroporation. The expression vector-containing cells are individually analyzed to determine whether they produce modified adenovirus fiber protein. Identification of modified adenovirus fiber protein expressing cells may be done by several means, including but not limited to immunological reactivity with adenovirus fiber protein antibodies.

As noted above, an expression vector containing DNA encoding a modified adenovirus fiber protein may be used for expression of modified adenovirus fiber protein in a recombinant host cell. Therefore, another aspect of this invention is a process for expressing a modified adenovirus fiber protein in a recombinant host cell, comprising: (a) introducing a vector comprising the nucleic acid of a modified adenovirus fiber protein into a suitable host cell; and, (b) culturing the host cell under conditions which allow expression of said modified adenovirus fiber protein.

Following expression of a modified adenovirus fiber protein in a host cell, the modified adenovirus fiber protein may be recovered. Several protein purification procedures are available and suitable for use: purification from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography. In addition, modified adenovirus fiber protein can be separated from other cellular proteins by use of an immunoaffinity column made with monoclonal or polyclonal antibodies specific for adenovirus fiber protein.

In one embodiment, the nucleic acids of the present invention may be assembled into an expression cassette that comprises sequences designed to provide for efficient expression of the protein. The modified adenovirus fiber protein expression cassette is then inserted into a vector. The vector is preferably an adenoviral vector, although linear DNA linked to a promoter, or other vectors, such as adeno-associated virus or a modified vaccinia virus vector may also be used. Therefore, another aspect of this invention includes adenoviral vectors comprising the nucleic acid molecules encoding the modified adenovirus fiber proteins described herein in place of the wild-type fiber gene. These adenoviral vectors are characterized by having a non-functional E1 gene region, and preferably a deleted adenoviral E1 gene region. In addition, these vectors optionally have a non-functional or deleted E3 region. It is preferred that the adenovirus genome used be deleted of both the E1 and E3 regions (ΔE1ΔE3). The adenoviruses can be multiplied in known cell lines which express the viral E1 gene, such as 293 cells, or PER.C6® cells, or in cell lines derived from 293 or PER.C6® cell which are transiently or stablily transformed to express an extra protein. For examples, when using constructs that have a controlled gene expression, such as a tetracycline regulatable promoter system, the cell line may express components involved in the regulatory system. One example of such a cell line is T-Rex-293; others are known in the art.

For convenience in manipulating the adenoviral vector, the adenovirus may be in a shuttle plasmid form. This invention is also directed to a shuttle plasmid vector which comprises a plasmid portion and an adenovirus portion, the adenovirus portion comprising an adenoviral genome (minus the wild-type fiber protein gene) which has a deleted E1 and optional E3 deletion, and has an inserted expression cassette comprising a modified adenovirus fiber protein described in this specification. In preferred embodiments, there is a restriction site flanking the adenoviral portion of the plasmid so that the adenoviral vector can be easily removed. The shuttle plasmid may be replicated in prokaryotic cells or eukaryotic cells.

The adenoviral vector is introduced into an appropriate host cell via any one of a number of techniques including but not limited to transformation, transfection, protoplast fusion, and electroporation. Said host will generate infectious viral particles wherein the modified adenovirus fiber includes a peptide ligand which is specific for a cell surface binding site other than CAR on a target cell.

In one embodiment of the invention, the adenoviral vector comprising the modified adenovirus protein of the present invention will further comprise a passenger transgene. A passenger transgene can be any gene, and desirably is either a therapeutic gene or a reporter gene. Preferably, a passenger transgene is capable of being expressed in a cell in which the vector has been internalized. For instance, the passenger transgene can comprise a reporter gene, or a nucleic acid sequence which encodes a protein that can in some fashion be detected in a cell. The passenger transgene also can comprise a therapeutic gene, for instance, a therapeutic gene which exerts its effect at the level of RNA or protein. For instance, a protein encoded by a transferred therapeutic gene can be employed in the treatment of an inherited disease. The protein encoded by the therapeutic gene may exert its therapeutic effect by resulting in cell killing. For instance, expression of the gene in itself may lead to cell killing, as with expression of the diphtheria toxin A gene, or the expression of the gene may render cells selectively sensitive to the killing action of certain drugs.

Moreover, the therapeutic gene can exert its effect at the level of RNA, for instance, by encoding an antisense message or ribozyme, a protein which affects splicing or 3' processing (e.g., polyadenylation), or can encode a protein which acts by affecting the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation. Accordingly, the use of the term "therapeutic gene" is intended to encompass these and any other embodiments of that which is more commonly referred to as gene therapy and is known to those of skill in the art. Similarly, the recombinant adenovirus can be used for gene therapy or to study the effects of expression of the gene in a given cell or tissue in vitro or in vivo.

"Gene therapy" is the treatment of pathologic conditions by the addition of exogenous nucleic acids to appropriate cells within the organism. Nucleic acids must be added to the cell, or transduced, such that they remain functional within the cell. For most gene therapy strategies, the new nucleic acids are designed to function as new genes, i.e., code for new messenger RNA that in turn codes for new protein. Nucleic acids useful for gene therapy include those that code for proteins used to identify cells infected with the recombinant virus, those that encode for proteins that function to kill cells containing the viral genome, or that encode for therapeutic proteins that will serve to treat a pathophysiologic condition within the body.

Another aspect of the present invention is a phage-display library of recombinant phage, wherein each recombinant phage displays on its outer surface a fusion protein which comprises a phage coat protein fused to a modified knob domain of an adenovirus fiber protein. The modified fiber knob, including but not limited to an Ad5 fiber knob domain, contains a peptide ligand comprising a core amino acid sequence of 14 potential residue positions wherein residue positions one, two and thirteen are Xaa residues, preferably tyrosine (Tyr), tryptophan (Trp), or phenylalanine (Phe); residue positions three and twelve are cysteine (Cys) residues; residue positions four through eleven are Xaa residues, preferably glycine (Gly), serine (Ser), or valine (Val); and, residue position fourteen is an Xaa residue, preferably proline (Pro). A portion of the modified fiber knobs contain a peptide ligand for a cell surface binding site other than CAR. The core amino acid sequence may be deleted by one or more residues at any residue position within the sequence, except at the Cys residues at position three and position twelve. It is preferable that the region of the core amino acid sequence located between the fixed Cys residues comprises at least two amino acid residues. The number of empty amino acid residue positions varies according to the frequency at which deletion of codon is introduced at each position during oligonucleotide synthesis. Additionally, up to 10 amino acid residues may be added between residue position three and residue position twelve. The amino acid sequence of the peptide ligand does not comprise a consecutive Arg-Gly-Asp (RGD) sequence between residue positions three and twelve, and the peptide ligand does not consist of the amino acid sequence as disclosed in SEQ ID NO:46.

Figure 13:
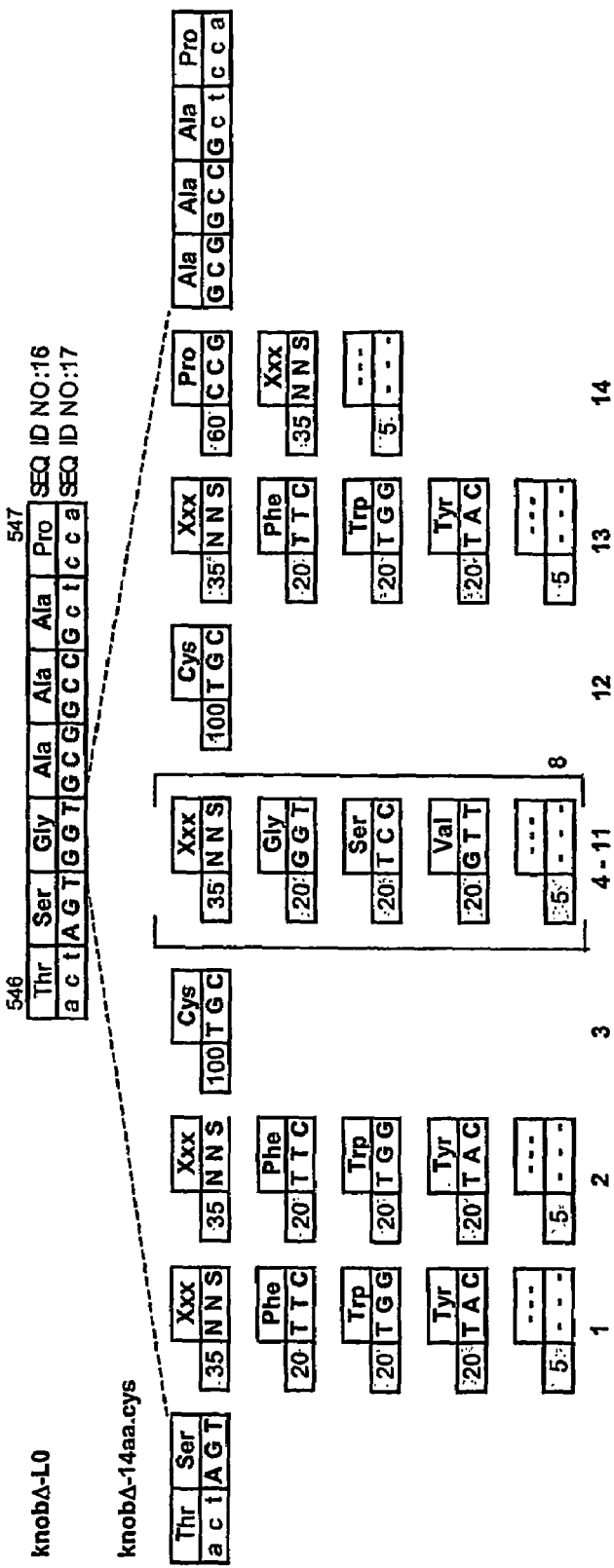
FIG. 13 depicts the structure of the λknobΔ-14aa.cys phage display library. The upper part of the figure refers to the portion of knobΔ-L0 sequence between amino acid positions 546 and 547 of the wild-type Ad5 fiber gene. Amino acid residues are indicated with a three-letter code. In knobΔ-L0, nucleotides are added between the codon sequences encoding the threonine (Thr) at position 546 and the proline (Pro) at position 547. The additional nucleotides engineer SpeI and NotI restriction sites into this region, facilitating the insertion of the candidate peptide ligands within the fiber knob. The added nucleotides are bolded and capitalized, and the additional amino acid residues they encode are in bold. SEQ ID NO:16 represents the amino acid sequence fragment of the region of knobΔ-L0 that includes residues 546 and 547 of the fiber protein sequence plus the new residues added between them. SEQ ID NO:17 represents the nucleotide sequence fragment of the region of knobΔ-L0 that includes the codon sequences encoding amino acid residues 546 and 547 of the fiber protein and the new nucleotides added between them.

Another embodiment of the present invention is a phage-display library of recombinant phage, wherein each recombinant phage displays on its outer surface a fusion protein which comprises a phage coat protein fused to an adenovirus fiber knob containing at least one of the variety of peptide ligands diagrammed in FIG. 13. A portion of the recombinant phage displays a modified fiber knob, including but not limited to an Ad5 fiber knob domain, containing a peptide ligand for a cell surface binding site other than CAR comprising a core amino acid sequence of 14 residue positions wherein residue positions one, two and thirteen are Xaa residues, preferably tyrosine (Tyr), tryptophan Trp), or phenylalanine (Phe); residue positions three and twelve are cysteine (Cys) residues; residue positions four through eleven are Xaa residues, preferably glycine (Gly), serine (Ser), or valine (Val); and, residue position fourteen is an Xaa residue, preferably proline (Pro). The core amino acid sequence may be deleted by one or more residues at any residue position within the sequence, except at the Cys residues at position three and position twelve. It is preferable that the region of the core amino acid sequence located between the fixed Cys residues comprises at least two amino acid residues. In this embodiment, the amino acid sequence of the peptide ligand does not comprise a consecutive Arg-Gly-Asp (RGD) sequence between residue positions three and twelve, and the peptide ligand does not consist of the amino acid sequence as disclosed in SEQ ID NO:46.

The modified fiber knobs contained within a phage-display library of the present invention, including but not limited to modified Ad5 fiber knobs, contain at least one of the variety of peptide ligands as described above. These peptide ligands represent the pool of candidate peptides that have the potential of binding cell surface attachments sites other than CAR when presented in a knob context. The method used to generate the candidate peptide ligands included within a phage-display library described herein is described in Example 3 of this specification. The candidate peptide ligands to be expressed in a phage library described herein are inserted within the fiber knob such that the expressed peptide ligands are accessible to a potential cell surface binding site. Since trimer formation of the modified fiber knob must be retained, a preferred location in which to insert the candidate peptide ligands is within an exposed loop domain of the knob. Thus, in one embodiment, the modified fiber knobs displayed in a phage library of the present invention comprise candidate peptide ligands as described herein which are inserted within an exposed loop domain of the knob, including but not limited to the HI loop domain. If the fiber knob is from Ad5, the candidate peptide ligands can be inserted between amino acid residue 546 and amino acid residue 547 located within the fiber knob of the Ad5 fiber protein. In a further embodiment of the invention, the modified fiber knobs displayed in a phage library of the present invention are further modified to abolish the wild-type cell surface binding of the knob domain. One method by which to ablate the wild-type CAR binding of an adenovirus fiber knob is to alter the fiber knob sequence, e.g., deleting the four-amino acid sequence TAYT (SEQ ID NO:45) within the Ad5 fiber knob located from residues 489-492.

In a further embodiment of the invention, the phage-display libraries described in this specification are displayed on bacteriophage λ, wherein the modified fiber knob is fused to the major head D protein of λ phage. The phage-display libraries of the present invention overcome the limitations of prior phage-display peptide libraries used to identify peptide ligands possessing an altered binding specificity when incorporated into adenovirus fibers because the candidate peptide ligands are expressed within a functional fiber knob in the phage-display system. By using the phage-display system of the present invention, the potential peptide ligands are surveyed in the fiber knob context. In filamentous phage display systems, the fusion protein is transported into and folds within the oxidizing environment of the periplasmic spaces. Phage particles assemble here before being secreted from the cell. By contrast, in the bacteriophage λ system, fusion protein folding and phage particle assembly takes place in the reducing milieu of the cytoplasm, prior to lysis of the bacterial host. These latter conditions more closely resemble those experienced by adenovirus fibers which assemble in the reducing environment of the mammalian cell nucleus before lysis of the cell. Namely, altered redox status might affect folding and binding properties of the modified knobs. Accordingly, in a further embodiment of the invention, the libraries described herein are displayed on bacteriophage λ, wherein the phage coat protein to which the modified adenovirus fiber knob is fused includes, but is not limited to, the λ major head D protein. Generating a phage-display library which expresses a high complexity of peptide ligands located within the adenovirus fiber domain combines the high-throughput screening potential of phage libraries with peptide ligand expression in the fiber knob context. It also makes eliminating peptide ligand sequences that interfere with fiber protein trimerization feasible.

Accordingly, another aspect of the present invention is a process for identifying a peptide ligand for a cell specific binding site other than CAR, comprising: (a) providing a phage-display library described above; and (b) screening that library on CAR-negative or CAR-positive cells. Essentially, the library can be screened on any cell type. When panning on CAR-positive cells, however, it is likely that the binding to CAR will eliminate the possibility to identify ligands for alternative receptors. This problem can be solved by two methods. First, the library can be built in a fiber knob harboring a mutation that ablates binding to CAR. This method was used to screen the library exemplified in this specification (see Example 4) in which three novel peptide ligands (SEQ ID NOs:13, 14 and 15; corresponding to peptide ligands L1, L16 and L33, respectively) that bind to cell surface binding sites other than CAR were identified. These peptide ligands faithfully retain their specificity when incorporated into the Ad5 genome. Recombinant adenoviruses comprising the novel peptide ligands have an enhanced ability to infect NIH3T3 cells compared to parental vector. This non-native tropism is mediated by the interaction of the virus knob with an unknown receptor on the target cell. This CAR-independent tropism can be activated in different cell-types from various species, with no relation to CAR expression. These results support this strategy as a general methodology for altering adenovirus tropism and widening its therapeutic window for different gene transfer applications. An alternative method of screening for novel peptide ligands is to generate a library with intact CAR binding but screening said library in the presence of an excess of competing wild-type knob protein.

To this end, the present invention also relates to methods of increasing the ability of an adenovirus to transduce a specific cell-type or tissue. A recombinant adenovirus of the present invention can be used to transduce cell-types or tissues that either do not express the wild-type adenovirus fiber protein surface receptor or express only low quantities of said surface receptor, including but not limited to synoviocytes, smooth muscle cells, endothelial cells, cancer cells, primary tumors, dendritic cells, skeletal muscle, melanocytes and murine melanoma cells. As long as the wild-type tropism of a recombinant adenovirus of the present invention has not been ablated, as described in this specification, a recombinant adenovirus of the present invention can also be used to transduce cell-types or tissues that express the wild-type adenovirus fiber protein surface receptor, alone, or in combination with the cell specific surface receptor of the peptide ligand located within the modified fiber protein. Using a recombinant adenovirus of the present invention to transduce cells expressing wild-type adenovirus fiber protein surface receptors in combination with the cell specific surface receptors for the peptide ligands described herein may help to achieve a more efficient adenoviral infection.

One embodiment of the present invention includes a method of transducing immature dendritic cells (DC), including but not limited to immature dendritic cells of mouse or human origin, which express low levels of CAR. Dendritic cells are key antigen-presenting cells (APCs) that play a pivotal role in the regulation of antigen-specific immune responses (Jonuleit et al., *Trends Immunol.* 22:394-400 (2001); Banchereau et al., *Nature* 392:245-252 (1998)). Genetic modification of DCs has considerable therapeutic potential as a route to modulate DC function, as well as for the treatment of a wide spectrum of diseases, including cancer and persistent viral infection (Nair, *Gene Ther.* 5:1445-1446 (1998)). In another embodiment, the recombinant adenoviruses of the present invention are used to transduce skeletal muscle, including but not limited to murine skeletal muscle, and primary melanocytes, including but not limited to primary melanocytes of human origin, both of which express low quantities of CAR.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples are provided to illustrate the present invention without, however, limiting the same hereto.

EXAMPLE 1

Display of Ad5 Trimeric Knob Domain on the Capsid of Phage λ

Cells—*E. coli* strains BB4 and Y1090 were used for phage plating and amplification.

Construction of plasmid pDknob—Plasmid pNS3785 (Sternberg and Hoess, 1995, *Proc. Natl. Acad. Sci. USA* 92:1609-1613) was transformed into pDknob by modifying the 3'-end of the λD gene as indicated in FIG. 14.

An XbaI restriction site was introduced into plasmid pNS3785 to allow cloning of the entire plasmid into the unique XbaI site of lambda Dam15imm21nin5. Plasmid pNS3785 was amplified by inverse PCR using primers XbaI-NS.for (5'-TTTA TCTAGACCCAGCCCTAGGAAGCTTCTCCTGAGTAG GACAAATCC-3'; SEQ ID NO:20) and XbaI-NS.rev (5'-GGG TCTAGATAAAACGAAAGGCCCAGTCTTTC-3'; SEQ ID NO:21) (XbaI site underlined). Reaction was performed using a mixture of Taq and Pfu DNA polymerases to increase fidelity of DNA synthesis (95° C.-30 sec, 55° C.-30 sec, 72° C.-20 min, for 25 amplification cycles). The PCR amplification product thus generated was digested with XbaI endonucleases and ligated to generate the plasmid pD-XbaI.

A 65 bp dsDNA fragment containing a ribosome binding site (RBS) and a KpnI site (underlined) was obtained by annealing the oligonucleotides link-SD.s (5'-GAC-CGCGTTTGCCGGAACGGCAATCAG-CATCGTTGGTTCCGGCTCTGGTAAGGA GGTACCGTAGG-3'; SEQ ID NO:22) and link-SD.as (5'-AATTCCTACGGTACCTCCTTACCAGAGC-CGGAACCAACGATGCTGATTGCCGTT-3'; SEQ ID NO:23). This DNA fragment was cloned into plasmid pKM3 at the 3' end of the lambda D gene, between the RsrII and EcoRI restriction sites, generating the plasmid pD-linker.

The DNA sequence coding for Ad5 fiber knob domain was PCR amplified from plasmid pAB26 (Bett et al., 1993, *J. Virol.* 67:5911-5921) using D-fbr.for (5'-TAGGGTACCG-TAGATGGGTGCCATTACAGTAGGAAACAAAA-3'; SEQ ID NO:24) and D-fbr.rev (5'-AAAGAATTCTTTAT-TCTTGGGCAATGTATG-3'; SEQ ID NO:25) primers. The resulting 600 bp fragment was digested with KpnI and EcoRI restriction enzymes and inserted in plasmid pD-linker at the 3' end of the lambda D gene between the corresponding sites, generating the plasmid pDknob_linker0. Linker sequences containing multiple Gly-Ser (GS) repeats were inserted between the D and the knob gene in the plasmid pDknob_linker0. A dsDNA fragment coding for 2.5 GS repeats and containing a BamHI site was obtained by annealing the oligonucleotides BamHI-link.s (5'-GAC-CGCGTTTGCCGGAACGGCAATCAG-CATCGTTGGATCCGGTTCTGGTAAGGAGG TAC-3'; SEQ ID NO:26) and BamHI-link.as (5'-CTCCTTACCA-GAACCGGATCCAACGATGCTGATTGC-CGTTCCGGCAAACGCG-3'; SEQ ID NO:27). This 59 bp DNA fragment was inserted between the RsrII and KpnI sites of plasmid pDknob_linker0 to create plasmid pDknob_Blinker.

dsDNA of different lengths were generated by annealing the oligonucleotides GS-link.s (5'-GATCTGGTTCCGGT-TCTGGCTCCGGCTCTGGTTCTGGTTCCG-3'; SEQ ID NO:28) and GS-link.as (5'-GATCCGGAACCAGAACCA-GAGCCGGAGCCAGAACCGGAACCA-3'; SEQ ID NO:29), promoting the formation of polymeric products. By cloning this mixture in the BamHI site of plasmid pDknob_Blinker, three plasmids were identified which contained one (pDknob_linker1) or two inserts (pDknob_linker2). The latter was used in the described experiments and referred to pDknob.

Construction of plasmid pDknob.Δ—The DNA sequence of Ad5 fiber knob was PCR amplified from plasmid pAB26 (Bett et al., 1993, supra) using Nhe-fbr.for (5'-GTTTTGACGCTAGCGGTGCCATTACAGTAGGAAAC-3'; SEQ ID NO:30) and D-fbr.rev (5'-AAAGAATTCTTTAT-TCTTGGGCAATGTATG-3'; SEQ ID NO:25) primers. The 600 bp fragment was digested with NheI and EcoRI restriction enzymes and cloned into the NheI and EcoRI sites of pTRCHisB vector (Invitrogen, Groningen, The Netherlands), generating plasmid pHis.knob.

The construct pHis.knobΔ, containing the coding sequence of the fiber knob deleted of the amino acids TAYT (SEQ ID NO:45), was obtained by cloning into the vector pHis.knob digested with MscI/BglII a PCR product amplified with the primers knobΔ (5'-GGAGATCTTACTGAAGGCAACGCT-GTTGGATTTATG-3'; SEQ ID NO:31) and pD.rev (5'-TCT-GATTTAATCTGTATCAGGCTG-3'; SEQ ID NO:32) from the plasmid pDknobΔ.SN-Cterm and digested with BglII and MscI restriction enzymes. The plasmid pDknobΔ.SN-Cterm was obtained by cloning into the vector pDknob digested with MscI/EcoRI a PCR fragment obtained from pDknob using the primers knob-for3 (5'-CCAAGTGCATACTCTATGT-CATTTT-3'; SEQ ID NO:33 ) and knobC-Spe/Not.rev (5'-TCGAATTCTTTAAGCGGCCGCACCAC-TAGTTTCTTGGGCAATGTATGAAAA-3'; SEQ ID NO:34) and digested with MscI/EcoRI enzymes.

A PCR fragment was obtained from the plasmid pHisknobΔ using the primers knobΔ (5'-GGAGATCTTACT-GAAGGCAACGCTGTTGGATTTATG-3'; SEQ ID NO:31)/D-fbr.rev(5'-AAAGAATTCTTTATTCT-TGGGCAATGTATG-3'; SEQ ID NO:25). This PCR product was digested with EcoRI and BglII restriction enzymes and inserted in the corresponding sites of vector pDknob to replace the wt sequence. The resulting plasmid, pDknobΔ, contains the TAYT (SEQ ID NO:45) deletion in the fiber knob gene which abrogates CAR binding.

Generating phage lambda-knob and lambda-knobΔ—Plasmids pDknob and pDknob.Δ were linearized by digestion with XbaI restriction enzyme and the entire plasmid was cloned into the unique XbaI site of λ phage Dam15imm21nin5 generating phage λknob-wt and λknobΔ-wt, respectively. After overnight incubation at 4° C. the ligation mixture was packaged in vitro using lambda packaging kit (APB, Uppsala, Sweden) and plated with top-agar on NZY-agar plates. Positive clones were identified by PCR, amplified and purified as described in Sambrook et al., 1989, supra. All pD derivatives generated the corresponding λ phage.

Antibodies—Rabbit anti-knob R330 and anti-λ sera were obtained by immunizing New Zealand rabbits with bacterially expressed recombinant Ad5 knob protein and λ phage particles, respectively, according to standard protocol. By screening a panel of human sera, a sample that reacted with both the monomeric and trimeric (serum N92), or specifically with the trimeric (serum N93), form of the bacterially expressed recombinant Ad5 fiber knob were identified. Antibodies from serum R330, anti-λ (Ab anti-λ) and N92 (AbN92), were purified on Protein-A Sepharose (Amersham-Pharmacia, Little Chalfont, UK) according to manufacturer's instructions. Antibodies from serum N93 (AbN93) were affinity-purified on recombinant knob protein. Mouse mAb12D6 (provided by Frank Graham of McMaster University, Hamilton, Ontario, Canada) selectively recognizes Ad5 knob trimer.

Viruses—The recombinant adenoviruses were propagated on Per.C6 cells and purified by centrifugation in CsCl gradients according to standard protocols (Fallaux et al, 1998, *Hum. Gene Ther.* 9:1090-1917).

Phage-ELISA—Multi-well plates (Nunc, Roskilde, Denmark) were coated overnight at 4° C. with goat anti-human IgG Fc-specific (Pierce, Rockford, Ill.) or with anti-mouse IgG-specific (SIGMA, St. Louis, Mo.) at a concentration of 2.2 μg/ml or 5 μg/ml, respectively, in 50 mM $NaHCO_3$ (pH 9.6). After discarding the coating solution, plates were incubated at 37° C. for 60 min with washing buffer composed of 5% non-fat dry milk in phosphate buffered saline solution (PBS) containing 0.05% Tween-20 (PBST). Blocking solution was discarded and AbN93, AbN92 or mAb12D6, in blocking buffer, were added and allowed to bind for 2 hours at room temperature (RT). Plates were washed with PBST and about $1\times10^9$ pfu of phage lysate in binding buffer (5% non-fat dry milk in PBS) were incubated for 4 hours at RT. Plates were then washed with PBS, and captured phage particles were detected by anti-λ polyclonal antibody in binding buffer for 2 hours at RT. After washing with PBS, plates were incubated in an anti-rabbit IgG alkaline phosphatase conjugated antibody (Sigma, St. Louis, Mo.) in binding buffer for 2 hours at RT. Plates were then washed, and alkaline phosphatase activity was detected by incubation with Sigma 104 phosphatase substrate (SIGMA, St. Louis, Mo.) in diethanolamine. Plates were read by an automated ELISA reader (Labsystems Multiskan Bichromatic, Helsinki, Finland).

Results—A bacterial expression plasmid was engineered to direct the synthesis of a bi-cistronic system composed of the gene coding for the major head D protein of bacteriophage λ upstream of the gene coding for the Ad5 fiber knob domain. The vector was designed to add a $(Gly-Ser)_{16}$ peptide linker at the C-terminus of the D protein, followed by a ribosome-binding site, a D gene amber translation codon TAG, and an Ad5 knob gene methionine initiator codon (FIG. 14). By testing polymers of different lengths, a $(Gly-Ser)_{16}$ linker sequence was found to ensure the most efficient expression of the knob trimer on the lambda capsid and was adopted for further studies.

Plasmid pDknob was inserted into the XbaI site of the λDam15imm21nin5 genome, which contains a genomic copy of the D gene with an amber mutation. Following transformation in a suppressor bacterial host, the resulting phage, λknob-wt, is anticipated to express: (i) the wt D protein encoded by the λ genomic D gene (D); (ii) the recombinant wt D protein encoded by the plasmid D gene (reD); (iii) the reD-knob fusion (as a result of bacterial suppression), and (iv) the knob protein (by translational re-initiation). Phage particles should display a chimeric array of D, reD and fusion reD-knob protein on their capsids. In addition, since both the D and the knob protein form homotrimeric complexes, the conditional fusion between reD and knob should permit knob trimers to be assembled on the λ capsid. Monoclonal (mAb12D6) or polyclonal (AbN93) antibodies that selectively recognize the Ad5 homotrimeric knob structure specifically reacted with λknob-wt lysate in a phage enzyme-linked immunosorbent assay (ELISA), indicating that knob trimers were efficiently displayed on the capsid of the phage particle (FIG. 15).

The deletion of Ad5 fiber TAYT (SEQ ID NO:45) residues (residue position 489 to 492 of the knob DG loop) completely abrogates the high affinity binding of Ad5 fiber to CAR (Roelvink et al., 1999, supra). The corresponding λknobΔ-wt derivative specifically reacted with anti-homotrimeric knob antibodies, indicating that this modified knob was also displayed as a homotrimer on the phage capsid (FIG. 15).

Finally, λwt and λNS3 (a negative-control clone expressing on its surface the 80 amino acids from the NS3 protein of hepatitis C virus) showed only background levels of binding.

EXAMPLE 2

λ-borne Ad5 Knob Specifically Binds Human CAR on 911 Cells

Cells—Human embryonic retinoblast 911 cells were obtained from Invitrogen (Rijswijk, The Netherlands). 911 cells were cultured in Dulbecco's modified Eagle's medium (DMEM) supplemented with 10% (v/v) fetal calf serum (FCS).

Viruses—The recombinant adenoviruses were propagated on Per.C6 cells and purified by centrifugation in CsCl gradients according to standard protocols (Fallaux et al, 1998, supra).

FACS Analysis—Binding of phage λknob-wt to human CAR displayed on the surface of 911 cells was monitored as follows. Phage particles (ranging from $0.4\times10^{10}$ to $6\times10^{10}$ pfu) were incubated with a suspension of $2\times10^6$ cells/ml for 1 hour at room temperature (RT) in binding buffer composed of 3% bovine serum albumin (BSA), 10 mM $MgCl_2$, 1 mM $CaCl_2$ in PBS. Cells were washed with binding buffer and incubated for 45 min at 4° C. with rabbit anti-λ purified Ig in FACS buffer (2% FBS in PBS). Cells were then washed with FACS buffer and incubated for 45 min at 4° C. in FACS buffer containing goat anti-rabbit IgG PE-conjugated (Diamedix, Miami, Fla., U.S.A.). After washing with FACS buffer, cells were resuspended at about $6 \times 10^5$ cells/ml in FACS buffer and analyzed by a FACSCalibre flow cytometer (Beckton Dickinson, Oxford, UK). Fluorescence intensity was analyzed by CELLQuest software.

In the competition experiment, cells were pre-incubated with 200 µl of binding buffer containing 10 µg/ml of recombinant His-tagged knob protein fiber (or a His-tagged unrelated protein) for 30 min at RT. To this mixture, phage ($6 \times 10^{10}$ pfu) were added without removing the unbound protein and incubated for an additional 60 min. Goat anti-rabbit IgG FITC-conjugated antibody (Pierce, Rockford, Ill.) was used as the secondary antibody.

Results—To validate the functionality of the phage-displayed knob, λknob-wt virions were incubated with human embryonic retinoblast 911 cells which express high levels of CAR on their surface. CAR-specific binding was assayed by fluorescence-activated cell sorting (FACS) analysis. λknob-wt phage particles bound to 911 cells, as indicated-by the variation in distribution of fluorescent-labeled cells (FIG. 16A). Increasing phage titers linearly increased the amount of bound phage, as measured by the median fluorescence of cells. In contrast, neither λwt nor λNS3 showed detectable levels of binding. Similarly, incubating 911 cells with λknobΔ-wt phage did not reveal any cell binding. Binding of λknob-wt to 911 cells was inhibited by incubation with an excess of recombinant knob, whereas incubation with the unrelated protein NS3 did not produce any effects (FIG. 16B). The same reagents did not vary the binding activity of λwt phage.

EXAMPLE 3

Generating a Library of Modified Ad5 Fiber Knobs Displayed on λ

Viruses—The recombinant adenoviruses were propagated on Per.C6 cells and purified by centrifugation in CsCl gradients according to standard protocols (Fallaux et al, 1998, supra).

Construction of the λknobΔ-14aa.cys library—Plasmid pDknobΔ-L0 was generated by replacing the BglII/MscI fragment in pD-knobΔ with a PCR amplification product introducing unique SpeI and NotI sites in the HI loop. Two 326 bp and 93 bp DNA fragments were obtained by PCR-amplifying the plasmid pDknob using the primers knob.for2 (5'-AGGCAGTTTGGCTCCAATATCTG-3'; SEQ ID NO:35) and knobHI-Spe/Not.rev (5'-GCGGCCGCACCAC-TAGTTGTGTCTCCTGTTTCCTGTGTA-3'; SEQ ID NO:36), or knobHI-Spe/Not.for (5'-ACTAGTGGTGCGGC-CGCTCCAAGTGCATACTCTATGTCATTT-3'; SEQ ID NO:37) and knob.rev3 (5'-GGATGTGGCAAATATTTCAT-TAAT-3'; SEQ ID NO:38). These DNA fragments were PCR-ligated. The resulting plasmid pDknobΔ-L0 was linearized by XbaI digestion and the entire plasmid was cloned into the unique XbaI site of λDam15imm21nin5. The phage λknobΔ-L0 thus generated was amplified and CsCl purified. DNA was extracted from lambda particles and used for the library construction.

The library oligonucleotides were synthesized according to the splitting synthesis protocol (Glaser et al., 1992, *J. Immunol.* 149:3903-3913), converted into dsDNA by primer elongation, SpeI/NotI digested, and ligated into the corresponding SpeI/NotI sites of λknobΔ-L0. The ligation mixture was packaged in vitro (APB, Uppsala, Sweden) and plated on NZY-agar plates. After overnight incubation, phage was eluted from plates with SM buffer (50 mM Tris-HCl pH 7.5, 0.01% gelatin, 10 mM $MgSO_4$, 100 mM NaCl), purified, concentrated and stored at −80° C. in SM buffer, 7% DMSO. The complexity of the λknob-14aa.cys library was $1.6 \times 10^5$, as estimated from the number of individual plaques obtained by plating the packaging mixture. Sequence analysis of twenty clones randomly chosen confirmed the expected nucleotide in all the clones.

Results—The λknob display system was employed for generating and screening a large collection of candidate peptide ligand sequences within the framework of the knob domain. To eliminate the interference of CAR binding in screening for non-native tropism, the library was built in the λknobΔ-wt vector. The HI loop of the knob domain was chosen as the site for inserting foreign peptide ligand sequences and unique SpeI and NotI restriction sequences were introduced to facilitate peptide ligand insertion. As a result of these manipulations, the derivative λknobΔ-L0 incorporated the extra-peptidic sequence SGAAA (SEQ ID NO:39) between T546 and P547 of the wild-type Ad5 protein sequence (top panel of FIG. 13).

Oligonucleotides were synthesized by a resin splitting methodology to code for 14 amino acid residues flanked by SpeI and Not I restriction sites (FIG. 13). The peptide ligand sequences were constrained by incorporating two unvarying Cys residues at positions 3 and 12. Positions 1, 2 and 13 were biased for the presence of aromatic amino acids to favor interaction with hydrophobic receptor structures. Proline, which tends to adopt an extended structure, was favored at position 14 to increase accessibility of the inserted peptide ligand. The remaining 4 to 11 positions were designed to preferentially host amino acids with small lateral chains (glycine, serine or valine) to increase the loop flexibility. Finally, further variation was introduced by deleting 5% of codons at each position, except those coding for the fixed cysteines. Elongating these oligonucleotides with a suitable primer generated a dsDNA fragment, which was SpeI and NotI restricted and cloned into the corresponding sites of the vector λknobΔ-L0. In vitro packaging and plating of the ligation mixture generated the λknobΔ-14aa.cys library composed of $2 \times 10^5$ independent clones.

EXAMPLE 4

Screening Library λknobΔ-14aa.cys Library for Peptide Ligand Binding to NIH3T3 Cells Bacteria—*E. coli* strains BB4 and Y1090 were used for phage plating and amplification.

Cells—Mouse fibroblast NIH3T3 cells were obtained from the American Type Culture Collection (ATCC, Rockville, Md., U.S.A.). The cells were cultured in Dulbecco's modified Eagle's medium (DMEM). All media were supplemented with 10% (v/v) fetal calf serum (FCS).

Panning library on cells—NIH3T3 cells were seeded at $2 \times 10^6$ cells in a 60 mm diameter Petri dish and incubated in culture medium at 37° C. with 5% $CO_2$ for 48 hours. Confluent cells were then starved by incubation with 5 ml blocking buffer (3% BSA, 10 mM $MgCl_2$, 1 mM $CaCl_2$ in PBS) for 1 hr at 37° C. The solution was then discarded and $5 \times 10^9$ pfu of phage library in 1 ml of blocking buffer was added and incubated for 3 hrs at 37° C. Unbound phage were removed, and cells were extensively washed with blocking buffer. Bound phage were then propagated by infecting bacteria The phage pool derived from this first round of selection was purified as described (Beghetto et al., 2001, *Int. J. Parasitol.* 31:1659-1668).

FACS analysis—Binding of lambda phage to NIH3T3 cells was analyzed using a FACS-based assay. A suspension of $2\times10^6$ cells/ml was incubated in binding buffer composed by 3% bovine serum albumin (BSA), 10 mM $MgCl_2$, 1 mM $CaCl_2$ in PBS, containing $2\times10^9$ pfu phage, for 60 min at 37° C. Cells were washed with binding buffer and incubated for 45 min at 4° C. with rabbit anti-λ purified Ig in FACS buffer (2% FBS in PBS). Cells were then washed with FACS buffer and incubated for 45 min at 4° C. in FACS buffer containing a goat anti-rabbit IgG PE-conjugated antibody (Diamedix, Miami, Fla., U.S.A.). After washing with FACS buffer, cells were resuspended at about $6\times10^5$ cells/ml in FACS buffer and analyzed by a FACSCalibre flow cytometer (Beckton Dickinson, Oxford, UK). Fluorescence intensity was analyzed by CELLQuest software.

Immunological screening of recombinant A clones—Phage plaques were generated as described and transferred onto nitrocellulose filters (Schleicher & Schuell GmbH, Dassel, Germany) (Beghetto, E. et al., 2001, supra). Filters were first saturated with blocking buffer (5% non-fat dry milk in PBS, 0.01% Triton) for 1 h at RT. The filters were then incubated with human AbN93 or rabbit R330 anti-knob antibodies (see Example 1 for antibody descriptions) diluted in blocking buffer for 2 hours at room temperature (RT). After washing several times with PBST, an alkaline phosphatase conjugated secondary antibody (anti-human-IgG or anti-rabbit IgG) was diluted in blocking buffer and incubated with the filters for 1 hour at RT. Positive phage plaques were finally visualized by developing the filters with chromogenic substrates (nitroblue tetrazolium and 5-bromo-chloro-3-indolyl phosphate substrates) (Sigma, St. Louis, Mo.).

Expression and purification of recombinant Ad fiber knob—The DNA sequence of Ad5 fiber knob was PCR amplified from plasmid pAB26 (Bett et al., 1993, supra) using Nhe-fbr.for (5'-GTTTTGACGCTAGCGGTGCCATTA-CAGTAGGAAAC-3'; SEQ ID NO:30) and D-fbr.rev (5'-AAAGAATTCTTTATTCTTGGGCAATGTATG-3'; SEQ ID NO:25) primers. The 600 bp fragment was digested with NheI and EcoRI restriction enzymes and cloned into the NheI and EcoRI sites of pTRCHisB vector (Invitrogen, Groningen, The Netherlands), generating plasmid pHis.knob. By cloning into pHis.knob, the appropriate PCR amplification products from pDknobΔ and pDknobΔ-L0, plasmids pHis.knobΔ and pHis.knobΔ-L0, were generated.

The construct pHis.knobΔ, containing the coding sequence of the fiber knob deleted of the amino acids TAYT (SEQ ID NO:45), was obtained by cloning into the vector pHis.knob cut with MscI/BglII. A PCR product was amplified with the primers knobΔ (5'-GGAGATCTTACTGAAGGCAACGCT-GTTGGATTTATG-3'; SEQ ID NO:31) and pD.rev (5'-TCT-GATTTAATCTGTATCAGGCTG-3'; SEQ ID NO:32) from the plasmid pDknobΔ.SN-Cterm and digested with BglII and MscI restriction enzymes. The plasmid pDknobΔ.SN-Cterm was obtained by cloning into the vector pDknob digested with MscI/EcoRI a PCR fragment obtained from pDknob using the primers knob-for3 (5'-CCAAGTGCATACTCTATGT-CATTTT-3'; SEQ ID NO:33) and knobC-Spe/Not.rev (5'-TCGAATTCTTTAAGCGGCCGCACCAC-TAGTTTCTTGGGCAATGTATGAAAA-3'; SEQ ID NO:34) and cut with MscI/EcoRI enzymes.

Plasmid pDknobΔ-L0 was PCR amplified using the primers knobΔ (5'-GGAGATCTTACTGAAGGCAACGCTGT-TGGATTTATG-3'; SEQ ID NO:31) and pD.rev (5'-TCT-GATTTAATCTGTATCAGGCTG-3'; SEQ ID NO:32). The resulting PCR product was digested with BglII and EcoRI restriction enzymes and cloned into the BglI and EcoRI sites of pHis.knob vector. The resulting pHis.knobΔ.SN-HI loop vector was digested with SpeI and NotI enzymes and used for cloning fragments containing the selected epitopes. The latter were obtained by PCR-amplification of lambda DNA of the L derivatives using the primers bioSN.for (5'-ACAGGAAA-CAGGAGACACAACTAGT-3'; SEQ ID NO:40) and bioSN-.rev (5'-TAGAGTATGCACTTGGAGCGGCCGC-3'; SEQ ID NO:41), digested with SpeI and NotI enzymes and purified on Streptavidin-coated magnetic micro-beads (Dynal A.S., Oslo, Norway).

Recombinant Ad5 fiber knob derivatives (knobΔ-L1, knobΔ-L6 and knobΔ-L33) containing the N-terminal six-His purification tag were expressed in *E. coli* and purified by FPLC on Hi-Trap chelating HP column (APB, Uppsala, Sweden).

Cell-ELISA—Cells were seeded at about 80,000 cells/well in 500 μl of culture medium in 24-well plates and incubated at 37° C. with 5% $CO_2$ for 48 hours. Confluent cells were then starved by incubating with medium without serum for 1 hr at 37° C., washed once with cold PBS, and then fixed by incubating with 4% para-formaldehyde for 10 min at 4°. Cells were extensively washed with cold PBS and blocked by incubating with $PBBS^{++}$ buffer (1% BSA, 10 mM $MgCl_2$, 1 mM $CaCl_2$ in PBS) for 30 min at 4° C. To monitor protein binding, cells were incubated with a 20 μg/ml dilution of purified protein in $PBBS^{++}$ overnight at 4° C. Plates were then extensively washed with $PBBS^{++}$ and captured protein was detected by an anti-His HRP-conjugated antibody (Invitrogen) diluted 1:1000 in $PBBS^{++}$ buffer. After 2 hours incubation at 4° C., plates were extensively washed and peroxidase activity was detected by incubation with TMB liquid substrate system. Developing reaction was stopped by adding 2M $H_2SO_4$. The plates were read by an automated ELISA reader (Labsystems Multiskan Bichromatic, Helsinki, Finland), and the results were expressed as $A=A_{450nm}-A_{620nm}$.

Results—The library of modified fiber knobs was screened to single out peptide ligands binding to a cell surface receptor other than CAR. Mouse embryo fibroblasts, NIH3T3 cells, which display undetectable levels of CAR on their surface and are poorly transduced by adenovirus, were chosen as the target cell. About $5\times10^9$ plaque forming units (pfu) of the λknobΔ-14aa.cys library were applied to plated NIH3T3 cells. Following incubation, unbound phage were removed; the cells were extensively washed, and bound phage were propagated by infecting bacteria About $1\times10^5$ clones were rescued and amplified. Immunoscreening this pool of phage with anti-knob antibodies showed that 20% of the clones displayed a knob on their surface which was expressed as a trimeric complex in 100% of the clones. In contrast, probing the input library with anti-knob antibodies scored positive in 26% of the clones, 75% of which also reacted with anti-trimeric knob antibodies. These findings suggest that knob expression was accompanied by a reduced growth rate. During amplification, this bias markedly favored clones that did not express the foreign protein. Thirty clones were randomly chosen among the knob-positive clones from the pool of phage derived from the panning round. Phage lysates from each of these clones were prepared and binding to NIH3T3 cells measured cell-ELISA (data not shown). This preliminary screening focused the analysis on three clones (λknobΔ-L1, λknobΔ-L6 and λknobΔ-L33) whose binding to NIH3T3 cells was monitored by flow cytometry (FIG. 17). The three modified fiber knobs isolated by this method showed a variation in the distribution median of fluorescent-labeled cells as compared to parental vector, indicating an increased binding to NIH3T3 cells. Control phage λNS3 bound NIH3T3 cells with efficiency comparable to that of λknobΔ-wt. Sequence analysis of these three modified fiber knobs revealed a high degree of similarity (FIG. 18), suggesting that they interact with the same receptor.

The same Ad5 knobΔ-L1, -L16 and -L33 derivatives were expressed in bacteria as recombinant proteins. A histidine tail was added at their N-terminus to facilitate purification and to be used as a tag for their detection. These recombinant knob proteins assembled as homotrimeric complexes and exhibited binding to NIH3T3 cells higher than knobΔ-wt protein (data not shown).

EXAMPLE 5

Adenoviral Vectors with Modified Fiber Knobs Efficiently Transduce NIH3T3 Cells

Cells—Mouse fibroblast NIH3T3 cells were obtained from the American Type Culture Collection (ATCC, Rockville, Md., U.S.A.). The cells were cultured in Dulbecco's modified Eagle's medium (DMEM). All media were supplemented with 10% (v/v) fetal calf serum (FCS).

Viruses—The recombinant adenoviruses were propagated on Per.C6 cells and purified by centrifugation in CsCl gradients. Virus particle titers were determined spectrophotometrically, wherein 1 U of optical density at 260 nm corresponds to $1.1 \times 10^{12}$ particles/ml. Because the attachment molecule(s) for the Ad5 derivatives are unknown, vectors need to be compared with equal amounts of virus particles per cell. The consistent results from several experiments using different batches of the Ad5 derivatives and the comparable infectivity measured for all viruses on CAR-positive cells exclude the possibility that the quality of virus preparations contributed to the variations observed in transduction efficiency. Restriction analysis of the viral genome and sequencing of the fiber knob region confirmed identity of virus preparations. All Ad5luc derivatives showed length of time from transfection to cytopathic effect, amplification rates, and virus yields indistinguishable from those of Ad5luc-wt virus. Viruses were named Ad5luc-LX where "x" indicates the peptide ligand incorporated within the viral genome.

Construction of recombinant Ad plasmids—First generation adenoviruses containing a luciferase-expressing cassette in place of the E1 region of the Ad5 genome, and the selected peptide ligands in the HI loop of fiber, were constructed by homologous recombination in *E. Coli* BJ5183.

The Ad5 25219-27018 nucleotide fragment encompassing the wild-type fiber gene was cloned into the Litmus28 vector (N.E.B., Beverly, Mass., U.S.A). Self-annealing the MfeI-SwaI oligonucleotide (5'-AATTCCCATTTAAATGGG-3'; SEQ ID NO:42) generated a 18 bp dsDNA fragment containing a SwaI restriction site. Thanks to its MfeI-compatible ends, this fragment was cloned into the MfeI site of LITMUS 28-fiber creating a unique SwaI site immediately downstream of the fiber gene. The resulting plasmid pLITfbr-SwaI was used to introduce the SwaI site in pAd5-H10 by bacterial homologous recombination thus generating pAd5-SwaI, which does not generate viable virus upon transfection.

Ad5luc and Ad5luc-SwaI derivatives harboring a luciferase-expression cassette that replaces the E1 region of Ad5 genome were constructed as follows. Digesting the plasmid pGGluc (Gene Therapy Systems, Inc., San Diego, Calif.) with McsI and KpnI restriction enzymes isolated the CMV-luciferase expression cassette. The resulting 3.5-kb CMV-luciferase expression cassette was made blunt by T4 polymerase and cloned into the ClaI/EcoRV sites of the shuttle vector pΔE1sp1A (Bett et al., 1994, *Proc. Natl. Acad. Sci. USA* 91:8802-8806) to generate the plasmid pΔE1CMVLuc. A 6.4 kb DNA fragment containing the luciferase expression cassette flanked by Ad5 genome sequences was excised from pΔE1CMVLuc by Ssp1/BstZ17 digestion and inserted by homologous recombination in *E. Coli* BJ5183 cells into Cla-linearized pBHG10 plasmid (Chartier et al, 1996, *J. Virol.* 79:4805-4810; Bett et al., 1994, supra). A 8.8 kb AvrII/BstZ17 DNA fragment was obtained from this last clone and inserted into the PacI site of Adenovirus H10 backbone (Sandig et al, 2000, *Proc. Natl. Acad. Sci. USA* 97:1004-1007) to generate the pAd5luc-wt and pAd5luc-SwaI. Ad5 fiber shuttle plasmid pLITfbr-L0 was constructed by cloning into pLITMUS20 vector the Ad5 fiber gene in which unique SpeI and NotI sites have been engineered in the knob HI loop region as reported in FIG. 13. Peptide ligand sequences were PCR amplified from λ DNA template, SpeI/NotI restricted, and cloned into the corresponding sites of pLITfbr-L0 to generate plasmid pLITfbr-LX. Mutated fiber sequences from pLITfbr-LX plasmids were incorporated into pAd5luc-SwaI by bacterial homologous recombination generating plasmids pAd5luc-LX.

Transduction of cells—NIH3T3 cells were seeded at about 50,000 cells/well in 500 µl of culture medium in 24 well plates and incubated for 48 hrs at 37° C. with 5% $CO_2$. Confluent cells were washed with DF buffer (2% FBS in DMEM) and infected with CsCl-purified adenovirus in DF buffer for 30 min at RT. Unbound virus were removed and cells washed with DF buffer. Cell extract and luciferase assays were performed with Luciferase Assay System (Promega, Madison, Wis., U.S.A) according to manufacturer instructions. Luciferase activity is expressed as relative light units (RLU) per mg of protein. Each point in the display items represents the mean of triplicate determinations, and the standard deviation for each value is reported.

Results—Ad5 derivatives incorporating the peptide ligands within the fiber knob were generated to investigate their tropism. Said Ad5 derivatives showed enhanced binding to NIH3T3 cells. To simplify the downstream gene transfer assay, a firefly luciferase gene under the transcriptional control of the cytomegalovirus (CMV) promoter was inserted in place of the E1 region of an Ad5 backbone (Ad5luc-wt). Adenovirus derivatives, Ad5luc-L0, -L1, -L16 and -L33, were generated in which the peptide ligands listed in FIG. 18 within the knob HI loop were engineering into the corresponding region of the viral genome by homologous recombination in bacteria. Of note, to preserve CAR binding and allow amplification of the virus, we did not transfer the TAYT (SEQ ID NO:45) deletion but incorporated these peptide ligands in the Ad5luc-wt fiber gene.

No significant differences were detected between the Ad5luc-LX derivatives and the Ad5luc-wt virus for amplification rate, virus yield, and titers measured as viral particles. The Ad5luc-LX derivatives were tested for their gene transfer efficiency of NIH3T3 cells, using Ad5luc-wt as a reference. Ad5luc-L1, Ad5luc-L16 and Ad5luc-L33 exhibited a dramatically improved transduction rate (from 100, up to 700-fold) on NIH3T3 cells, as compared to Ad5luc-wt (FIG. 19).

The Ad5luc-L0 control virus behaved in a manner indistinguishable from Ad5luc-wt, indicating that inserting the SGAAA (SEQ ID NO:39) sequence at T546 in the fiber's HI loop did not affect virus tropism.

To analyze the infectious pathway of the Ad5luc-LX derivatives, competition assays were performed by infecting NIH3T3 cells in the presence of recombinant knob proteins.

Gene transfer activity of Ad5luc-L16 in NIH3T3 cells was reduced to 30% by pre-incubation with the homologous knobΔ-L16 protein, as compared to the control knob-wt protein (FIG. 20). These data demonstrate that the modified knobs activate a CAR-independent infectious pathway, mediated by binding to an unknown cell surface receptor. In contrast, the homologous knob-wt protein had little effect on the already low levels of luciferase expression mediated by Ad5luc-wt, compared to control knobΔ-L16 protein (FIG. 20), indicating that its low transduction activity in NIH3T3 cells was not mediated by CAR.

EXAMPLE 6

Cell Entry of Modified Ad5 Fibers is Mediated by $\alpha_v$ Integrins

Cells—Mouse fibroblast NIH3T3 cells were obtained from the American Type Culture Collection (ATCC, Rockville, Md., U.S.A.). The cells were cultured in Dulbecco's modified Eagle's medium (DMEM). All media were supplemented with 10% (v/v) fetal calf serum (FCS).

Transduction of cells—NIH3T3 cells were seeded at about 50,000 cells/well in 500 µl of culture medium in 24 well plates and incubated for 48 hrs at 37° C. with 5% $CO_2$. Confluent cells were washed with DF buffer (2% FBS in DMEM) and infected with CsCl-purified adenovirus in DF buffer for 30 min at RT. Unbound virus was removed and cells washed with DF buffer. Cell extract and luciferase assays were performed with Luciferase Assay System (Promega, Madison, Wis., U.S.A) according to manufacturer instructions. Luciferase activity is expressed as relative light units (RLU) per mg of protein. Each point in the display items represents the mean of triplicate determinations, and the standard deviation for each value is reported.

In competition experiments, cells were pre-incubated with 10 µg/ml of recombinant protein, or with 4 mg/ml RGD or control RGE peptide, in DF buffer for 60 min at RT. Virus was then added (50 pp/cell) without removing the recombinant protein or the peptide and infection allowed as above. Results are expressed as the percentage of luciferase activity of cells in the presence of control protein (knobΔ-L16 for Ad5luc-wt and knob-wt for Ad5luc-L16) or RGE peptide, respectively. Synthetic peptides were obtained from Bio Synthesis (Lewisville, Tex., U.S.A.).

Results—NIH3T3 cells do not express CAR but have rather high levels of $\alpha_v\beta_3$ and $\alpha_v\beta_5$ integrins on their surface. We therefore assessed the role of integrin-penton interaction in the cell entry of Ad5 derivatives by measuring their transduction efficiency in the presence of an RGD (GRGDSP; SEQ ID NO:43) peptide compared to RGE (GRGESP; SEQ ID NO:44) control peptide. The RGD peptide blocks the interaction between the RGD motifs of the Ad5 penton base with cell $\alpha_v$ integrins, thereby inhibiting viral entry. Pre-incubation of NIH3T3 cells with RGD peptide reduced transduction of Ad5luc-L1, Ad5luc-L16 and Ad5luc-L33 by 40%, 60% and 61%, respectively, compared to control RGE peptide. Thus, following their primary interaction with an unknown cellular receptor, Ad5 derivatives are internalized through binding to $\alpha_v$ integrins. The same experiments using Ad5luc-wt showed a marked reduction of its already low transduction efficiency, indicating that the low infectivity of the virus in NIH3T3 cells mainly relied on direct interaction with $\alpha_v$ integrins.

EXAMPLE 7

Gene Transfer Efficiency of Modified Ad5 Fibers in CAR-Negative Cells and CAR-Positive Cells Cells—Chinese hamster ovary (CHO) were obtained from the American Type Culture Collection (ATCC, Rockville, Md., U.S.A.). The cells were cultured in MEMα medium. All media were supplemented with 10% (v/v) fetal calf serum (FCS).

Mouse liver NMuLi cells were obtained from the American Type Culture Collection (ATCC, Rockville, Md., U.S.A.). The cells were cultured in Dulbecco's modified Eagle's medium (DMEM). All media were supplemented with 10% (v/v) fetal calf serum (FCS).

Transduction of cells—NIH3T3 and NMuli cells were seeded at about 50,000 cells/well in 500 µl of culture medium in 24 well plates and incubated for 48 hrs at 37° C. with 5% $CO_2$. Confluent cells were washed with DF buffer (2% PBS in DMEM) and infected with CsCl-purified adenovirus in DF buffer for 30 min at RT. Unbound virus was removed and cells washed with DF buffer. For CHO cells, MEMα medium was used. Fresh complete medium was added and cells were incubated for 48 hrs for protein expression. Cell extract and luciferase assays were performed with Luciferase Assay System (Promega, Madison, Wis., U.S.A) according to manufacturer instructions. Luciferase activity is expressed as relative light units (RLU) per mg of protein. Each point in the display items represents the mean of triplicate determinations, and the standard deviation for each value is reported.

Results—We investigated whether the non-native infection route used by Ad5 mutants also supported improved transduction in cell types other than NIH3T3 and NMuLi. Chinese hamster ovary (CHO) cells were chosen because they express undetectable levels of CAR and $\alpha_v\beta_3$ integrin on their surface, and low levels of $\alpha_v\beta_5$. Not surprisingly, CHO cells were poorly transduced by Ad5luc-wt (FIG. 21). However, all three Ad5 derivatives infected these cells with efficiencies much higher than Ad5luc-wt. Ad5luc-L1 and Ad5luc-L33 proved the most efficient, with up to 270- and 320-fold increase over the control wt virus, respectively. Thus, CHO cells also display the receptor targeted by knob mutants on their surface. In the absence of CAR, and presence of low levels of $\alpha_v\beta_5$ integrin, this interaction mediates an effective transduction of CHO cells.

To explore whether the receptor targeted by the Ad5 derivatives was also expressed in CAR-positive cells, mouse liver NMuli cells, which express high CAR and $\alpha_v$ integrin levels and are efficiently transduced by Ad5, were infected (FIG. 19). All three Ad5 derivatives infected Nmuli cells with efficiency comparable, if not higher, to that of Ad5luc-wt. An excess of recombinant knob-wt protein lowered the infectivity of Ad5luc-wt virus to 5% (FIG. 20). By contrast, the same conditions did not affect transduction efficiency of the derivatives, demonstrating that a CAR-independent cell entry pathway was also effective in NMuli cells.

EXAMPLE 8

Gene Transfer Efficiency of Human and Mouse Dendritic Cells, Human Primary Melanocytes and Murine Muscle Tissue Cells—Primary murine DC were obtained from Balb/c female bone marrow as described (Lutz et al., 1999, *J. Immunol. Methods* 223:77-92). Briefly, total bone marrow leukocytes were plated in bacteriological Petri dishes in RPMI and GM-CSF (2 ng/ml). The medium was changed every 2-3 days. On day 7 of in vitro culture, cells were used.

Human DC cells were obtained as described (Engering et al., 2002, *J. Immunol.* 168:2118-2126). Briefly, human blood monocytes were isolated from buffy coats from a healthy donor by affinity purification using anti-CD14 (Milteny Biotec, Auburn, Calif., U.S.A.). Immature DCs were generated by culturing monocytes in RPMI 1640/10% FCS in the presence of IL-4 (100 ng/ml; Duotech, Rocky Hill, N.J., U.S.A.) and GM-CSF (800 U/ml; Duotech, Rocky Hill, N.J., U.S.A.). The medium was changed every 3 days, and on day 7 cells were used.

Primary human melanocytes were isolated from patients and cultured in vitro for 4 passages in the following medium: 60% DMEM with 30% di Ham's F12, 2% FCS4, 4 mM L-Glutamminenale, 50 IU/ml-50 µg/m Penicillin-Streptomicin, 24.3 µg/ml Adenina, 5 µ/ml Insulina, 0.4 µg/ml Hydrocortison, 1.36 ng/ml Triiodotironin, $10^{-10}$ M Colera toxin, 10 ng/ml EGF, 100 ng/ml BFGF, TPA.

Transduction of cells—Mouse and human DC were seeded at about 200,000 cells/well in 500 µl of culture medium in 24 well plates and incubated for 24 hrs at 37° C. with 5% $CO_2$.

Confluent cells were washed with RF buffer (2% FBS in RPMI) and infected with CsCl-purified Adenovirus in RF buffer for 40 min at RT. Unbound virus was removed, cells washed with RF buffer and incubated with complete medium for 48 hours for protein expression.

Primary human melanocytes were seeded at about 50,000 cells/well in 500 µl of culture medium in 24 wells plate and incubated for 48 hrs at 37° C. with 5% $CO_2$. Confluent cells were washed with DF buffer (2% FBS in DMEM and infected with CsCl-purified adenovirus in DF buffer for 30 min at RT. Unbound virus was removed and cells washed with DF buffer. Fresh complete medium was added and cells were incubated for 48 hrs for protein expression.

Muscle tissue—Quadriceps of 8 weeks old female BalbC mice were injected with $10^9$, $10^8$ or $10^7$ vp of adenovirus wild-type (Ad5luc-wt) or adenovirus derivatives (Ad5luc-L1 and Ad5luc-L33). Viruses were diluted in 50 µl of physiological solution. Twelve muscles were injected with each adenovirus derivative and wild-type virus (four muscles for each moi used). Forty-eight hours after the infection, mice were sacrificed, muscles removed and washed with PBS, and homogenized in 300 µl of lysis buffer (Luciferase Assay System, Promega). After one cycle of freeze and thaw, extracts were centrifuged at 14000 rpm for 20 minutes at 4° C. Supernatant was recovered and 30 µl were used for the luciferase assay (Luciferase Assay System, Promega). Protein quantification was performed by the BCA Protein Assay kit (Pierce). Luciferase activity is expressed as relative light units (RLU) per mg of protein.

Results—The results obtained thus far suggested that CAR-independent tropism of the Ad5 derivatives was not restricted to a given cell type or a defined species. To assess whether the selected modified fibers are better suited to infect cells/tissue of therapeutic interest, dendritic cells (DC), human melanocytes and skeletal muscle tissue were chosen.

Mouse immature DC were obtained from bone marrow and amplified in vitro. FACS analysis confirmed this population as $CD11c^+$, $CD11b^+$, MHC- and MHC-II positive. Bone marrow derived mouse immature DC were infected at various moi with Ad5luc-L1 and Ad5luc-L33. Both virus transduced mouse immature DC with increased efficiency as compared to Ad5luc-wt (FIG. 22A). In particular Ad5luc-L33 infected mouse DC from 24 to 100-fold better than parental vector, depending on the moi used. A similar experiment was performed on human immature DC purified by CD14-affinity chromatography from peripheral blood of a healthy donor and differentiated in vitro. FACS analysis confirmed this population as $CD1a^+$, $HLA-DR^+$, $CD80^+$, $CD83^+$, $CD86^+$ and $CD14^{neg}$. As reported in literature, Ad5luc-wt poorly transduced immature human DC at the moi tested (FIG. 22B). In contrast, the Ad5Luc-L1 and Ad5luc-L33 proved far superior in terms of efficiency of transduction. Namely, Ad5luc-L33 uptake by human DC is increased up to 100-fold as compared to wt virus.

Human primary melanocytes were infected at various moi with Ad5luc-LX derivatives. Compared to Ad5luc-wt, the three Ad5luc derivatives displayed enhanced transduction efficiency ranging, in the case of Ad5luc-L33 from 50- to 900-fold the efficiency of Ad5luc-wt.

Quadriceps of BalbC mice 8 weeks old were injected with $10^9$, $10^8$, $10^7$ vp of adenovirus wt or adenovirus derivatives (L1, L33). At all three m.o.i. tested, adenovirus derivatives Ad5luc-L1 and Ad5luc-L33 showed an increased efficiency of muscle transduction compared to Ad5luc-wt FIG. 23). Namely, when $10^8$ vp were injected, Ad5luc-L33 and Ad5luc-L1 transduced mouse muscle 8-fold (p<10exp-5) and 5-fold (p<0.001) better than Ad5luc-wt, respectively.

SEQUENCE LISTING

```
<160> NUMBER OF SEQ ID NOS: 47

<210> SEQ ID NO 1
<211> LENGTH: 597
<212> TYPE: PRT
<213> ORGANISM: Artificial Sequence
<220> FEATURE:
<223> OTHER INFORMATION: chimeric protein

<400> SEQUENCE: 1

Met Lys Arg Ala Arg Pro Ser Glu Asp Thr Phe Asn Pro Val Tyr Pro
 1               5                  10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45
```

```
Leu Arg Leu Ser Glu Pro Leu Val Thr Ser Asn Gly Met Leu Ala Leu
    50                  55                  60

Lys Met Gly Asn Gly Leu Ser Leu Asp Glu Ala Gly Asn Leu Thr Ser
 65                  70                  75                  80

Gln Asn Val Thr Thr Val Ser Pro Pro Leu Lys Thr Lys Ser Asn
                 85                  90                  95

Ile Asn Leu Glu Ile Ser Ala Pro Leu Thr Val Thr Ser Glu Ala Leu
                100                 105                 110

Thr Val Ala Ala Ala Ala Pro Leu Met Val Ala Gly Asn Thr Leu Thr
            115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Lys Leu Ala Leu Gln
145                 150                 155                 160

Thr Ser Gly Pro Leu Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
            195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Leu Ile Leu Asp Val
            260                 265                 270

Ser Tyr Pro Phe Asp Ala Gln Asn Gln Leu Asn Leu Arg Leu Gly Gln
    275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
    355                 360                 365

Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
            420                 425                 430

Leu Ala Thr Val Ser Val Leu Ala Val Lys Gly Ser Leu Ala Pro Ile
            435                 440                 445

Ser Gly Thr Val Gln Ser Ala His Leu Ile Ile Arg Phe Asp Glu Asn
450                 455                 460
```

```
Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                485                 490                 495

Phe Met Pro Asn Leu Ser Ala Tyr Pro Lys Ser His Gly Lys Thr Ala
            500                 505                 510

Lys Ser Asn Ile Val Ser Gln Val Tyr Leu Asn Gly Asp Lys Thr Lys
        515                 520                 525

Pro Val Thr Leu Thr Ile Thr Leu Asn Gly Thr Gln Glu Thr Gly Asp
    530                 535                 540

Thr Thr Ser Phe Cys Val Ala Ser Arg Gly Gly Ser Ser Cys Tyr Ala
545                 550                 555                 560

Ala Ala Pro Ser Ala Tyr Ser Met Ser Phe Ser Trp Asp Trp Ser Gly
                565                 570                 575

His Asn Tyr Ile Asn Glu Ile Phe Ala Thr Ser Ser Tyr Thr Phe Ser
            580                 585                 590

Tyr Ile Ala Gln Glu
        595

<210> SEQ ID NO 2
<211> LENGTH: 598
<212> TYPE: PRT
<213> ORGANISM: Artificial Sequence
<220> FEATURE:
<223> OTHER INFORMATION: chimeric protein

<400> SEQUENCE: 2

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Leu Gln
145                 150                 155                 160

Thr Ser Gly Pro Leu Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
210                 215                 220
```

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
            245                 250                 255

Gly Gly Leu Arg Ile Asp Ser Gln Asn Arg Arg Leu Ile Leu Asp Val
                260                 265                 270

Ser Tyr Pro Phe Asp Ala Gln Asn Gln Leu Asn Leu Arg Leu Gly Gln
            275                 280                 285

Gly Pro Leu Phe Ile Asn Ser Ala His Asn Leu Asp Ile Asn Tyr Asn
        290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365

Ser Asn Lys Ala Met Val Pro Lys Leu Gly Thr Gly Leu Ser Phe Asp
370                 375                 380

Ser Thr Gly Ala Ile Thr Val Gly Asn Lys Asn Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
            420                 425                 430

Leu Ala Thr Val Ser Val Leu Ala Val Lys Gly Ser Leu Ala Pro Ile
        435                 440                 445

Ser Gly Thr Val Gln Ser Ala His Leu Ile Ile Arg Phe Asp Glu Asn
450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                485                 490                 495

Phe Met Pro Asn Leu Ser Ala Tyr Pro Lys Ser His Gly Lys Thr Ala
            500                 505                 510

Lys Ser Asn Ile Val Ser Gln Val Tyr Leu Asn Gly Asp Lys Thr Lys
        515                 520                 525

Pro Val Thr Leu Thr Ile Thr Leu Asn Gly Thr Gln Glu Thr Gly Asp
530                 535                 540

Thr Thr Ser Phe Cys Lys Val Val Gly Gly Gly Ser Ser Cys Ser Pro
545                 550                 555                 560

Ala Ala Ala Pro Ser Ala Tyr Ser Met Ser Phe Ser Trp Asp Trp Ser
                565                 570                 575

Gly His Asn Tyr Ile Asn Glu Ile Phe Ala Thr Ser Ser Tyr Thr Phe
            580                 585                 590

Ser Tyr Ile Ala Gln Glu
        595

<210> SEQ ID NO 3
<211> LENGTH: 598
<212> TYPE: PRT
<213> ORGANISM: Artificial Sequence
<220> FEATURE:
<223> OTHER INFORMATION: chimeric protein

```
<400> SEQUENCE: 3

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
        50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Leu Gln
145                 150                 155                 160

Thr Ser Gly Pro Leu Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
        210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
        290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365

Ser Asn Lys Ala Met Val Pro Lys Leu Gly Thr Gly Leu Ser Phe Asp
        370                 375                 380

Ser Thr Gly Ala Ile Thr Val Gly Asn Lys Asn Asn Asp Lys Leu Thr
385                 390                 395                 400

Leu Trp Thr Thr Pro Ala Pro Ser Pro Asn Cys Arg Leu Asn Ala Glu
```

|     |     |     |     | 405 |     |     |     |     | 410 |     |     |     |     | 415 |
| --- | --- | --- | --- | --- | --- | --- | --- | --- | --- | --- | --- | --- | --- | --- |
| Lys | Asp | Ala | Lys | Leu | Thr | Leu | Val | Leu | Thr | Lys | Cys | Gly | Ser | Gln | Ile |
|     |     |     | 420 |     |     |     |     | 425 |     |     |     |     | 430 |     |     |

Leu Ala Thr Val Ser Val Leu Ala Val Lys Gly Ser Leu Ala Pro Ile
        435                 440                 445

Ser Gly Thr Val Gln Ser Ala His Leu Ile Ile Arg Phe Asp Glu Asn
        450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                485                 490                 495

Phe Met Pro Asn Leu Ser Ala Tyr Pro Lys Ser His Gly Lys Thr Ala
                500                 505                 510

Lys Ser Asn Ile Val Ser Gln Val Tyr Leu Asn Gly Asp Lys Thr Lys
            515                 520                 525

Pro Val Thr Leu Thr Ile Thr Leu Asn Gly Thr Gln Glu Thr Gly Asp
        530                 535                 540

Thr Thr Ser Phe Phe Cys Val Ser Asp Gly Gly Ser Ser Cys Pro
545                 550                 555                 560

Ala Ala Ala Pro Ser Ala Tyr Ser Met Ser Phe Ser Trp Asp Trp Ser
                565                 570                 575

Gly His Asn Tyr Ile Asn Glu Ile Phe Ala Thr Ser Ser Tyr Thr Phe
                580                 585                 590

Ser Tyr Ile Ala Gln Glu
        595

<210> SEQ ID NO 4
<211> LENGTH: 1794
<212> TYPE: DNA
<213> ORGANISM: Artificial Sequence
<220> FEATURE:
<223> OTHER INFORMATION: chimeric DNA

<400> SEQUENCE: 4

```
atgaagcgcg caagaccgtc tgaagatacc ttcaaccccg tgtatccata tgacacggaa      60
accggtcctc caactgtgcc ttttcttact cctcccttg tatcccccaa tgggtttcaa     120
gagagtcccc tggggtact  ctctttgcgc ctatccgaac tctagttac  ctccaatggc     180
atgcttgcgc tcaaaatggg caacggcctc tctctggacg aggccggcaa ccttacctcc     240
caaaatgtaa ccactgtgag cccacctctc aaaaaaacca agtcaaacat aaacctggaa     300
atatctgcac ccctcacagt tacctcagaa gccctaactg tggctgccgc cgcacctcta     360
atggtcgcgg caacacact  caccatgcaa tcacaggccc cgctaaccgt gcacgactcc     420
aaacttagca ttgccaccca aggacccctc acagtgtcag aaggaaagct agccctgcaa     480
acatcaggcc cctcaccac  caccgatagc agtaccctta ctatcactgc ctcacccct      540
ctaactactg ccactggtag cttgggcatt gacttgaaag agcccattta tacacaaaat     600
ggaaaactag gactaaagta cggggctcct ttgcatgtaa cagacgacct aaacactttg     660
accgtagcaa ctggtccagg tgtgactatt aataatactt ccttgcaaac taaagttact     720
ggagccttgg gttttgattc acaaggcaat atgcaactta atgtagcagg aggactaagg     780
attgattctc aaaacagacg ccttatactt gatgttagtt atccgtttga tgctcaaaac     840
caactaaatc taagactagg acagggcct  cttttatata actcagccca caacttggat     900
attaactaca caaaggcct  ttacttgttt acagcttcaa caattccaa  aaagcttgag     960
```

```
gttaacctaa gcactgccaa ggggttgatg tttgacgcta cagccatagc cattaatgca    1020
ggagatgggc ttgaatttgg ttcacctaat gcaccaaaca caaatcccct caaaacaaaa    1080
attggccatg gcctagaatt tgattcaaac aaggctatgg ttcctaaact aggaactggc    1140
cttagttttg acagcacagg tgccattaca gtaggaaaca aaaataatga taagctaact    1200
ttgtggacca caccagctcc atctcctaac tgtagactaa atgcagagaa agatgctaaa    1260
ctcactttgg tcttaacaaa atgtggcagt caaatacttg ctacagtttc agttttggct    1320
gttaaaggca gtttggctcc aatatctgga acagttcaaa gtgctcatct tattataaga    1380
tttgacgaaa atggagtgct actaaacaat tccttcctgg acccagaata ttggaacttt    1440
agaaatggag atcttactga aggcacagcc tatacaaacg ctgttggatt tatgcctaac    1500
ctatcagctt atccaaaatc tcacggtaaa actgccaaaa gtaacattgt cagtcaagtt    1560
tacttaaacg gagacaaaac taaacctgta acactaacca ttacactaaa cggtacacag    1620
gaaacaggag acacaactag tttctgcgtt gcgtcccgcg gtgggtcctc ctgctacgcg    1680
gccgctcctt ccgcatactc tatgtcattt tcatgggact ggtctggcca caactacatt    1740
aatgaaatat ttgccacatc ctcttacact ttttcataca ttgcccaaga ataa          1794
```

<210> SEQ ID NO 5
<211> LENGTH: 1797
<212> TYPE: DNA
<213> ORGANISM: Artificial Sequence
<220> FEATURE:
<223> OTHER INFORMATION: chimeric DNA

<400> SEQUENCE: 5

```
atgaagcgcg caagaccgtc tgaagatacc ttcaacccccg tgtatccata tgacacggaa      60
accggtcctc caactgtgcc ttttcttact cctcccttttg tatccccccaa tgggtttcaa    120 gagagtcccc ctggggtact ctctttgcgc ctatccgaac tctagttac ctccaatggc      180 atgcttgcgc tcaaaatggg caacggcctc tctctggacg aggccggcaa ccttacctcc      240
caaaatgtaa ccactgtgag cccacctctc aaaaaaacca gtcaaacat aaacctggaa      300 atatctgcac ccctcacagt tacctcagaa gccctaactg tggctgccgc cgcacctcta      360
atggtcgcgg gcaacacact caccatgcaa tcacaggccc cgctaaccgt gcacgactcc      420
aaacttagca ttgccacccca aggaccccctc acagtgtcag aaggaaagct agccctgcaa    480
acatcaggcc cctcaccac caccgatagc agtacccctta ctatcactgc ctcacccctt    540
ctaactactg ccactggtag cttgggcatt gacttgaaag agcccattta tacacaaaat    600
ggaaaactag gactaaagta cggggctcct ttgcatgtaa cagacgacct aaacactttg    660
accgtagcaa ctggtccagg tgtgactatt ataatactt ccttgcaaac taaagttact    720
ggagccttgg gttttgattc acaaggcaat atgcaactta atgtagcagg aggactaagg    780
attgattctc aaaacagacg cctatactt gatgttagtt atccgtttga tgctcaaaac    840
caactaaatc taagactagg acagggcccct ttttttataa actcagccca caacttggat    900
attaactaca caaaggcct tacttgtttt acagcttcaa acaattccaa aaagcttgag    960
gttaacctaa gcactgccaa ggggttgatg tttgacgcta cagccatagc cattaatgca    1020
ggagatgggc ttgaatttgg ttcacctaat gcaccaaaca caaatcccct caaaacaaaa    1080
attggccatg gcctagaatt tgattcaaac aaggctatgg ttcctaaact aggaactggc    1140
cttagttttg acagcacagg tgccattaca gtaggaaaca aaaataatga taagctaact    1200
```

-continued

```
ttgtggacca caccagctcc atctcctaac tgtagactaa atgcagagaa agatgctaaa    1260
ctcactttgg tcttaacaaa atgtggcagt caaatacttg ctacagtttc agttttggct    1320
gttaaaggca gtttggctcc aatatctgga acagttcaaa gtgctcatct tattataaga    1380
tttgacgaaa atggagtgct actaaacaat tccttcctgg acccagaata ttggaacttt    1440
agaaatggag atcttactga aggcacagcc tatacaaacg ctgttggatt tatgcctaac    1500
ctatcagctt atccaaaatc tcacggtaaa actgccaaaa gtaacattgt cagtcaagtt    1560
tacttaaacg gagacaaaac taaacctgta acactaacca ttacactaaa cggtacacag    1620
gaaacaggag acacaactag tttctgcaag gtcgtgggtg gtggttcctc ctgctccccg    1680
gcggccgctc cttccgcata ctctatgtca ttttcatggg actggtctgg ccacaactac    1740
attaatgaaa tatttgccac atcctcttac actttttcat acattgccca agaataa       1797
```

<210> SEQ ID NO 6
<211> LENGTH: 1797
<212> TYPE: DNA
<213> ORGANISM: Artificial Sequence
<220> FEATURE:
<223> OTHER INFORMATION: chimeric DNA

<400> SEQUENCE: 6

```
atgaagcgcg caagaccgtc tgaagatacc ttcaaccccg tgtatccata tgacacggaa      60
accggtcctc caactgtgcc ttttcttact cctcccttg tatcccccaa tgggtttcaa      120
gagagtcccc ctggggtact ctctttgcgc ctatccgaac ctctagttac ctccaatggc      180
atgcttgcgc tcaaaatggg caacggcctc tctctggacg aggccggcaa ccttacctcc      240
caaaatgtaa ccactgtgag cccacctctc aaaaaaacca agtcaaacat aaacctggaa      300
atatctgcac ccctcacagt tacctcagaa gccctaactg tggctgccgc cgcacctcta      360
atggtcgcgg gcaacacact caccatgcaa tcacaggccc cgctaaccgt gcacgactcc      420
aaacttagca ttgccaccca aggacccctc acagtgtcag aaggaaagct agccctgcaa      480
acatcaggcc cctcaccac caccgatagc agtaccctta ctatcactgc ctcaccccct       540
ctaactactg ccactggtag cttgggcatt gacttgaaag agcccattta tacacaaaat      600
ggaaaactag gactaaagta cggggctcct ttgcatgtaa cagacgacct aaacactttg      660
accgtagcaa ctggtccagg tgtgactatt aataatactt ccttgcaaac taaagttact      720
ggagccttgg gttttgattc acaaggcaat atgcaactta atgtagcagg aggactaagg      780
attgattctc aaaacagacg ccttatactt gatgttagtt atccgtttga tgctcaaaac      840
caactaaatc taagactagg acagggccct ctttttataa actcagccca caacttggat      900
attaactaca caaaggcct ttacttgttt acagcttcaa acaattccaa aaagcttgag      960
gttaacctaa gcactgccaa ggggttgatg tttgacgcta cagccatagc cattaatgca     1020
ggagatgggc ttgaatttgg ttcacctaat gcaccaaaca caaatcccct caaaacaaaa     1080
attggccatg gcctagaatt tgattcaaac aaggctatgg ttcctaaact aggaactggc     1140
cttagttttg acagcacagg tgccattaca gtaggaaaca aaaataatga taagctaact     1200
ttgtggacca caccagctcc atctcctaac tgtagactaa atgcagagaa agatgctaaa     1260
ctcactttgg tcttaacaaa atgtggcagt caaatacttg ctacagtttc agttttggct     1320
gttaaaggca gtttggctcc aatatctgga acagttcaaa gtgctcatct tattataaga     1380
tttgacgaaa atggagtgct actaaacaat tccttcctgg acccagaata ttggaacttt     1440
agaaatggag atcttactga aggcacagcc tatacaaacg ctgttggatt tatgcctaac     1500
```

```
ctatcagctt atccaaaatc tcacggtaaa actgccaaaa gtaacattgt cagtcaagtt   1560
tacttaaacg gagacaaaac taaacctgta acactaacca ttacactaaa cggtacacag   1620
gaaacaggag acacaactag tttcttctgc gtttccgacg gtggtggttc ctcctgcccg   1680
gcggccgctc cttccgcata ctctatgtca ttttcatggg actggtctgg ccacaactac   1740
attaatgaaa tatttgccac atcctcttac actttttcat acattgccca agaataa     1797
```

```
<210> SEQ ID NO 7
<211> LENGTH: 593
<212> TYPE: PRT
<213> ORGANISM: Artificial Sequence
<220> FEATURE:
<223> OTHER INFORMATION: chimeric protein

<400> SEQUENCE: 7

Met Lys Arg Ala Arg Pro Ser Glu Asp Thr Phe Asn Pro Val Tyr Pro
 1               5                  10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
        50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
```

```
            305                 310                 315                 320
Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365

Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
            420                 425                 430

Leu Ala Thr Val Ser Val Leu Ala Val Lys Gly Ser Leu Ala Pro Ile
        435                 440                 445

Ser Gly Thr Val Gln Ser Ala His Leu Ile Ile Arg Phe Asp Glu Asn
    450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Asn Ala Val Gly Phe Met Pro Asn
                485                 490                 495

Leu Ser Ala Tyr Pro Lys Ser His Gly Lys Thr Ala Lys Ser Asn Ile
            500                 505                 510

Val Ser Gln Val Tyr Leu Asn Gly Asp Lys Thr Lys Pro Val Thr Leu
        515                 520                 525

Thr Ile Thr Leu Asn Gly Thr Gln Glu Thr Gly Asp Thr Thr Ser Phe
    530                 535                 540

Cys Val Ala Ser Arg Gly Gly Ser Ser Cys Tyr Ala Ala Ala Pro Ser
545                 550                 555                 560

Ala Tyr Ser Met Ser Phe Ser Trp Asp Trp Ser Gly His Asn Tyr Ile
                565                 570                 575

Asn Glu Ile Phe Ala Thr Ser Ser Tyr Thr Phe Ser Tyr Ile Ala Gln
            580                 585                 590

Glu

<210> SEQ ID NO 8
<211> LENGTH: 594
<212> TYPE: PRT
<213> ORGANISM: Artificial Sequence
<220> FEATURE:
<223> OTHER INFORMATION: chimeric protein

<400> SEQUENCE: 8

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
    50                  55                  60

Lys Met Gly Asn Gly Leu Ser Leu Asp Glu Ala Gly Asn Leu Thr Ser
65                  70                  75                  80
```

-continued

```
Gln Asn Val Thr Thr Val Ser Pro Pro Leu Lys Lys Thr Lys Ser Asn
                 85                  90                  95

Ile Asn Leu Glu Ile Ser Ala Pro Leu Thr Val Thr Ser Glu Ala Leu
            100                 105                 110

Thr Val Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Leu Gln
145                 150                 155                 160

Thr Ser Gly Pro Leu Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
            245                 250                 255

Gly Gly Leu Arg Ile Asp Ser Gln Asn Arg Arg Leu Ile Leu Asp Val
        260                 265                 270

Ser Tyr Pro Phe Asp Ala Gln Asn Gln Leu Asn Leu Arg Leu Gly Gln
    275                 280                 285

Gly Pro Leu Phe Ile Asn Ser Ala His Asn Leu Asp Ile Asn Tyr Asn
        290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
            325                 330                 335

Ala Ile Asn Ala Gly Asp Gly Leu Glu Phe Gly Ser Pro Asn Ala Pro
        340                 345                 350

Asn Thr Asn Pro Leu Lys Thr Lys Ile Gly His Gly Leu Glu Phe Asp
    355                 360                 365

Ser Asn Lys Ala Met Val Pro Lys Leu Gly Thr Gly Leu Ser Phe Asp
370                 375                 380

Ser Thr Gly Ala Ile Thr Val Gly Asn Lys Asn Asn Asp Lys Leu Thr
385                 390                 395                 400

Leu Trp Thr Thr Pro Ala Pro Ser Pro Asn Cys Arg Leu Asn Ala Glu
            405                 410                 415

Lys Asp Ala Lys Leu Thr Leu Val Leu Thr Lys Cys Gly Ser Gln Ile
        420                 425                 430

Leu Ala Thr Val Ser Val Leu Ala Val Lys Gly Ser Leu Ala Pro Ile
    435                 440                 445

Ser Gly Thr Val Gln Ser Ala His Leu Ile Ile Arg Phe Asp Glu Asn
    450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Asn Ala Val Gly Phe Met Pro Asn
            485                 490                 495
```

-continued

Leu Ser Ala Tyr Pro Lys Ser His Gly Lys Thr Ala Lys Ser Asn Ile
                500                 505                 510

Val Ser Gln Val Tyr Leu Asn Gly Asp Lys Thr Lys Pro Val Thr Leu
                515                 520                 525

Thr Ile Thr Leu Asn Gly Thr Gln Glu Thr Gly Asp Thr Thr Ser Phe
            530                 535                 540

Cys Lys Val Val Gly Gly Ser Ser Cys Ser Pro Ala Ala Ala Pro
545                 550                 555                 560

Ser Ala Tyr Ser Met Ser Phe Ser Trp Asp Trp Ser Gly His Asn Tyr
                565                 570                 575

Ile Asn Glu Ile Phe Ala Thr Ser Ser Tyr Thr Phe Ser Tyr Ile Ala
                580                 585                 590

Gln Glu

<210> SEQ ID NO 9
<211> LENGTH: 594
<212> TYPE: PRT
<213> ORGANISM: Artificial Sequence
<220> FEATURE:
<223> OTHER INFORMATION: chimeric protein

<400> SEQUENCE: 9

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
    50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
                100                 105                 110

Thr Val Ala Ala Ala Pro Leu Met Val Ala Gly Asn Thr Leu Thr
            115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
                180                 185                 190

Lys Glu Pro Ile Tyr Thr Gln Asn Gly Lys Leu Gly Leu Lys Tyr Gly
            195                 200                 205

Ala Pro Leu His Val Thr Asp Asp Leu Asn Thr Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val

```
              260                 265                 270
Ser Tyr Pro Phe Asp Ala Gln Asn Gln Leu Asn Leu Arg Leu Gly Gln
            275                 280                 285

Gly Pro Leu Phe Ile Asn Ser Ala His Asn Leu Asp Ile Asn Tyr Asn
            290                 295                 300

Lys Gly Leu Tyr Leu Phe Thr Ala Ser Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
            355                 360                 365

Ser Asn Lys Ala Met Val Pro Lys Leu Gly Thr Gly Leu Ser Phe Asp
            370                 375                 380

Ser Thr Gly Ala Ile Thr Val Gly Asn Lys Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
            420                 425                 430

Leu Ala Thr Val Ser Val Leu Ala Val Lys Gly Ser Leu Ala Pro Ile
            435                 440                 445

Ser Gly Thr Val Gln Ser Ala His Leu Ile Ile Arg Phe Asp Glu Asn
            450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Asn Ala Val Gly Phe Met Pro Asn
                485                 490                 495

Leu Ser Ala Tyr Pro Lys Ser His Gly Lys Thr Ala Lys Ser Asn Ile
            500                 505                 510

Val Ser Gln Val Tyr Leu Asn Gly Asp Lys Thr Lys Pro Val Thr Leu
            515                 520                 525

Thr Ile Thr Leu Asn Gly Thr Gln Glu Thr Gly Asp Thr Thr Ser Phe
            530                 535                 540

Phe Cys Val Ser Asp Gly Gly Ser Ser Cys Pro Ala Ala Pro
545                 550                 555                 560

Ser Ala Tyr Ser Met Ser Phe Ser Trp Asp Trp Ser Gly His Asn Tyr
                565                 570                 575

Ile Asn Glu Ile Phe Ala Thr Ser Ser Tyr Thr Phe Ser Tyr Ile Ala
            580                 585                 590

Gln Glu

<210> SEQ ID NO 10
<211> LENGTH: 1782
<212> TYPE: DNA
<213> ORGANISM: Artificial Sequence
<220> FEATURE:
<223> OTHER INFORMATION: chimeric DNA

<400> SEQUENCE: 10
atgaagcgcg caagaccgtc tgaagatacc ttcaaccccg tgtatccata tgacacggaa      60
accggtcctc caactgtgcc ttttcttact cctccctttg tatcccccaa tgggtttcaa     120
gagagtcccc ctggggtact ctctttgcgc ctatccgaac ctctagttac ctccaatggc     180
```

| | |
|---|---|
| atgcttgcgc tcaaaatggg caacggcctc tctctggacg aggccggcaa ccttacctcc | 240 |
| caaaatgtaa ccactgtgag cccacctctc aaaaaaacca agtcaaacat aaacctggaa | 300 |
| atatctgcac ccctcacagt tacctcagaa gccctaactg tggctgccgc cgcacctcta | 360 |
| atggtcgcgg gcaacacact caccatgcaa tcacaggccc cgctaaccgt gcacgactcc | 420 |
| aaacttagca ttgccaccca aggacccctc acagtgtcag aaggaaagct agccctgcaa | 480 |
| acatcaggcc ccctcaccac caccgatagc agtaccctta ctatcactgc ctcaccccct | 540 |
| ctaactactg ccactggtag cttgggcatt gacttgaaag agcccattta tacacaaaat | 600 |
| ggaaaactag gactaaagta cggggctcct ttgcatgtaa cagacgacct aaacactttg | 660 |
| accgtagcaa ctggtccagg tgtgactatt aataatactt ccttgcaaac taaagttact | 720 |
| ggagccttgg gttttgattc acaaggcaat atgcaactta atgtagcagg aggactaagg | 780 |
| attgattctc aaaacagacg ccttatactt gatgttagtt atccgtttga tgctcaaaac | 840 |
| caactaaatc taagactagg acagggccct cttttataa actcagccca caacttggat | 900 |
| attaactaca acaaaggcct ttacttgttt acagcttcaa acaattccaa aaagcttgag | 960 |
| gttaacctaa gcactgccaa ggggttgatg tttgacgcta cagccatagc cattaatgca | 1020 |
| ggagatgggc ttgaatttgg ttcacctaat gcaccaaaca caaatcccct caaaacaaaa | 1080 |
| attggccatg gcctagaatt tgattcaaac aaggctatgg ttcctaaact aggaactggc | 1140 |
| cttagttttg acagcacagg tgccattaca gtaggaaaca aaaataatga taagctaact | 1200 |
| tgtgtggacca caccagctcc atctcctaac tgtagactaa atgcagagaa agatgctaaa | 1260 |
| ctcactttgg tcttaacaaa atgtggcagt caaatacttg ctacagtttc agttttggct | 1320 |
| gttaaaggca gtttggctcc aatatctgga acagttcaaa gtgctcatct tattataaga | 1380 |
| tttgacgaaa atggagtgct actaaacaat tccttcctgg acccagaata ttggaacttt | 1440 |
| agaaatggag atcttactga aggcaacgct gttggattta tgcctaacct atcagcttat | 1500 |
| ccaaaatctc acggtaaaac tgccaaaagt aacattgtca gtcaagttta cttaaacgga | 1560 |
| gacaaaacta aacctgtaac actaaccatt acactaaacg gtacacagga aacaggagac | 1620 |
| acaactagtt tctgcgttgc gtcccgcggt gggtcctcct gctacgcggc cgctccttcc | 1680 |
| gcatactcta tgtcattttc atgggactgg tctggccaca actacattaa tgaaatattt | 1740 |
| gccacatcct cttacacttt ttcatacatt gcccaagaat aa | 1782 |

<210> SEQ ID NO 11
<211> LENGTH: 1785
<212> TYPE: DNA
<213> ORGANISM: Artificial Sequence
<220> FEATURE:
<223> OTHER INFORMATION: chimeric DNA

<400> SEQUENCE: 11

| | |
|---|---|
| atgaagcgcg caagaccgtc tgaagatacc ttcaaccccg tgtatccata tgacacggaa | 60 |
| accggtcctc caactgtgcc ttttcttact cctcccttg tatcccccaa tgggtttcaa | 120 |
| gagagtcccc ctggggtact ctctttgcgc ctatccgaac tctagttac ctccaatggc | 180 |
| atgcttgcgc tcaaaatggg caacggcctc tctctggacg aggccggcaa ccttacctcc | 240 |
| caaaatgtaa ccactgtgag cccacctctc aaaaaaacca agtcaaacat aaacctggaa | 300 |
| atatctgcac ccctcacagt tacctcagaa gccctaactg tggctgccgc cgcacctcta | 360 |
| atggtcgcgg gcaacacact caccatgcaa tcacaggccc cgctaaccgt gcacgactcc | 420 |

```
aaacttagca ttgccaccca aggacccctc acagtgtcag aaggaaagct agccctgcaa     480
acatcaggcc ccctcaccac caccgatagc agtacccttc ctatcactgc ctcacccct     540 ctaactactg ccactggtag cttgggcatt gacttgaaag agcccattta tacacaaaat     600
ggaaaactag gactaaagta cggggctcct ttgcatgtaa cagacgacct aaacactttg     660
accgtagcaa ctggtccagg tgtgactatt aataatactt ccttgcaaac taaagttact     720
ggagccttgg gttttgattc acaaggcaat atgcaactta atgtagcagg aggactaagg     780
attgattctc aaaacagacg ccttatactt gatgttagtt atccgtttga tgctcaaaac     840
caactaaatc taagactagg acagggcct cttttttataa actcagccca caacttggat     900
attaactaca acaaaggcct ttacttgttt acagcttcaa acaattccaa aaagcttgag     960
gttaacctaa gcactgccaa gggggttgatg tttgacgcta cagccatagc cattaatgca    1020
ggagatgggc ttgaatttgg ttcacctaat gcaccaaaca caaatcccct caaaacaaaa    1080
attggccatg cctagaatt tgattcaaac aaggctatgg ttcctaaact aggaactggc    1140
cttagttttg acagcacagg tgccattaca gtaggaaaca aaaataatga taagctaact    1200
ttgtggacca caccagctcc atctcctaac tgtagactaa atgcagagaa agatgctaaa    1260
ctcactttgg tcttaacaaa atgtggcagt caaatacttg ctacagtttc agttttggct    1320
gttaaaggca gtttggctcc aatatctgga acagttcaaa gtgctcatct tattataaga    1380
tttgacgaaa atggagtgct actaaacaat tccttcctgg acccagaata ttggaacttt    1440
agaaatggag atcttactga aggcaacgct gttggattta tgcctaacct atcagcttat    1500
ccaaaatctc acggtaaaac tgccaaaagt aacattgtca gtcaagttta cttaaacgga    1560
gacaaaacta aacctgtaac actaaccatt acactaaacg gtacacagga aacaggagac    1620
acaactagtt tctgcaaggt cgtgggtggt ggttcctcct gctcccggc ggccgctcct    1680 tccgcatact ctatgtcatt ttcatgggac tggtctggcc acaactacat taatgaaata    1740
tttgccacat cctcttacac ttttttcatac attgcccaag aataa                    1785

<210> SEQ ID NO 12
<211> LENGTH: 1785
<212> TYPE: DNA
<213> ORGANISM: Artificial Sequence
<220> FEATURE:
<223> OTHER INFORMATION: chimeric DNA

<400> SEQUENCE: 12
atgaagcgcg caagaccgtc tgaagatacc ttcaaccccg tgtatccata tgacacggaa     60
accggtcctc caactgtgcc ttttcttact cctcccttg tatcccccaa tgggtttcaa    120
gagagtcccc ctggggtact ctctttgcgc ctatccgaac ctctagttac ctccaatggc    180
atgcttgcgc tcaaaatggg caacggcctc tctctggacg aggccggcaa ccttacctcc    240
caaaatgtaa ccactgtgag cccacctctc aaaaaaacca agtcaaacat aaacctggaa    300
atatctgcac ccctcacagt tacctcagaa gccctaactg tggctgccgc cgcacctcta    360
atggtcgcgg gcaacacact caccatgcaa tcacaggccc cgctaaccgt gcacgactcc    420
aaacttagca ttgccaccca aggacccctc acagtgtcag aaggaaagct agccctgcaa    480
acatcaggcc ccctcaccac caccgatagc agtacccttc ctatcactgc ctcacccct    540 ctaactactg ccactggtag cttgggcatt gacttgaaag agcccattta tacacaaaat    600
ggaaaactag gactaaagta cggggctcct ttgcatgtaa cagacgacct aaacactttg    660
accgtagcaa ctggtccagg tgtgactatt aataatactt ccttgcaaac taaagttact    720
```

```
ggagccttgg gttttgattc acaaggcaat atgcaactta atgtagcagg aggactaagg      780
attgattctc aaaacagacg ccttatactt gatgttagtt atccgtttga tgctcaaaac      840
caactaaatc taagactagg acagggccct cttttttataa actcagccca caacttggat    900
attaactaca acaaaggcct ttacttgttt acagcttcaa acaattccaa aaagcttgag      960
gttaacctaa gcactgccaa ggggttgatg tttgacgcta cagccatagc cattaatgca      1020
ggagatgggc ttgaatttgg ttcacctaat gcaccaaaca caaatcccct caaaacaaaa     1080
attggccatg ccctagaatt tgattcaaac aaggctatgg ttcctaaact aggaactggc      1140
cttagttttg acagcacagg tgccattaca gtaggaaaca aaaataatga taagctaact    1200
ttgtggacca caccagctcc atctcctaac tgtagactaa atgcagagaa agatgctaaa    1260
ctcactttgg tcttaacaaa atgtggcagt caaatacttg ctacagtttc agttttggct    1320
gttaaaggca gtttggctcc aatatctgga acagttcaaa gtgctcatct tattataaga    1380
tttgacgaaa atggagtgct actaaacaat tccttcctgg acccagaata ttggaacttt    1440
agaaatggag atcttactga aggcaacgct gttggattta tgcctaacct atcagcttat    1500
ccaaaatctc acggtaaaac tgccaaaagt aacattgtca gtcaagtttta cttaaacgga    1560 gacaaaacta aacctgtaac actaaccatt acactaaacg gtacacagga acaggagac     1620 acaactagtt tcttctgcgt ttccgacggt ggtggttcct cctgcccggc ggccgctcct    1680
tccgcatact ctatgtcatt ttcatgggac tggtctggcc acaactacat taatgaaata    1740
tttgccacat cctcttacac tttttcatac attgcccaag aataa                    1785

<210> SEQ ID NO 13
<211> LENGTH: 12
<212> TYPE: PRT
<213> ORGANISM: Artificial Sequence
<220> FEATURE:
<223> OTHER INFORMATION: peptide

<400> SEQUENCE: 13

Phe Cys Val Ala Ser Arg Gly Gly Ser Ser Cys Tyr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: peptide

<400> SEQUENCE: 14

Phe Cys Lys Val Val Gly Gly Gly Ser Ser Cys Ser Pro
1               5                   10

<210> SEQ ID NO 15
<211> LENGTH: 13
<212> TYPE: PRT
<213> ORGANISM: Artificial Sequence
<220> FEATURE:
<223> OTHER INFORMATION: peptide

<400> SEQUENCE: 15

Phe Phe Cys Val Ser Asp Gly Gly Gly Ser Ser Cys Pro
1               5                   10

<210> SEQ ID NO 16
<211> LENGTH: 7
```

```
<212> TYPE: PRT
<213> ORGANISM: Artificial Sequence
<220> FEATURE:
<223> OTHER INFORMATION: fragment

<400> SEQUENCE: 16

Thr Ser Gly Ala Ala Ala Pro
 1               5

<210> SEQ ID NO 17
<211> LENGTH: 21
<212> TYPE: DNA
<213> ORGANISM: Artificial Sequence
<220> FEATURE:
<223> OTHER INFORMATION: fragment

<400> SEQUENCE: 17
actagtggtg cggccgctcc a                                              21

<210> SEQ ID NO 18
<211> LENGTH: 44
<212> TYPE: PRT
<213> ORGANISM: Artificial Sequence
<220> FEATURE:
<223> OTHER INFORMATION: fragment

<400> SEQUENCE: 18

Ser Ile Val Gly Ser Gly Ser Gly Ser Gly Ser Gly Ser Gly Ser Gly
 1               5                  10                  15

Ser Gly Ser Gly Ser Gly Ser Gly Ser Gly Ser Gly Ser Gly Ser Gly
            20                  25                  30

Ser Gly Ser Gly Lys Glu Val Pro Met Gly Ala Ile
        35                  40

<210> SEQ ID NO 19
<211> LENGTH: 135
<212> TYPE: DNA
<213> ORGANISM: Artificial Sequence
<220> FEATURE:
<223> OTHER INFORMATION: fragment

<400> SEQUENCE: 19
agcatcgttg gatctggatc tggatctgga tctggatctg gatctggatc tggatctgga   60
tctggatctg gatctggatc tggatctgga tctggatctg gatctggtaa ggaggtaccg  120
tagatgggtg ccatt                                                   135

<210> SEQ ID NO 20
<211> LENGTH: 48
<212> TYPE: DNA
<213> ORGANISM: Artificial Sequence
<220> FEATURE:
<223> OTHER INFORMATION: oligonucleotide

<400> SEQUENCE: 20
tttatctaga cccagcccta ggaagcttct cctgagtagg acaaatcc                48

<210> SEQ ID NO 21
<211> LENGTH: 32
<212> TYPE: DNA
<213> ORGANISM: Artificial Sequence
<220> FEATURE:
<223> OTHER INFORMATION: oligonucleotide

<400> SEQUENCE: 21
```

```
gggtctagat aaaacgaaag gcccagtctt tc                                    32
```

<210> SEQ ID NO 22
<211> LENGTH: 65
<212> TYPE: DNA
<213> ORGANISM: Artificial Sequence
<220> FEATURE:
<223> OTHER INFORMATION: oligonucleotide

<400> SEQUENCE: 22

```
gaccgcgttt gccggaacgg caatcagcat cgttggttcc ggctctggta aggaggtacc     60
gtagg                                                                 65
```

<210> SEQ ID NO 23
<211> LENGTH: 54
<212> TYPE: DNA
<213> ORGANISM: Artificial Sequence
<220> FEATURE:
<223> OTHER INFORMATION: oligonucleotide

<400> SEQUENCE: 23

```
aattcctacg gtacctcctt accagagccg gaaccaacga tgctgattgc cgtt           54
```

<210> SEQ ID NO 24
<211> LENGTH: 41
<212> TYPE: DNA
<213> ORGANISM: Artificial Sequence
<220> FEATURE:
<223> OTHER INFORMATION: oligonucleotide

<400> SEQUENCE: 24

```
tagggtaccg tagatgggtg ccattacagt aggaaacaaa a                         41
```

<210> SEQ ID NO 25
<211> LENGTH: 30
<212> TYPE: DNA
<213> ORGANISM: Artificial Sequence
<220> FEATURE:
<223> OTHER INFORMATION: oligonucleotide

<400> SEQUENCE: 25

```
aaagaattct ttattcttgg gcaatgtatg                                      30
```

<210> SEQ ID NO 26
<211> LENGTH: 59
<212> TYPE: DNA
<213> ORGANISM: Artificial Sequence
<220> FEATURE:
<223> OTHER INFORMATION: oligonucleotide

<400> SEQUENCE: 26

```
gaccgcgttt gccggaacgg caatcagcat cgttggatcc ggttctggta aggaggtac      59
```

<210> SEQ ID NO 27
<211> LENGTH: 52
<212> TYPE: DNA
<213> ORGANISM: Artificial Sequence
<220> FEATURE:
<223> OTHER INFORMATION: oligonucleotide

<400> SEQUENCE: 27

```
ctccttacca gaaccggatc caacgatgct gattgccgtt ccggcaaacg cg             52
```

<210> SEQ ID NO 28

```
<211> LENGTH: 42
<212> TYPE: DNA
<213> ORGANISM: Artificial Sequence
<220> FEATURE:
<223> OTHER INFORMATION: oligonucleotide

<400> SEQUENCE: 28
gatctggttc cggttctggc tccggctctg gttctggttc cg                    42

<210> SEQ ID NO 29
<211> LENGTH: 42
<212> TYPE: DNA
<213> ORGANISM: Artificial Sequence
<220> FEATURE:
<223> OTHER INFORMATION: oligonucleotide

<400> SEQUENCE: 29
gatccggaac cagaaccaga gccggagcca gaaccggaac ca                    42

<210> SEQ ID NO 30
<211> LENGTH: 35
<212> TYPE: DNA
<213> ORGANISM: Artificial Sequence
<220> FEATURE:
<223> OTHER INFORMATION: oligonucleotide

<400> SEQUENCE: 30
gttttgacgc tagcggtgcc attacagtag gaaac                            35

<210> SEQ ID NO 31
<211> LENGTH: 36
<212> TYPE: DNA
<213> ORGANISM: Artificial Sequence
<220> FEATURE:
<223> OTHER INFORMATION: oligonucleotide

<400> SEQUENCE: 31
ggagatctta ctgaaggcaa cgctgttgga tttatg                           36

<210> SEQ ID NO 32
<211> LENGTH: 24
<212> TYPE: DNA
<213> ORGANISM: Artificial Sequence
<220> FEATURE:
<223> OTHER INFORMATION: oligonucleotide

<400> SEQUENCE: 32
tctgatttaa tctgtatcag gctg                                        24

<210> SEQ ID NO 33
<211> LENGTH: 25
<212> TYPE: DNA
<213> ORGANISM: Artificial Sequence
<220> FEATURE:
<223> OTHER INFORMATION: oligonucleotide

<400> SEQUENCE: 33
ccaagtgcat actctatgtc atttt                                       25

<210> SEQ ID NO 34
<211> LENGTH: 51
<212> TYPE: DNA
<213> ORGANISM: Artificial Sequence
<220> FEATURE:
<223> OTHER INFORMATION: oligonucleotide

<400> SEQUENCE: 34
```
tcgaattctt taagcggccg caccactagt ttcttgggca atgtatgaaa a        51

<210> SEQ ID NO 35
<211> LENGTH: 23
<212> TYPE: DNA
<213> ORGANISM: Artificial Sequence
<220> FEATURE:
<223> OTHER INFORMATION: oligonucleotide

<400> SEQUENCE: 35
aggcagtttg gctccaatat ctg        23

<210> SEQ ID NO 36
<211> LENGTH: 39
<212> TYPE: DNA
<213> ORGANISM: Artificial Sequence
<220> FEATURE:
<223> OTHER INFORMATION: oligonucleotide

<400> SEQUENCE: 36
gcggccgcac cactagttgt gtctcctgtt tcctgtgta        39

<210> SEQ ID NO 37
<211> LENGTH: 42
<212> TYPE: DNA
<213> ORGANISM: Artificial Sequence
<220> FEATURE:
<223> OTHER INFORMATION: oligonucleotide

<400> SEQUENCE: 37
actagtggtg cggccgctcc aagtgcatac tctatgtcat tt        42

<210> SEQ ID NO 38
<211> LENGTH: 24
<212> TYPE: DNA
<213> ORGANISM: Artificial Sequence
<220> FEATURE:
<223> OTHER INFORMATION: oligonucleotide

<400> SEQUENCE: 38
ggatgtggca aatatttcat taat        24

<210> SEQ ID NO 39
<211> LENGTH: 5
<212> TYPE: PRT
<213> ORGANISM: Artificial Sequence
<220> FEATURE:
<223> OTHER INFORMATION: fragment

<400> SEQUENCE: 39

Ser Gly Ala Ala Ala
 1               5

<210> SEQ ID NO 40
<211> LENGTH: 25
<212> TYPE: DNA
<213> ORGANISM: Artificial Sequence
<220> FEATURE:
<223> OTHER INFORMATION: oligonucleotide

<400> SEQUENCE: 40
acaggaaaca ggagacacaa ctagt        25

<210> SEQ ID NO 41
<211> LENGTH: 25

```
<212> TYPE: DNA
<213> ORGANISM: Artificial Sequence
<220> FEATURE:
<223> OTHER INFORMATION: oligonucleotide

<400> SEQUENCE: 41
tagagtatgc acttggagcg gccgc                                          25

<210> SEQ ID NO 42
<211> LENGTH: 18
<212> TYPE: DNA
<213> ORGANISM: Artificial Sequence
<220> FEATURE:
<223> OTHER INFORMATION: oligonucleotide

<400> SEQUENCE: 42
aattcccatt taaatggg                                                  18

<210> SEQ ID NO 43
<211> LENGTH: 6
<212> TYPE: PRT
<213> ORGANISM: Artificial Sequence
<220> FEATURE:
<223> OTHER INFORMATION: peptide

<400> SEQUENCE: 43

Gly Arg Gly Asp Ser Pro
 1               5

<210> SEQ ID NO 44
<211> LENGTH: 6
<212> TYPE: PRT
<213> ORGANISM: Artificial Sequence
<220> FEATURE:
<223> OTHER INFORMATION: peptide

<400> SEQUENCE: 44

Gly Arg Gly Glu Ser Pro
 1               5

<210> SEQ ID NO 45
<211> LENGTH: 4
<212> TYPE: PRT
<213> ORGANISM: Artificial Sequence
<220> FEATURE:
<223> OTHER INFORMATION: fragment

<400> SEQUENCE: 45

Thr Ala Tyr Thr
 1

<210> SEQ ID NO 46
<211> LENGTH: 14
<212> TYPE: PRT
<213> ORGANISM: Artificial Sequence
<220> FEATURE:
<223> OTHER INFORMATION: peptide

<400> SEQUENCE: 46

Ser Ala Cys Asp Cys Arg Gly Asp Cys Phe Cys Thr Ser
 1               5                  10

<210> SEQ ID NO 47
<211> LENGTH: 12
<212> TYPE: DNA
<213> ORGANISM: Artificial Sequence
<220> FEATURE:
```

```
-continued

<223> OTHER INFORMATION: fragment

<400> SEQUENCE: 47
acagcctata ca                                                    12
```

What is claimed:

1. A recombinant adenovirus having a modified fiber protein which comprises a peptide ligand for a cell surface binding site other than CAR, said peptide ligand comprising the amino acid sequence selected from the group consisting of SEQ ID NO:13, SEQ ID NO:14 and SEQ ID NO:15.

2. A recombinant adenovirus of claim 1, wherein said peptide ligand is contained within a loop domain of a fiber protein knob.

3. A recombinant adenovirus of claim 1, wherein said modified fiber protein is an Ad5 fiber protein.

4. A recombinant adenovirus of claim 1, wherein said modified fiber protein does not bind CAR.

5. An isolated adenovirus fiber protein which comprises a peptide ligand for a cell surface binding site other than CAR, said peptide ligand comprising the amino acid sequence selected from the group consisting of SEQ ID NO:13, SEQ ID NO:14 and SEQ ID NO:15.

6. An isolated adenovirus fiber protein of claim 5, wherein said peptide ligand is contained within a loop domain of a fiber protein knob.

7. An isolated adenovirus fiber protein of claim 5, wherein said modified fiber protein is an Ad5 fiber protein.

8. A recombinant adenovirus of claim 5, wherein said modified fiber protein does not bind CAR.

9. An isolated nucleic acid molecule encoding a modified adenovirus fiber protein which comprises a peptide ligand for a cell surface binding site other than CAR, said peptide ligand comprising the amino acid sequence selected from the group consisting of SEQ ID NO:13, SEQ ID NO:14 and SEQ ID NO:15.

10. An expression vector for expressing a modified adenovirus fiber protein in a recombinant cell wherein said expression vector comprises a nucleic acid molecule of claim 9.

11. An isolated host cell which expresses a modified adenovirus fiber protein wherein said host cell contains the expression vector of claim 10.

12. A process of expressing a modified adenovirus fiber protein in a recombinant host cell, comprising:
(a) transfecting the expression vector of claim 10 into a suitable host cell; and
(b) culturing the host cell of step (a) under conditions which allow expression of said modified adenovirus fiber protein from said expression vector.

* * * * *